(12) United States Patent
Adam et al.

(10) Patent No.: US 8,227,613 B2
(45) Date of Patent: Jul. 24, 2012

(54) HETEROARYL CARBOXAMIDE DERIVATIVES

(75) Inventors: Jean-Michel Adam, Rosenau (FR); Johannes Aebi, Binningen (CH); Alfred Binggeli, Binningen (CH); Luke Green, Basel (CH); Guido Hartmann, Loerrach (DE); Hans P. Maerki, Basel (CH); Patrizio Mattei, Riehen (CH); Fabienne Ricklin, Hombourg (FR); Olivier Roche, Folgensbourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 495 days.

(21) Appl. No.: 12/484,552

(22) Filed: Jun. 15, 2009

(65) Prior Publication Data

US 2009/0318467 A1    Dec. 24, 2009

(30) Foreign Application Priority Data

Jun. 18, 2008  (EP) ..................... 08158499

(51) Int. Cl.
*C07D 211/68*    (2006.01)
*A61K 31/445*    (2006.01)

(52) U.S. Cl. ........................ 546/194; 514/318
(58) Field of Classification Search ................... 546/194
See application file for complete search history.

(56) References Cited

FOREIGN PATENT DOCUMENTS

| DE | 25 38 950 | 3/1977 |
|---|---|---|
| EP | 0228845 | 7/1987 |
| WO | WO 03/020716 | 3/2003 |
| WO | WO 2004/043925 | 5/2004 |
| WO | WO 2007/075629 | 7/2007 |
| WO | WO 2007/116313 | 10/2007 |
| WO | WO 2008/060621 | 5/2008 |

OTHER PUBLICATIONS

Manuel Feria et al, *Expert Opinion on Therapeutic Patents*, Informa Healthcare, 16:1 (2006) 49-57 XP002421316.
Naya A et al, *Expert Opinion on Therapeutic Patents*, Informa Healthcare, 14:1 (2004) 7-16 XP002415982.
Ness T L et al, *Expert Opinion on Therapeutic Patents*, Informa Healthcare, 16:18 (2006) 1051-1065 XP002539603.
Guillaume et al., Journal of Fluorine Chemistry, 69, pp. 253-256 (1994).
Guillaume et al., Synthesis, 8, pp. 920-921 (1995).
Volonterio et al., Organic Letters, 9(19), pp. 3733-3736 (2007).
Wu et al., Organic Letters, 1(5), pp. 745-747 (1999).

*Primary Examiner* — Janet Andres
*Assistant Examiner* — John Mabry
(74) *Attorney, Agent, or Firm* — George W. Johnston; Patricia S. Rocha-Tramaloni; Gene J. Yao

(57) ABSTRACT

The invention is concerned with novel heteroaryl carboxamide derivatives of formula (I),

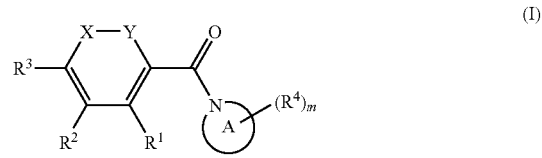

wherein

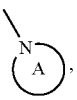

m, X, Y, $R^1$, $R^2$, $R^3$ and $R^4$ are as defined in the description and in the claims, as well as physiologically acceptable salts thereof. These compounds are antagonists of CCR-2 receptor, CCR-5 receptor and/or CCR-3 receptor and can be used as medicaments.

21 Claims, No Drawings

HETEROARYL CARBOXAMIDE DERIVATIVES

PRIORITY TO RELATED APPLICATION(S)

This application claims the benefit of European Patent Application No. 08158499.7, filed Jun. 18, 2008, which is hereby incorporated by reference in its entirety.

BACKGROUND OF THE INVENTION

Chemokines are a family of small, secreted proinflammatory cytokines functioning as chemoattractants for leukocytes. They promote trafficking of leukocytes from vascular beds into surrounding tissues in response to inflammatory signals. Chemotaxis starts upon chemokine binding to receptors (GPCRs) by initiating signaling pathways involving increased Ca-flux, inhibition of cAMP production, rearrangements of the cytoskeleton, activation of integrins and of cell motility processes and an increase in the expression of adhesion proteins.

Proinflammatory chemokines are considered to be involved in the development of atherosclerosis and other important diseases with inflammatory components like rheumatoid arthritis, asthma, multiple sclerosis, transplant rejection and ischemia reperfusion injury with specific prominent effects in nephropathy and peripheral vascular diseases. Monocyte Chemotactic Protein 1 is considered to be the major stimulated chemokine mediating inflammatory processes in these diseases through the CCR2 receptor on monocytes and on some T lymphocytes. In addition MCP-1/CCR2 are in discussion to be related to the progression of the metabolic syndrome to more severe stages of obese and diabetic diseases.

CCR2 has also been linked to HIV infection, and consequently the course of autoimmune diseases, through its heterodimerization with CCR5 which has a role as coreceptor for viral entry into host cells.

Thus, CCR2 can be a target of a new medicine for treatment of peripheral vascular diseases, and more specifically for treatment of patients with critical limb ischemia. Furthermore, study results and experiences from the development of a new CCR2 medicine for this indication may facilitate a follow-up development for treatment of atherosclerosis. There is a large body of information from animal models of MCP-1 and CCR2 ko mice in wt or apoE–/– or LDL-R–/– backgrounds showing that the MCP-1/CCR2 pathway is essential for monocyte/macrophage recruitment, and also for intimal hyperplasia and the formation and stability of atherosclerotic lesions. In addition, numerous reports describe involvement of the MCP-1/CCR2 pathway in man post injury and in various inflammatory processes, including such in vascular beds.

The present invention provides the novel compounds of formula (I) which are CCR2 receptor antagonists, with some antagonist activity also at CCR-3 and CCR-5.

SUMMARY OF THE INVENTION

The invention is concerned with novel heteroaryl carboxamide derivatives of formula (I),

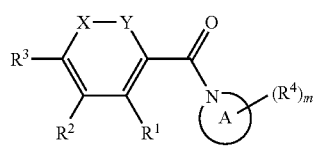
(I)

or tautomers, prodrugs, esters, or pharmaceutically acceptable salts thereof, wherein:

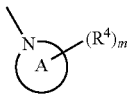

is a heterocyclyl substituted by m $R^4$ groups wherein m is 0, 1, 2, 3 or 4; and wherein said heterocyclyl is a non-aromatic mono-cyclic radical of four to eight ring atoms, in which one or two ring atoms are nitrogen atoms, with the remaining ring atoms being carbon atoms; and wherein said heterocyclyl :(1) does not contain a nitrogen atom which is directly bonded to a heteroatom; and (2) contains at least one nitrogen atom not directly bonded to a carbonyl group;

X—Y is selected from the group consisting of:
(1) N=C(NR$^{10}$R$^{11}$),
(2) C(NR$^6$R$^7$)=N,
(3) CR$^8$=N,
(5) N(O)=CR$^{12}$,
(4) C(O)—NR$^9$,
(6) N(R$^5$)—C(O),
(7) CR8=N(O),
(8) N=N, (9) 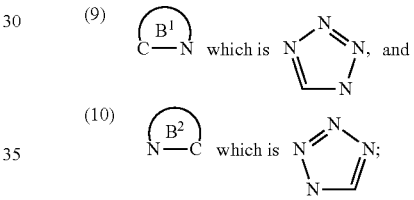 , and (10)

$R^1$ is selected from the group consisting of: (1) $C_{1-6}$ alkyl, (2) $C_{3-7}$ cycloalkyl, (3) $C_{2-6}$ alkenyl, (4) $C_{2-6}$ alkynyl, (5) optionally substituted $C_{3-7}$ cycloalkyl, (6) optionally substituted $C_{3-7}$ cycloalkyl $C_{1-6}$ alkyl, (7) $C_{1-6}$ alkoxy, (8) halo $C_{1-6}$ alkoxy, (9) halo $C_{1-6}$ alkyl, (10) $C_{3-7}$ cycloalkoxy, (11) heteroalkyl, (12) heteroalkoxy, (13) halogen, (14) optionally substituted phenyl which does not have nitro as a substituent, (15) optionally substituted heteroaryl, and (16) optionally substituted heterocyclyl;

$R^2$ is hydrogen, $C_{1-6}$ alkyl, $C_{2-6}$ alkynyl, $C_{1-6}$ alkoxy, halo $C_{1-6}$ alkyl, cyano or halogen;

$R^3$ is phenyl or heteroaryl wherein said heteroaryl is an aromatic mono-cyclic radical of six ring atoms, in which one or two ring atoms are nitrogen atoms with the remaining ring atoms being carbon atoms, and wherein said phenyl or said heteroaryl are substituted by one, two or three substituents independently selected from the group consisting of $C_{1-8}$ alkyl, halo $C_{1-6}$ alkyl, $C_{1-6}$ alkoxy, halo $C_{1-6}$ alkoxy, halogen and cyano;

each $R^4$ is: (a) attached to a ring carbon atom and independently selected from the group consisting of: (1) hydrogen, (2) $C_{1-6}$ alkyl, (3) hydroxy $C_{1-6}$ alkyl or halo $C_{1-6}$ alkyl, (4) heteroalkyl, (5) $C_{2-6}$ alkenyl, (6) $C_{2-6}$ alkynyl, (7) hydroxy $C_{3-6}$ alkenyl, (8) hydroxy $C_{3-6}$ alkynyl, (9) $C_{1-6}$ alkoxy $C_{3-6}$ alkenyl, (10) $C_{1-6}$ alkoxy $C_3C_{3-6}$ alkynyl, (11) hydroxy, (12) $C_{1-6}$ alkoxy, (13) halo $C_{1-6}$ alkoxy, (14) heteroalkoxy, (15) halogen, (16) cyano, (17) optionally substituted phenyl, (18) optionally substituted $C_{3-7}$ cycloalkyl, (19)

optionally substituted $C_{3-7}$ cycloalkyl $C_{1-6}$ alkyl, (20) optionally substituted heteroaryl, (21) optionally substituted heterocyclyl, (22) optionally substituted phenyl-$C_{1-6}$ alkyl, (23) optionally substituted heteroaryl-$C_{1-6}$ alkyl, (24) optionally substituted heterocyclyl-$C_{1-6}$ alkyl, (25) nitro, (26) carboxy, (27) formyl, (28) acyl, (29) $C_{1-6}$ alkoxycarbonyl, (30) carbamoyl, (31) mono- or di-$C_{1-6}$ alkyl substituted aminocarbonyl, (32) $C_{1-6}$ alkylthio, (33) $C_{1-6}$ alkylsulfinyl, (34) $C_{1-6}$ alkylsulfonyl, and (35) amino optionally substituted by one or two substituents independently selected from the group consisting of $C_{1-6}$ alkyl, heteroalkyl, optionally substituted $C_{3-7}$ cycloalkyl and optionally substituted heterocyclyl; or (b) attached to a ring nitrogen atom and independently selected from the group consisting of: (1) hydrogen, (2) $C_{1-6}$ alkyl, (3) hydroxy $C_{1-6}$ alkyl or halo $C_{1-6}$ alkyl, (4) heteroalkyl, (5) $C_{2-6}$ alkenyl, (6) $C_{2-6}$ alkynyl, (7) hydroxy $C_{3-6}$ alkenyl, (8) hydroxy $C_{3-6}$ alkynyl, (9) $C_{1-6}$ alkoxy $C_{3-6}$ alkenyl, (10) $C_{1-6}$ alkoxy $C_{3-6}$ alkynyl, (11) optionally substituted $C_{3-7}$ cycloalkyl, (12) optionally substituted $C_{3-7}$ cycloalkyl $C_{-6}$ alkyl, (13) optionally substituted heterocyclyl, and (14) optionally substituted heterocyclyl $C_{1-6}$ alkyl;

$R^5$ is $C_{1-6}$ alkyl, $C_{3-7}$ cycloalkyl, halo $C_{1-6}$ alkyl, or heteroalkyl;

$R^6$ and $R^{10}$ are independently of each other selected from the group consisting of: hydrogen, $C_{1-6}$ alkyl, $C_{1-6}$ alkanoyl, $C_{1-6}$ alkylsulfonyl, $C_{3-7}$ cycloalkyl, optionally substituted phenyl-$C_{1-6}$ alkyl, optionally substituted heteroaryl-$C_{1-6}$ alkyl, and optionally substituted heterocyclyl-$C_{1-6}$ alkyl;

$R^7$ and $R^{11}$ are idenpendently of each other selected from the group consisting of: hydrogen, $C_{1-6}$ alkyl, $C_{3-7}$ cycloalkyl, halo $C_{1-6}$ alkyl, $C_{1-6}$ alkanoyl, and heteroalkyl;

$R^8$ is selected from the group consisting of: (1) hydrogen, (2) hydroxy, (3) mercapto, (4) $C_{1-6}$ alkyl, (5) $C_{3-7}$ cycloalkyl, (6) $C_{2-6}$ alkenyl, (7) $C_{2-6}$ alkynyl, (8) optionally substituted $C_{3-7}$ cycloalkyl, (9) optionally substituted $C_{3-7}$ cycloalkyl $C_{1-6}$ alkyl, (10) $C_{1-6}$ alkoxy, (11) $C_{1-6}$ alkylthio, (12) halo $C_{1-6}$ alkoxy, (13) halo $C_{1-6}$ alkyl, (14) $C_{3-7}$ cycloalkoxy, (15) heteroalkyl, (16) heteroalkoxy, (17) halogen, (18) cyano, (19) optionally substituted phenyl, (20) optionally substituted heteroaryl, (21) optionally substituted heterocyclyl, (22) optionally substituted phenyloxy, (23) optionally substituted heteroaryloxy; (24) optionally substituted phenylthio, (25) optionally substituted heteroarylthio; (26) optionally substituted phenyl-$C_{1-6}$ alkoxy, (27) optionally substituted heteroaryl-$C_{1-6}$ alkoxy, (28) $C_{1-6}$ alkoxy-carbonyl, (29) carboxy, and (30) -$CONR^{13}R^{14}$;

$R^9$ is hydrogen, $C_{1-6}$ alkyl, $C_{3-7}$ cycloalkyl, halo $C_{1-6}$ alkyl, heteroalkyl, optionally substituted heteroaryl, optionally substituted phenyl-$C_{1-6}$ alkyl, or optionally substituted heteroaryl-$C_{1-6}$ alkyl;

$R^{12}$ is hydrogen, $C_{1-6}$ alkyl, halo $C_{1-6}$ alkyl, heteroalkyl, optionally substituted $C_{3-7}$ cycloalkyl, optionally substituted $C_{3-7}$ cycloalkyl $C_{1-6}$ alkyl, optionally substituted phenyl, optionally substituted heteroaryl, or optionally substituted heterocyclyl; and $R^{13}$ is hydrogen, $C_{1-6}$ alkyl, heteroalkyl, optionally substituted $C_{3-7}$ cycloalkyl, optionally substituted heterocyclyl, optionally substituted aryl, or optionally substituted heteroaryl; and $R^{14}$ is hydrogen, $C_{1-6}$ alkyl or heteroalkyl; or alternatively, $R^{13}$ and $R^{14}$ taken together with the nitrogen atom to which they are attached, form an optionally substituted heterocyclyl ring;

except that [4-isobutyl-6-(2-isopropyl-phenyl)-pyridazin-3-yl]-(3-isopropyl piperazin-1-yl)-methanone and (3-benzyl-piperazin-1-yl)4-isobutyl-6-(2-isopropyl-phenyl)-pyridazin-3- yl]-methanone are excluded from the genus of formula (I).

Further, the invention is concerned with a process for the manufacture of the above compounds, pharmaceutical compositions which contain such compounds, and the use of these compounds for the production of pharmaceutical compositions.

The compounds of formula (I) are CCR2 receptor (Chemokine Receptor 2/Monocyte Chemotactic Protein 1 Receptor) antagonists and also CCR-5 receptor (Chemokine Receptor 5) and/or CCR-3 receptor (Chemokine Receptor 3) antagonists and thus may be useful in treating diseases and disorders associated with these receptors.

DETAILED DESCRIPTION OF THE INVENTION

Unless otherwise indicated, the following definitions are set forth to illustrate and define the meaning and scope of the various terms used to describe the invention herein. As used herein,

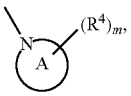

refers to a heterocyclyl substituted by m $R^4$ groups wherein m is 0, 1, 2, 3 or 4.

The term "heteroatom" means a nitrogen atom, an oxygen atom or a sulphur atom.

The term "halogen" or "halo" refers to fluoro, chloro, bromo or iodo. Preferred "halogen" groups are fluoro and chloro.

Unless otherwise indicated, the term "hydrogen" or "hydro" refers to the moiety of a hydrogen atom (—H) and not $H_2$.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, isopropyl, n-butyl, s-butyl, t-butyl. $C_{1-4}$ alkyl or $C_{1-3}$ alkyl is more preferred.

The term "hydroxy $C_{1-6}$ alkyl" means a $C_{1-6}$ alkyl substituted by one or more hydroxy group(s).

The term "halo $C_{1-6}$ alkyl" means a $C_{1-6}$ alkyl substituted by one or more of the same or different halogen atoms. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl. In certain preferred embodiments the "halo $C_{1-6}$ alkyl" is a chloro- or fluoro-$C_{1-6}$ alkyl. The most preferred "halo $C_{1-6}$ alkyl" is trifluoromethyl.

The term "$C_{1-6}$ alkylene", alone or in combination with other groups, means a branched or straight-chain saturated divalent hydrocarbon radical of one to six carbon atoms, such as methylene, ethylene, tetramethylethylene.

The term "$C_{3-7}$ cycloalkyl", alone or in combination with other groups, means a saturated monovalent mono-cyclic hydrocarbon radical of three to seven ring carbons, e.g., cyclopropyl, cyclobutyl, cyclohexyl.

The term "$C_{1-6}$ alkoxy", alone or in combination with other groups, means the group R'—O—, wherein R' is a $C_{1-6}$ alkyl.

The term "$C_{1-6}$ alkoxy-carbonyl" refers to the group R—C(O)—, wherein R is $C_{1-6}$ alkoxy as defined above.

The term "halo $C_{1-6}$ alkoxy", alone or in combination with other groups, means a $C_{1-6}$ alkoxy substituted by one or more halogens. In certain preferred embodiments the halo of the halo $C_{1-6}$ alkoxy is substituted by one or three halogens.

The term "$C_{2-6}$ alkenyl", alone or in combination with other groups, means a straight-chain or branched hydrocarbon residue comprising a carbon-carbon double bond, having two to six carbon atoms. This term is further exemplified by such radicals as ethenyl, 2-propenyl.

The term "hydroxy $C_{3-6}$ alkenyl" means a $C_{3-6}$ alkenyl substituted by one or more hydroxy groups. In certain preferred embodiments the $C_{3-6}$ alkenyl is substituted by one or two hydroxy groups.

The term "$C_{1-6}$ alkoxy $C_{3-6}$ alkenyl" means a $C_{3-6}$ alkenyl substituted by one or more $C_{1-6}$ alkoxy groups. In certain preferred embodiments the $C_{3-6}$ alkenyl is substituted by one or two $C_{1-6}$ alkoxy groups.

The term "$C_{2-6}$-alkynyl", alone or in combination with other groups, means a straight-chain or branched hydrocarbon residue comprising a carbon-carbon triple bond, having two to six carbon atoms. This term is further exemplified by such radicals as ethynyl, 2-propynyl.

The term "hydroxy $C_{3-6}$ alkynyl" means a $C_{3-6}$ alkynyl substituted by one or more hydroxy groups. In certain preferred embodiments, the $C_{3-6}$ alkynyl is substituted by one or two hydroxy groups.

The term "$C_{1-6}$ alkoxy $C_{3-6}$ alkenyl" means a $C_{3-6}$ alkynyl substituted by one or more $C_{1-6}$ alkoxy groups. In certain preferred embodiments, the $C_{3-6}$ alkynyl is substituted by one or two $C_{1-6}$ alkoxy groups.

The term "acyl" or "$C_{1-6}$alkanoyl" means R—C(O)—, in which R is $C_{1-6}$ alkyl, halo $C_{1-6}$ alkyl, $C_{3-7}$ cycloalkyl or $C_{3-7}$ cycloalkyl $C_{1-6}$ alkyl.

The term "heteroalkyl" means a $C_{1-6}$ alkyl substituted by one or more substituents selected independently from the group consisting of nitro, hydroxy, cyano, $C_{1-6}$ alkoxy, formyl, acyl, carboxy, $C_{1-6}$ alkylthio, $C_{1-6}$ alkyl sulfinyl, $C_{1-6}$ alkyl sulfonyl, carbamoyl, amino and mono- or di-$C_{1-6}$ alkyl substituted amino.

The term "heteroalkoxy" means $C_{1-6}$ alkoxy substituted by one or more substituents selected independently from the group consisting of nitro, hydroxy, cyano, $C_{1-6}$ alkoxy, formyl, acyl, carboxy, $C_{1-6}$ alkylthio, $C_{1-6}$ alkyl sulfinyl, $C_{1-6}$ alkyl sulfonyl, carbamoyl, amino and mono- or di-$C_{1-6}$ alkyl substituted amino.

The term "heterocyclyl" means non-aromatic mono-cyclic radicals of four to seven ring atoms, in which one to three ring atoms are heteroatoms independently selected from N, O and $S(O)_n$ (where n is an integer from 0 to 2), the remaining ring atoms being C. In particular, the term "heterocyclyl" includes, but is not limited to, tetrahydrofuranyl, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, and the derivatives thereof. The most preferred heterocyclyls are piperazinyl, pyrolindinyl or piperidinyl.

The term "heteroaryl" means an aromatic mono-cyclic radical of 5 or 6 ring atoms, having one to three ring heteroatoms independently selected from N, O, and S, with the remaining ring atoms being C. More specifically the term "heteroaryl" includes, but is not limited to, pyridinyl, furanyl, thienyl, thiazolyl, isothiazolyl, triazolyl, imidazolyl, isoxazolyl, pyrrolyl, pyrimidinyl, pyrazolyl, pyrazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof. The most preferred heteroaryls are pyridinyl, pyrimidinyl, triazolyl, pyrazolyl, pyrazinyl.

The term "optionally substituted $C_{3-7}$ cycloalkyl" means a $C_{3-7}$ cycloalkyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and acylamino.

The term "optionally substituted $C_{3-7}$ cycloalkyl —$C_{1-6}$ alkyl" means the group $R^{8ae}$-$R^{8af}$—, wherein $R^{8ae}$ and $R^{8af}$ are, respectively, "optionally substituted $C_{3-7}$ cycloalkyl" and "$C_{1-6}$ alkyl" as defined above.

The term "optionally substituted phenyl" means a phenyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and acylamino.

The term "optionally substituted phenyloxy" means the group $R^{8a}$—O—, wherein $R^{8a}$ is "optionally substituted phenyl" as defined above.

The term "optionally substituted phenylthio" means the group $R^{8a'}$—S—, wherein $R^{8a'}$ is "optionally substituted phenyl" as defined above.

The term "optionally substituted phenyl-$C_{1-6}$ alkoxy" means the group $R^{8aa}$—$R^{8ab}$—, wherein $R^{8aa}$ and $R^{8ab}$ are, respectively, "optionally substituted phenyl" and "$C_{1-6}$ alkoxy" as defined above.

The term "optionally substituted phenyl-$C_{1-6}$ alkyl" means the group $R^{8ac}$-$R^{8ad}$—, wherein $R^{8ac}$ and $R^{8ad}$ are, respectively, "optionally substituted phenyl" and "$C_{1-6}$ alkyl" as defined above.

The term "optionally substituted heterocyclyl" means a heterocyclyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and acylamino.

The term "optionally substituted heterocyclyl-$C_{1-6}$ alkyl" means the group $R^{8be}$-$R^{8bf}$—, wherein $R^{8be}$ and $R^{bf}$ are, respectively, "optionally substituted heterocyclyl" and "$C_{1-6}$ alkyl" as defined above.

The term "optionally substituted heteroaryl" means a heteroaryl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and acylamimo.

The term "optionally substituted heteroaryloxy" means $R^{8b}$—O—, wherein $R^{8b}$ is "optionally substituted heteroaryl" as defined above.

The term "optionally substituted heteroarylthio" means $R^{8b'}$—S—, wherein $R^{8b'}$ is "optionally substituted heteroaryl" as defined above.

The term "optionally substituted heteroaryl-$C_{1-6}$ alkoxy" means the group $R^{8ba}$-$R^{8bb}$—, wherein $R^{8ba}$ and $R^{8bb}$ are, respectively, "optionally substituted heteroaryl" and "$C_{1-6}$ alkoxy" as defined above.

The term "optionally substituted heteroaryl-$C_{1-6}$ alkyl" means the group $R^{8bc}$-$R^{bd}$—, wherein $R^{8bc}$ and $R^{8bd}$ are, respectively, "optionally substituted heteroaryl" and "$C_{1-6}$ alkyl" as defined above.

The terms, "$C_{1-6}$ alkylsulfonyl", "$C_{1-6}$ alkylsulfinyl" and "$C_{1-6}$ alkylthio", alone or combination with other groups, means $C_{1-6}$ alkyl-$SO_2$—, $C_{1-6}$ alkyl-SO— and $C_{1-6}$ alkyl-S—, respectively.

Unless otherwise indicated, in reference to a particular group or molecule, the term "substituted" refers to the fact that at least one of the hydrogen atoms of that group or molecule is replaced by some other substituent.

Unless otherwise indicated, the terms "optional" or "optionally" means that the subsequently described event or circumstance may but need not occur, and that the description includes instances where the event or circumstance occurs and instances in which it does not. For example, an "aryl group optionally substituted with an alkyl group" means that the alkyl may but need not be present, and the description includes situations where the aryl group is substituted with an alkyl group and situations where the aryl group is not substituted with the alkyl group.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 100 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, hydrobromic acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) may also be present in the form of pharmaceutically acceptable esters (i.e., the methyl and ethyl esters of the acids of formula I to be used as prodrugs).

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt of any such compound).

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

In addition, certain compounds of formula (I) may exist in more than one tautomeric form. The present invention encompasses all such tautomers, as well as mixtures thereof.

In detail, the present invention relates to the compounds of formula (I):

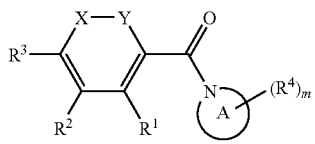

or tautomers, prodrugs, esters or pharmaceutically acceptable salts thereof, wherein:

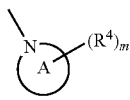

is a heterocyclyl substituted by m $R^4$ groups wherein m is 0, 1, 2, 3 or 4; and wherein said heterocyclyl is a non-aromatic mono-cyclic radical of four to eight ring atoms, in which one or two ring atoms are nitrogen atoms, with the remaining ring atoms being carbon atoms; and wherein said structure: (1) does not contain a nitrogen atom which is directly bonded to a heteroatom; and (2) contains at least one nitrogen atom not directly bonded to a carbonyl group;

X—Y is selected from the group consisting of:
- (1) N=C(NR$^{10}$R$^{11}$),
- (2) C(NR$^6$R$^7$)=N,
- (3) CR$^8$=N,
- (4) C(O)—NR$^9$,
- (5) N(O)=CR$^{12}$,
- (6) N(R$^5$)—C(O),
- (7) CR$^8$=N(O),
- (8) N=N, (9) 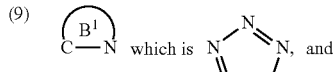

(10) 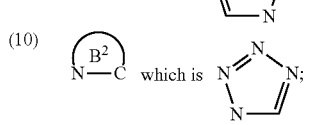

$R^1$ is selected from the group consisting of: (1) $C_{1-6}$ alkyl, (2) $C_{3-7}$ cycloalkyl, (3) $C_{2-6}$ alkenyl, (4) $C_{2-6}$ alkynyl, (5) optionally substituted $C_{3-7}$ cycloalkyl, (6) optionally substituted $C_{3-7}$ cycloalkyl $C_{1-6}$ alkyl, (7) $C_{1-6}$ alkoxy, (8) halo $C_{1-6}$ alkoxy, (9) halo $C_{1-6}$ alkyl, (10) $C_{3-7}$ cycloalkoxy, (11) heteroalkyl, (12) heteroalkoxy, (13) halogen, (14) optionally substituted phenyl which does not have nitro as a substituent, (15) optionally substituted heteroaryl, and (16) optionally substituted heterocyclyl;

$R^2$ is hydrogen, $C_{1-6}$ alkyl, $C_{2-6}$ alkynyl, $C_{1-6}$ alkoxy, halo $C_{1-6}$ alkyl, cyano or halogen;

$R^3$ is phenyl or heteroaryl wherein said heteroaryl is an aromatic mono-cyclic radical of six ring atoms, in which one or two ring atoms are nitrogen atoms with the remaining ring atoms being carbon atoms, and wherein said phenyl or said heteroaryl are substituted by one, two or three substituents independently selected from the group consisting of $C_{1-8}$ alkyl, halo $C_{1-6}$ alkyl, $C_{1-6}$ alkoxy, halo $C_{1-6}$ alkoxy, halogen and cyano;

each $R^4$ is: (a) attached to a ring carbon atom and independently selected from the group consisting of: (1) hydrogen, (2) $C_{1-6}$ alkyl, (3) hydroxy $C_{1-6}$ alkyl or halo $C_{1-6}$ alkyl, (4) heteroalkyl, (5) $C_{2-6}$ alkenyl, (6) $C_{2-6}$ alkynyl, (7) hydroxy $C_{3-6}$ alkenyl, (8) hydroxy $C_{3-6}$ alkynyl, (9) $C_{1-6}$ alkoxy $C_{3-6}$ alkenyl, (10) $C_{1-6}$ alkoxy $C_{3-6}$ alkynyl, (11) hydroxy, (12) $C_{1-6}$ alkoxy, (13) halo $C_{1-6}$ alkoxy, (14) heteroalkoxy, (15) halogen, (16) cyano, (17) optionally substituted phenyl, (18) optionally substituted $C_{3-7}$ cycloalkyl, (19) optionally substituted $C_{3-7}$ cycloalkyl $C_{1-6}$ alkyl, (20) optionally substituted heteroaryl, (21) optionally substituted heterocyclyl, (22) optionally substituted phenyl-$C_{1-6}$ alkyl, (23) optionally substituted heteroaryl-$C_{1-6}$ alkyl, (24) optionally substituted heterocyclyl-$C_{1-6}$ alkyl, (25) nitro, (26) carboxy, (27) formyl, (28) acyl, (29) $C_{1-6}$ alkoxycarbonyl, (30) carbamoyl, (31) mono- or di-$C_{1-6}$ alkyl substituted aminocarbonyl, (32) $C_{1-6}$ alkylthio, (33) $C_{1-6}$ alkylsulfinyl, (34) $C_{1-6}$ alkylsulfonyl, and (35) amino optionally substituted by one or two substituents independently selected from the group consisting of $C_{1-6}$ alkyl, heteroalkyl, optionally substituted $C_{3-7}$ cycloalkyl and optionally substituted heterocyclyl; or (b) attached to a ring nitrogen atom and independently selected from the group consisting of: (1) hydrogen, (2) $C_{1-6}$ alkyl, (3) hydroxy $C_{1-6}$ alkyl or halo $C_{1-6}$ alkyl, (4) heteroalkyl, (5) $C_{2-6}$ alkenyl, (6) $C_{2-6}$ alkynyl, (7) hydroxy $C_{3-6}$ alkenyl, (8) hydroxy $C_{3-6}$ alkynyl, (9) $C_{1-6}$ alkoxy $C_{3-6}$ alkenyl, (10) $C_{1-6}$ alkoxy $C_{3-6}$ alkynyl, (11) optionally substituted $C_{3-7}$ cycloalkyl, (12) optionally substituted $C_{3-7}$ cycloalkyl $C_{1-6}$ alkyl, (13) optionally substituted heterocyclyl, and (14) optionally substituted heterocyclyl $C_{1-6}$ alkyl;

$R^5$ is $C_{1-6}$ alkyl, $C_{3-7}$ cycloalkyl, halo $C_{1-6}$ alkyl, or heteroalkyl;

$R^6$ and $R^{10}$ are independently of each other selected from the group consisting of: hydrogen, $C_{1-6}$ alkyl, $C_{1-6}$ alkanoyl, $C_{1-6}$ alkylsulfonyl, $C_{3-7}$ cycloalkyl, optionally substituted phenyl-$C_{1-6}$ alkyl, optionally substituted heteroaryl-$C_{1-6}$ alkyl, and optionally substituted heterocyclyl-$C_{1-6}$ alkyl;

$R^7$ and $R^{11}$ are idenpendently of each other selected from the group consisting of: hydrogen, $C_{1-6}$ alkyl, $C_{3-7}$ cycloalkyl, halo $C_{1-6}$ alkyl, $C_{1-6}$ alkanoyl, and heteroalkyl;

$R^8$ is selected from the group consisting of: (1) hydrogen, (2) hydroxy, (3) mercapto, (4) $C_{1-6}$ alkyl, (5) $C_{3-7}$ cycloalkyl, (6) $C_{2-6}$ alkenyl, (7) $C_{2-6}$ alkynyl, (8) optionally substituted $C_{3-7}$ cycloalkyl, (9) optionally substituted $C_{3-7}$ cycloalkyl $C_{1-6}$ alkyl, (10) $C_{1-6}$ alkoxy, (11) $C_{1-6}$ alkylthio, (12) halo $C_{1-6}$ alkoxy, (13) halo $C_{1-6}$ alkyl, (14) $C_{3-7}$ cycloalkoxy, (15) heteroalkyl, (16) heteroalkoxy, (17) halogen, (18) cyano, (19) optionally substituted phenyl, (20) optionally substituted heteroaryl, (21) optionally substituted heterocyclyl, (22) optionally substituted phenyloxy, (23) optionally substituted heteroaryloxy; (24) optionally substituted phenylthio, (25) optionally substituted heteroarylthio; (26) optionally substituted phenyl-$C_{1-6}$ alkoxy, (27) optionally substituted heteroaryl-$C_{1-6}$ alkoxy, (28) $C_{1-6}$ alkoxy-carbonyl, (29) carboxy, and (30) —CONR$^{13}$R$^{14}$;

$R^9$ is hydrogen, $C_{1-6}$ alkyl, $C_{3-7}$ cycloalkyl, halo $C_{1-6}$ alkyl, heteroalkyl, optionally substituted heteroaryl, optionally substituted phenyl-$C_{1-6}$ alkyl, or optionally substituted heteroaryl-$C_{1-6}$ alkyl;

$R^{12}$ is hydrogen, $C_{1-6}$ alkyl, halo $C_{1-6}$ alkyl, heteroalkyl, optionally substituted $C_{3-7}$ cycloalkyl, optionally substituted $C_{3-7}$ cycloalkyl $C_{1-6}$ alkyl, optionally substituted phenyl, optionally substituted heteroaryl, or optionally substituted heterocyclyl; and $R^{13}$ is hydrogen, $C_{1-6}$ alkyl, heteroalkyl, optionally substituted $C_{3-7}$ cycloalkyl, optionally substituted heterocyclyl, optionally substituted aryl, or optionally substituted heteroaryl; and $R^{14}$ is hydrogen, $C_{1-6}$ alkyl or heteroalkyl; or alternatively, $R^{13}$ and $R^{14}$ taken together with the nitrogen atom to which they are attached, form an optionally substituted heterocyclyl ring;

except that [4-isobutyl-6-(2-isopropyl-phenyl)-pyridazin-3-yl]-(3-isopropyl piperazin-1-yl)- methanone and (3-benzyl-piperazin-1-yl)[4-isobutyl-6-(2-isopropyl-phenyl)-pyridazin-3-yl]-methanone are excluded from the genus of formula (I).

In another embodiment the invention provides compounds of formula (I):

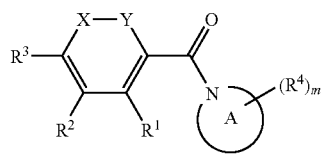

or tautomers, progdrugs, esters, or pharmaceutically acceptable salts thereof, wherein:

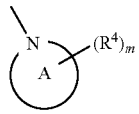

is a heterocyclyl substituted by m $R^4$ groups wherein m is 0, 1, 2, 3 or 4; and wherein said heterocyclyl is a non-aromatic mono-cyclic radical of four to eight ring atoms, in which one or two ring atoms are nitrogen atoms, with the remaining ring atoms being carbon atoms; and wherein said structure: (1) does not contain a nitrogen atom which is directly bonded to a heteroatom; and (2) contains at least one nitrogen atom not directly bonded to a carbonyl group;

X—Y is selected from the group consisting of:
  (1) N=C(NR$^{10}$R$^{11}$),
  (2) C(NR$^6$R$^7$)=N,
  (3) CR$^8$=N,
  (4) C(O)—NR$^9$,
  (5) N(O)=CR$^{12}$,
  (6) N(R$^5$)—C(O),
  (7) CR$^8$=N(O), and
  (8) N=N;

$R^1$ is selected from the group consisting of: (1) $C_{1-6}$ alkyl, (2) $C_{3-7}$ cycloalkyl, (3) $C_{2-6}$ alkenyl, (4) $C_{2-6}$ alkynyl, (5) optionally substituted $C_{3-7}$ cycloalkyl, (6) optionally substituted $C_{3-7}$ cycloalkyl $C_{1-6}$ alkyl, (7) $C_{1-6}$ alkoxy, (8) halo $C_{1-6}$ alkoxy, (9) halo $C_{1-6}$ alkyl, (10) $C_{3-7}$ cycloalkoxy, (11) heteroalkyl, (12) heteroalkoxy, (13) halogen, (14) optionally substituted phenyl which does not have nitro as a substituent, (15) optionally substituted heteroaryl, and (16) optionally substituted heterocyclyl;

$R^2$ is hydrogen, $C_{1-6}$ alkyl, $C_{1-6}$ alkoxy, halo $C_{1-6}$ alkyl, or halogen;

$R^3$ is phenyl or heteroaryl wherein said heteroaryl is an aromatic mono-cyclic radical of six ring atoms, in which one or two ring atoms are nitrogen atoms with the remaining ring atoms being carbon atoms, and wherein said phenyl or said heteroaryl are substituted by one, two or three substituents independently selected from the group consisting of $C_{1-8}$ alkyl, halo $C_{1-6}$ alkyl, $C_{1-6}$ alkoxy, halo $C_{1-6}$ alkoxy, halogen and cyano;

each $R^4$ is: (a) attached to a ring carbon atom and independently selected from the group consisting of: (1) hydrogen, (2) $C_{1-6}$ alkyl, (3) hydroxy $C_{1-6}$ alkyl or halo $C_{1-6}$ alkyl, (4) heteroalkyl, (5) $C_{2-6}$ alkenyl, (6) $C_{2-6}$ alkynyl, (7) hydroxy $C_{3-6}$ alkenyl, (8) hydroxy $C_{3-6}$ alkynyl, (9) $C_{1-6}$ alkoxy $C_{3-6}$ alkenyl, (10) $C_{1-6}$ alkoxy $C_{3-6}$ alkynyl, (11) hydroxy, (12) $C_{1-6}$ alkoxy, (13) halo $C_{1-6}$ alkoxy, (14) heteroalkoxy, (15) halogen, (16) cyano, (17) optionally substituted phenyl, (18) optionally substituted $C_{3-7}$ cycloalkyl, (19) optionally substituted $C_{3-7}$ cycloalkyl $C_{1-6}$ alkyl, (20) optionally substituted heteroaryl, (21) optionally substituted heterocyclyl, (22) optionally substituted phenyl-$C_{1-6}$ alkyl, (23) optionally substituted heteroaryl-$C_{1-6}$ alkyl, (24) optionally substituted heterocyclyl-$C_{1-6}$ alkyl, (25) nitro, (26) carboxy, (27) formyl, (28) acyl, (29) $C_{1-6}$ alkoxycarbonyl, (30) carbamoyl, (31) mono- or di-$C_{1-6}$ alkyl substituted aminocarbonyl, (32) $C_{1-6}$ alkylthio, (33) $C_{1-6}$ alkylsulfinyl, (34) $C_{1-6}$ alkylsulfonyl, and (35) amino optionally substituted by one or two substituents independently selected from the group consisting of $C_{1-6}$ alkyl, heteroalkyl, optionally substituted $C_{3-7}$ cycloalkyl and optionally substituted heterocyclyl; or (b) attached to a ring nitrogen atom and independently selected from the group consisting of: (1) hydrogen, (2) $C_{1-6}$ alkyl, (3) hydroxy $C_{1-6}$ alkyl or halo $C_{1-6}$ alkyl, (4) heteroalkyl, (5) $C_{2-6}$ alkenyl, (6) $C_{2-6}$ alkynyl, (7) hydroxy $C_{3-6}$ alkenyl, (8) hydroxy $C_{3-6}$ alkynyl, (9) $C_{1-6}$ alkoxy $C_{3-6}$ alkenyl, (10) $C_{1-6}$ alkoxy $C_{3-6}$ alkynyl, (11) optionally substituted $C_{3-7}$ cycloalkyl, (12) optionally substituted $C_{3-7}$ cycloalkyl $C_{1-6}$ alkyl, (13) optionally substituted heterocyclyl, and (14) optionally substituted heterocyclyl $C_{1-6}$ alkyl;

$R^5$ is $C_{1-6}$ alkyl, $C_{3-7}$ cycloalkyl, halo $C_{1-6}$ alkyl, or heteroalkyl;

$R^6$ and $R^{10}$ are independently of each other selected from the group consisting of: hydrogen, $C_{1-6}$ alkyl, $C_{1-6}$ alkanoyl, $C_{1-6}$ alkylsulfonyl, $C_{3-7}$ cycloalkyl, optionally substituted phenyl-$C_{1-6}$ alkyl, optionally substituted heteroaryl-$C_{1-6}$ alkyl, and optionally substituted heterocyclyl-$C_{1-6}$ alkyl;

$R^7$ and $R^{11}$ are idenpendently of each other selected from the group consisting of: hydrogen, $C_{1-6}$ alkyl, $C_{3-7}$ cycloalkyl, halo $C_{1-6}$ alkyl, $C_{1-6}$ alkanoyl, and heteroalkyl;

$R^8$ is selected from the group consisting of: (1) hydrogen, (2) hydroxy, (3) $C_{1-6}$ alkyl, (4) $C_{3-7}$ cycloalkyl, (5) $C_{2-6}$ alkenyl, (6) $C_{2-6}$ alkynyl, (7) optionally substituted $C_{3-7}$ cycloalkyl, (8) optionally substituted $C_{3-7}$ cycloalkyl $C_{1-6}$ alkyl, (9) $C_{1-6}$ alkoxy, (10) halo $C_{1-6}$ alkoxy, (11) halo $C_{1-6}$ alkyl, (12) $C_{3-7}$ cycloalkoxy, (13) heteroalkyl, (14) heteroalkoxy, (15) halogen, (16) optionally substituted phenyl, (17) optionally substituted heteroaryl, and (18) optionally substituted heterocyclyl;

$R^9$ is hydrogen, $C_{1-6}$ alkyl, $C_{3-7}$ cycloalkyl, halo $C_{1-6}$ alkyl, and heteroalkyl; and $R^{12}$ is hydrogen, $C_{1-6}$ alkyl, halo $C_{1-6}$ alkyl, heteroalkyl, optionally substituted $C_{3-7}$ cycloalkyl, optionally substituted $C_{3-7}$ cycloalkyl $C_{1-6}$ alkyl, optionally substituted phenyl, optionally substituted heteroaryl, or optionally substituted heterocyclyl; except that [4-isobutyl-6-(2-isopropylphenyl)-pyridazin-3-yl]-(3-isopropyl piperazin-1-yl)-methanone and (3-benzyl-piperazin-1-yl)44-isobutyl-6-(2-isopropyl-phenyl)-pyridazin-3-yl]-methanone are excluded from the genus of formula (I).

While the broadest definition of this invention is described before, certain compounds of formula (I) are preferred.

i) In the compounds of formula (I), X—Y is $C(NR^6R^7)=N$, $CR^8=N$ or $C(O)—NR^9$, preferably X—Y is $C(NH_2)=N$, $CH=N$, $C(Cl)=N$, $C(O)—NH$, $C(pyridinyl)=N$, $C(triazolyl)=N$, $C(NH((CH_2)_2OH))=N$, $C(NH_2-pyrimidinyl)=N$, $C(CH_2OH)=N$, $C(pyrazinyl)=N$, $C(C(O)NH(pyridinyl))=N$ or $C(O)—N(CH_3)$, more preferably $C(NH_2)=N$, $C(NH_2-pyrimidinyl)=N$, $C(pyrazinyl)=N$, $CH=N$, $C(triazolyl)=N$ $C(Cl)=N$ or $C(O)—NH$, and most preferably X—Y is $C(NH_2)=N$, $C(NH_2-pyrimidinyl)=N$, $C(pyrazinyl)=N$, $C(triazolyl)=N$ or $C(O)—NH$.

ii) In the compounds of formula (I), $R^{10}$ and $R^{11}$ are preferably hydrogen, when X—Y is $N=C(NR^{10}R^{11})$.

iii) In the compounds of formula (I), $R^6$ is preferably hydrogen, $C_{1-6}$ alkanoyl, optionally substituted phenyl-$C_{1-6}$ alkyl or $C_{1-6}$ alkylsulfonyl and $R^7$ is hydrogen, $C_{1-6}$ alkanoyl, amino-$C_{1-6}$alkyl- or hydroxy-$C_{1-6}$alkyl-, when X—Y is $C(NR^6R^7)=N$. More preferably $R^6$ and $R^7$ are hydrogen or hydrogen and hydroxyethyl, respectively. Most preferably $R^6$ and $R^7$ are hydrogen.

iv) In the compounds of formula (I), $R^8$ is preferably hydrogen, halogen, mercapto, $C_{2-6}$ alkynyl, $C_{1-6}$ alkoxy, heteroalkyl, heteroalkoxy, cyano, optionally substituted pyridinyl, optionally substituted pyrimdinyl, optionally substituted triazolyl, optionally substituted pyrazolyl, optionally substituted pyrazinyl, $C_{1-6}$ alkoxy-carbonyl, carboxy or $—CONR^{13}R^{14}$, wherein $R^{13}$ and $R^{14}$ are defined herein, more preferebly, $R^8$ is hydrogen, halogen or $C_{1-6}$ alkoxy and $R^8$ is most preferably chlorine, pyridin-3-yl, [1,2,4]triazol-1-yl, 2-amino-pyrimidin-5-yl or pyrazin-2-yl when X—Y is $CR^8=N$.

v) In the compounds of formula (I), $R^5$ is preferably $C_{1-6}$ alkyl and $R^5$ is more preferably methyl, when X—Y is $N(R^5)—C(O)$.

vi) In the compounds of formula (I), $R^8$ is preferably hydrogen, when X—Y is $CR^8=N(O)$.

vii) In the compounds of formula (I),

is preferably piperidin-1-yl or [1,4]diazepan-1-yl, and more preferably piperidin-1-yl.

viii) In the compounds of formula (I), m is preferably 1.

ix) In the compounds of formula (I), $R^4$ is preferably optionally substituted heterocyclyl or heteroalkyl, more preferably, $R^4$ is hydroxy $C_{1-6}$ alkyl, optionally substituted pyrrolidin-1-yl or optionally substituted piperidin-1-yl, and more preferably $R^4$ is piperidin-1-yl or pyrrolidin-1-yl, said piperidin-1-yl and pyrrolidin-1-yl being optionally substituted by hydroxyl $C_{1-6}$ alkyl or hydroxy. $R^4$ is especially preferably pyrrolidin-1-yl, 2-hydroxymethyl-pyrrolidin-1-yl or 4-hydroxy-piperidin-1-yl.

x) In the compounds of formula (I), $R^4$ is pyrrolidin-1-yl, 2-hydroxymethyl-pyrrolidin-1-yl or 4-hydroxy-piperidin-1-yl.

xi) In the compounds of formula (I),

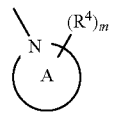

is preferably 4-pyrrolidin-1-yl-piperidin-1-yl, 4-(2-hydroxymethyl-pyrrolidin-1-yl)-piperidin-1-yl or 4-hydroxy-[1,4']bipiperidinyl-1'-yl.

xii) In the compounds of formula (I), $R^1$ is $C_{1-6}$ alkyl, halogen or optionally substituted phenyl, preferably $C_{1-6}$ alkyl, especially methyl. In the compounds of formula (I), $R^2$ is preferably hydrogen or halogen, especially hydrogen.

xiii) In the compounds of formula (I), $R^3$ is preferably phenyl or pyridyl, said phenyl and pyridyl being optionally substituted by one or two substituents independently selected from the group consisting of trifluoromethyl and trifluoromethoxy. $R^3$ is more preferably 3-trifluoromethyl phenyl.

xiv) in the compounds of formula (I) $R^{13}$ is preferably hydrogen, $C_{1-6}$ alkyl, heteroalkyl, pyridinyl, optionally substituted piperidinyl, optionally substituted piperazinyl and more preferably $R^{13}$ is hydrogen, methyl, hydroxyethyl, 1-carboxylic acid-t-butyl ester-piperidin-4-yl, pyridin-3yl, 1-carboxylic acid-t-butyl ester-piperazin-4-yl, piperidin-4-yl or piperazin-4-yl, and most preferably $R^{13}$ is pyridin-3yl. In the compounds of formula (I), $R^{14}$ is preferably hydrogen.

xv) A preferred compound of the invention is a compound of formula (I), which is [3-Methyl-5-(3-trifluoromethyl-phenyl)-pyridin-2-yl]-(4-pyrrolidin-1-yl-piperidin-1-yl)-methanone, [6-Chloro-3-methyl-5-(3-trifluoromethyl-phenyl)-pyridin-2-yl]-(4-pyrrolidin-1-yl-piperidin-1-yl)-methanone, [4-((S)-2-Hydroxymethyl-pyrrolidin-1-yl)-piperidin-1-yl]-[3-methyl-5-(3-trifluoromethyl-phenyl)-pyridin-2-yl]-methanone, [6-Hydroxy-3-methyl-5-(3-trifluoromethyl-phenyl)-pyridin-2-yl]-(4-pyrrolidin-1-yl-piperidin-1-yl)-methanone or its tautomeric form 5-Methyl-6-(4-pyrrolidin-1-yl-piperidine-1-carbonyl)-3-(3-trifluoromethyl-phenyl)-1H-pyridin-2-one, [6-Amino-3-methyl-5-(3-trifluoromethyl-phenyl)-pyridin-2-yl]-(4-pyrrolidin-1-yl-piperidin-1-yl)-methanone, [5-Methyl-3-(3-trifluoromethyl-phenyl)-[2,3']bipyridinyl-6-yl]-(4-pyrrolidin-1-yl-piperidin-1-yl)-methanone, [3-Chloro-6-hydroxy-5-(3-trifluoromethyl-phenyl)-pyridin-2-yl]-(4-pyrrolidin-1-yl-piperidin-1-yl)-methanone or its tautomeric form 5-Chloro-6-(4-pyrrolidin-1-yl-piperidine-1-carbonyl)-3-(3-trifluoromethyl-phenyl)-1H-pyridin-2-one, [3-Methyl-6-[1,2,4]triazol-1-yl-5-(3-trifluoromethyl-phenyl)-pyridin-2-yl]-(4-pyrrolidin-1-yl-piperidin-1-yl)-methanone, [6-(2-Hydroxy-ethylamino)-3-methyl-5-(3-trifluoromethyl-phenyl)-pyridin-2-yl]-(4-pyrrolidin-1-yl-piperidin-1-yl)-methanone, [5-(2-Fluoro-5-trifluoromethyl-phenyl)-3-methyl-pyridin-2-yl]-(4-pyrrolidin-1-yl-piperidin-1-yl)-methanone, [3-Methyl-6-(1H-[1,2,3]triazol-4-yl)-5-(3-trifluoromethyl-phenyl)-pyridin-2-yl]-(4-pyrrolidin-1-yl-piperidin-1-yl)-methanone, [5-(2-Methoxy-5-trifluoromethyl-phenyl)-3-methyl-pyridin-2-yl]-(4-pyrrolidin-1-yl-piperidin-1-yl)-methanone, [6-(2-Amino-pyrimidin-5-yl)-3-methyl-5-(3-trifluoromethyl-phenyl)-pyridin-2-yl]-(4-pyrrolidin-1-yl-piperidin-1-yl)-methanone, [6-Hydroxymethyl-3-methyl-5-(3-trifluoromethyl-phenyl)-pyridin-2-yl]-(4-pyrrolidin-1-yl-piperidin-1-yl)-methanone, [3-Methyl-6-pyrazin-2-yl-5-(3-trifluoromethyl-phenyl)-pyridin-2-yl]-(4-pyrrolidin-1-yl-piperidin-1-yl)-methanone, 5-Methyl-6-(4-pyrrolidin-1-yl-piperidine-1-carbonyl)-3-(3-trifluoromethyl-phenyl)-pyridine-2-carboxylic acid pyridin-3-ylamide, or 1,5-Dimethyl-6-(4-pyrrolidin-1-yl-piperidine-1-carbonyl)-3-(3-trifluoromethyl-phenyl)-1H-pyridin-2-one.

In a further embodiment the invention provides a compound of formula (I):

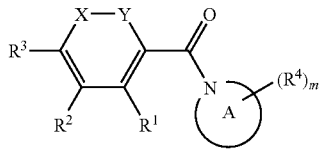

or tautomers, progdrugs, esters, or pharmaceutically acceptable salts thereof, wherein:
X—Y is N=C(NR$^{10}$R$^{11}$), C(NR$^6$R$^7$)=N, CR$^8$=N, C(O)—NR$^9$, N(R$^5$)—C(O), CR$^8$=N(O) or

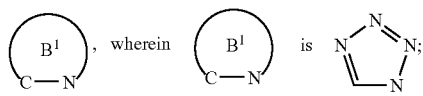

R$^1$ is C$_{1-6}$ alkyl, halogen or optionally substituted phenyl, provided that optionally substituted phenyl does not have nitro as a substituent;
R$^2$ is hydrogen or halogen;
R$^3$ is phenyl substituted by one, two or three substituents independently selected from the group consisting of halo C$_{1-6}$ alkyl, C$_{1-6}$ alkoxy and halogen;
R$^4$ is, when attached to a ring carbon atom, optionally substituted azetidinyl, pyrrolidinyl, piperidinyl or azepanyl, most preferably pyrrolidinyl;
m is 1;

is piperidinyl;
R$^5$ is C$_{1-6}$ alkyl;
R$^6$ and R$^{10}$ are independently hydrogen, C$_{1-6}$ alkanoyl, C$_{1-6}$ alkylsulfonyl or optionally substituted phenyl-C$_{1-6}$ alkyl;
R$^7$ and R$^{11}$ are independently hydrogen, C$_{1-6}$ alkanoyl or heteroalkyl;
R$^8$ is hydrogen, mercapto, C$_{2-6}$ alkynyl, C$_{1-6}$ alkoxy, heteroalkyl, heteroalkoxy, halogen, cyano, optionally substituted pyridinyl, optionally substituted pyrimdinyl, optionally substituted triazolyl, optionally substituted pyrazolyl, optionally substituted pyrazinyl, C$_{1-6}$ alkoxy-carbonyl, carboxy or —CONR$^{13}$R$^{14}$;
R$^9$ is hydrogen or C$_{1-6}$ alkyl; and
R$^{13}$ is hydrogen, C$_{1-6}$ alkyl, hydroxyethyl, pyridinyl, optionally substituted piperidinyl, optionally substituted piperazinyl; and R$^{14}$ is hydrogen; or R$^{13}$ and R$^{14}$ taken together with the nitrogen atom to which they are attached, form piperazinyl.

General Synthetic Procedures

The compounds of formula (I) can be manufactured by methods known in the art, by the methods given below, by the methods given in the examples or by analogous methods. Appropriate reaction conditions for the individual reaction steps are known to a person skilled in the art. Starting materials are either commercially available or are known or can be prepared by methods given below or by methods described in the examples, or by methods known in the art.

The syntheses of the compounds of general formula (I) are described in Scheme 1 to Scheme 9.

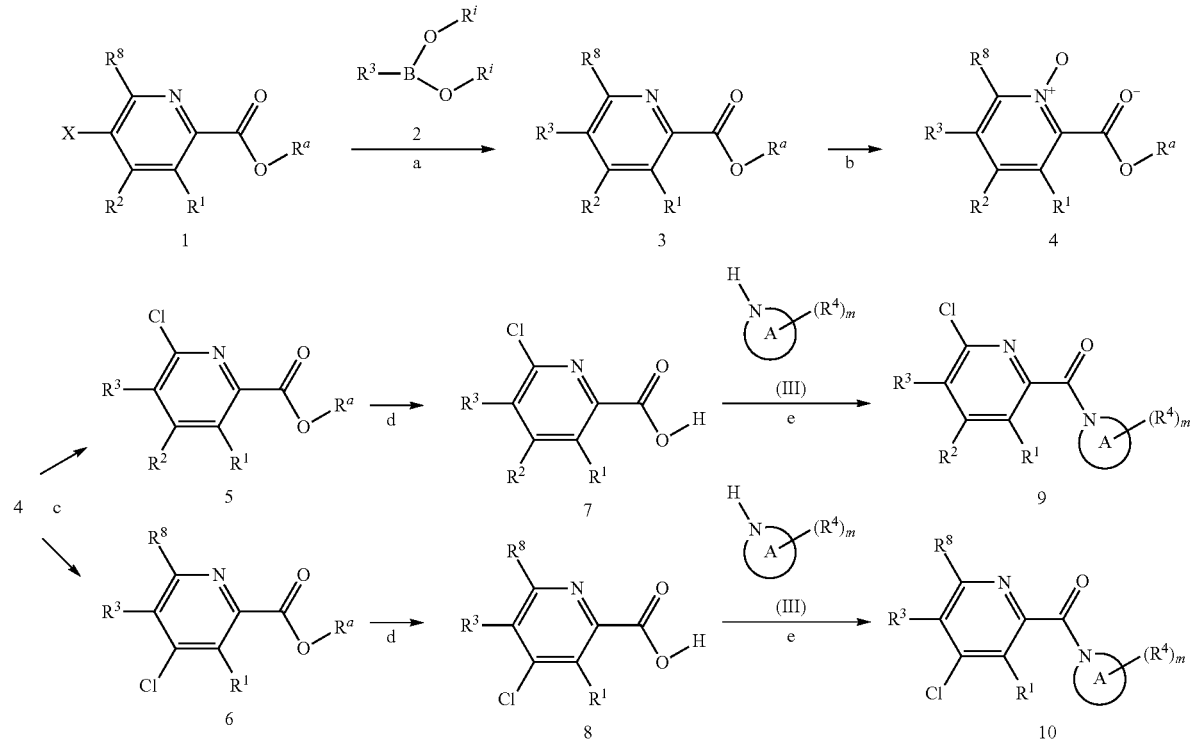

Scheme 1

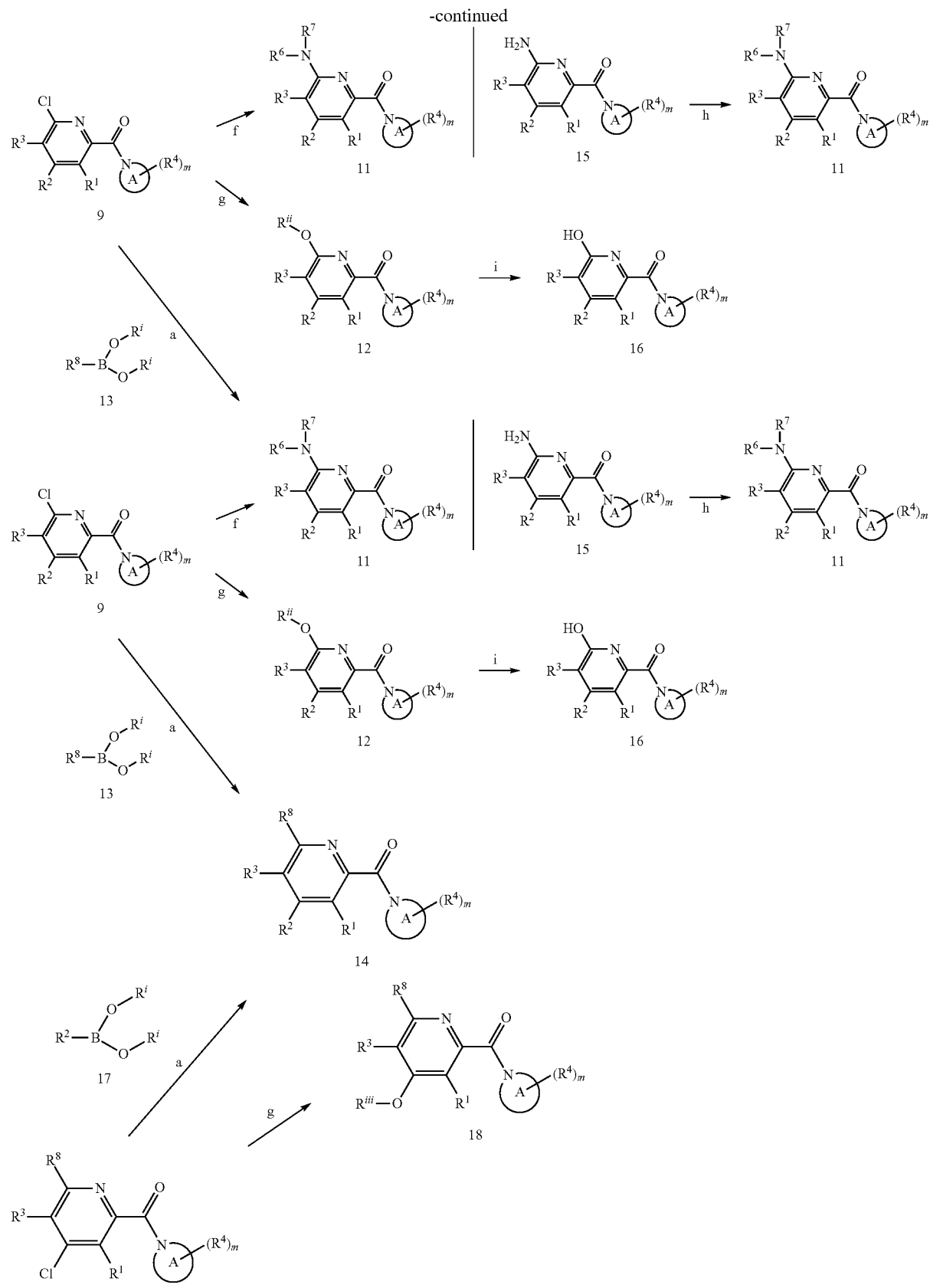

(In Scheme 1,

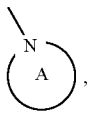

$R^1$, $R^2$, $R^3$, $R^4$, $R^6$, $R^7$, $R^8$ and m are defined as described before. $R^a$ is $C_{1-6}$ alkyl. $R^i$ is independently hydrogen or $C_{1-6}$ alkyl, or both $R^i$s together form a $C_{1-6}$ alkylene group. $R^{ii}$ is $C_{1-6}$ alkyl, halo $C_{1-6}$ alkyl, $C_{3-7}$ cycloalkyl, heteroalkyl, said heteroalkyl optionally carrying a protective function which can be removed subsequently, aryl, heteroaryl, optionally substituted phenyl-$C_{1-6}$ alkyl or optionally substituted heteroaryl-$C_{1-6}$ alkyl. $R^{iii}$ is $C_{1-6}$ alkyl and X is halogen or trifluoromethylsulfonyloxy)

Halo pyridine esters 1 are commercially available, are known or can be prepared by methods known in the art. Suzuki couplings, the reaction with aryl or heteroaryl boronic acids or esters 2 in the presence of a catalyst, such as tetrakis-(triphenylphosphine)-palladium or dichloro[1,1'-bis(diphenylphosphino)ferrocene]palladium(II) optionally in the form of a dichloromethane complex (1:1), and in the presence of a base, such as potassium phosphate, or sodium or potassium carbonate, in a solvent, such as toluene, dioxane, tetrahydrofuran or N,N-dimethylformamide and in an inert atmosphere such as argon or nitrogen, in a temperature range preferably between room temperature and about 130° C. can be applied to transform halo pyridine esters 1 into aryl pyridine esters 3 (step a). Oxidation of aryl pyridine esters 3 with meta-chloroperbenzoic acid preferably in dichloromethane at room temperature or with hydrogen peroxide urea adduct and trifluoroacetic anhydride in dichloromethane or acetonitrile between 0° C. and room temperature gives N-oxides 4 (step b). Treatment of N-oxides 4 with phosphorus oxychloride preferably between about 50° C. and about 100° C. gives chloro-pyridine esters 5 and/or 6, provided $R^8$ and/or $R^2$ are hydrogen (step c). Chloro pyridine esters 5 and 6 can be saponified, e.g. by treatment with lithium or potassium hydroxide in a solvent like tetrahydrofuran, ethanol or 2-ethoxy-ethanol and mixtures thereof in a temperature range between room temperature and about 150° C. to give acids 7 and 8 (step d). Aryl pyridine acids 7 and 8 can then be coupled with secondary amines (III) to aryl pyridine amides 9 and 10 i) by transformation of the aryl pyridine acids 7 and 8 into the corresponding acid chlorides, preferably by reaction with oxalyl chloride and a catalytic amount of N,N-dimethylformamide and optionally using dichloromethane as co-solvent followed by evaporation and reaction of the acid chlorides with secondary amines (III) in a solvent like dichloromethane or N,N-dimethylformamide in the presence of a base like triethylamine preferably between 0° C. and room temperature or ii) by suitable amide coupling reactions, such as using of O-(7-azabenzotriazol-1-yl)-1,1,3,3-tetramethyluronium hexafluorophosphate (HATU), triethylamine, in N,N-dimethylformamide preferably between 0° C. and room temperature (step e). Aryl amino-pyridine amides 11 can be prepared from aryl chloro-pyridine amides 9 by reaction with a primary or secondary amine in an inert atmosphere such as argon or nitrogen in the presence of a palladium catalyst such as tris (dibenzylideneacetone)dipalladium(0) ($Pd_2(dba)_3$) or palladium(II) acetate ($Pd(COOCH_3)_2$), a phosphine ligand like triphenylphosphine, rac-2,2'-bis(diphenylphosphino)-1,1'-binaphthalene (rac-BINAP) or (R)-(−)-1-[(S)-2-(dicyclohexylphosphino)ferrocenyl]ethyldi-tert-butylphosphine and a base such as $Cs_2CO_3$ or KOtert-Bu in a solvent like toluene, ethanol or water or mixtures thereof preferably in a temperature range between about 50° C. and the reflux temperature of the solvents (step f). Aryl amino-pyridine amides 15 ($R^6$, $R^7$ equal hydrogen), prepared from the analogous amino-pyridine amides 11 ($R^6$ and/or $R^7$ equal a suitable protective function; for protecting groups and their use in synthesis see *Protective Groups in Organic Synthesis*, T. W. Greene and P. G. M. Wuts, $3^{rd}$ Edition, 1999, Wiley-Interscience) can be converted into the corresponding mono- or bis-alkanoyl amino derivatives 11, e.g. by reaction with an acid anhydride in the presence of a base such as trietylamine in a solvent like acetone preferably at reflux, or into the corresponding alkanesulfonyl amino derivatives 11, by reaction with an alkanesulfonyl chloride in the presence of a base such as trietylamine, a catalyst such as 4-(N,N-dimethyl)-aminopyidine in a solvent like N,N-dimethylformamide at a temperature around 50° C. and subsequent treatment with a tetrabutylammonium fluoride solution in tetrahydrofuran at reflux to cleave potentially formed bis-sulfonamides into a mono-sulfonamides 11 (step h). Reaction of aryl chloro-pyridine amides 9 and 10 with a sodium or potassium alcoholate in the corresponding alcohol as solvent or in a solvent like tetrahydrofuran preferably at reflux gives aryl alkoxy-pyridine amides 12 and 18 (steps g). Treatment of aryl methoxy-pyridine amides 12 with boron tribromide in dichloromethane preferable between 0° C. and room temperature gives aryl hydroxy-pyridine amides 16 (step i). Suzuki reactions, as described for the transformation of halo pyridine esters 1 can be used to convert aryl chloro-pyridine amides 9 and 10 into aryl pyridine amides 14 (steps a).). Reaction of aryl chloro-pyridine amides 9 with heteroaromatic compounds carrying an acidic hydrogen atom like 1H-[1,2,4] triazole, 1H-tetrazole, pyridin-2-ol, pyridin-3-ol or pyridin-4-ol in the presence of a base like sodium hydride in a solvent like 1-methyl-pyrrolidin-2-one preferably at elevated temperature in a range between about 100° C. and about 170° C. gives aryl pyridine amides 14 with $R^8$ equal to an N-linked heteroaryl or an O-linked heteroaryloxy moiety (steps k). Reaction of aryl chloro-pyridine amides 9 and 10 with sodium or potassium cyanide in a solvent like 1-methyl-pyrrolidin-2-one preferably at elevated temperature in a range between about 100° C. and about 170° C. gives aryl pyridine amides 14 with $R^8$ or $R^2$ equal to CN (steps k). Reaction of aryl chloro-pyridine amides 9 with sodium azide in a solvent like N,N-dimethylformamide preferably at reflux gives tetrazolo-pyridines 19 (step l). Reaction of aryl chloro-pyridine amides 9 with an alkyl sulfide or a hydrogen sulfide in a solvent like N,N-dimethylformamide preferably at temperatures between about 60° C. and reflux gives mercapto-pyridines 20 (step m).

Scheme 2

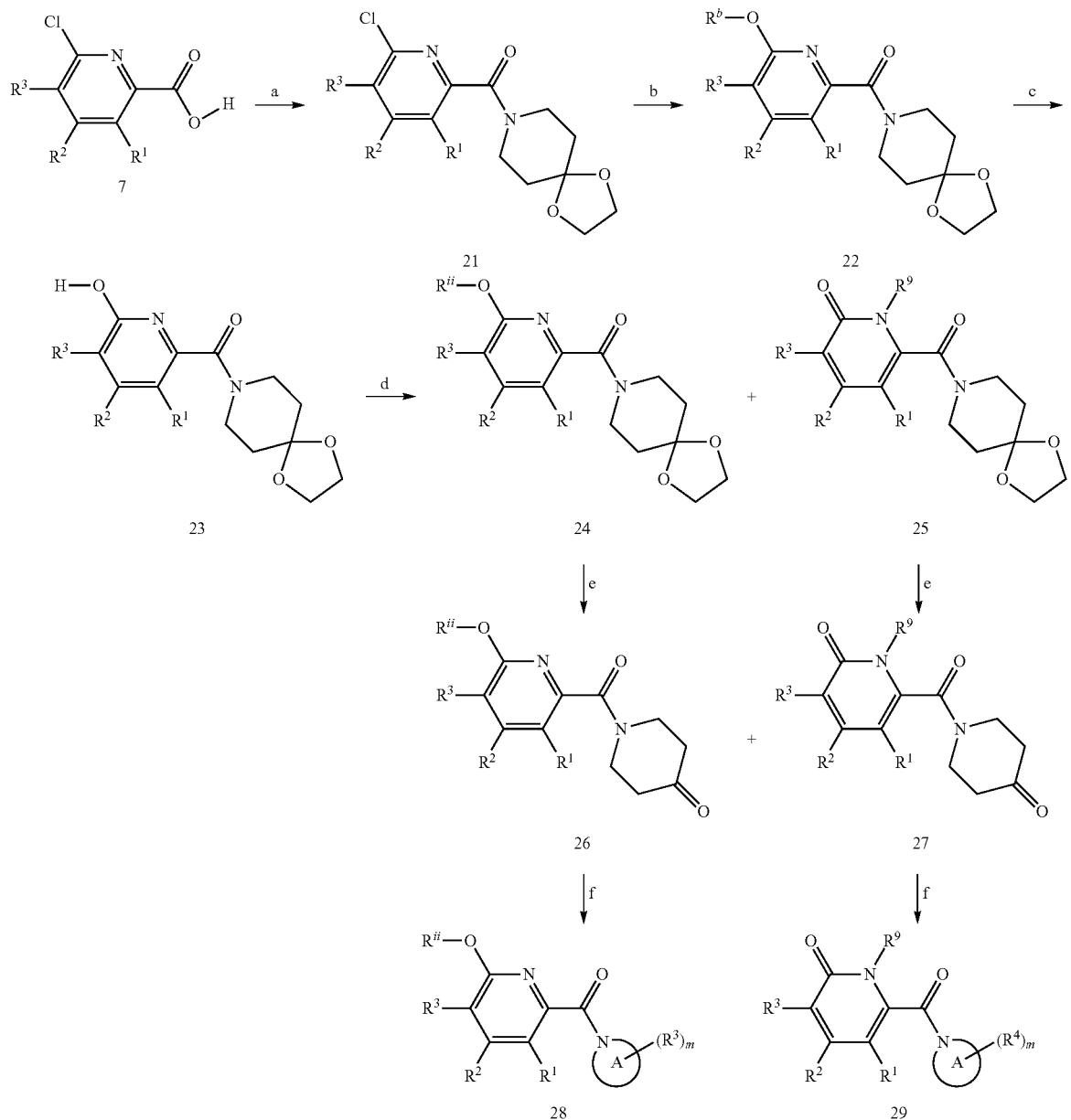

(In Scheme 2,

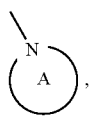

$R^1$, $R^2$, $R^3$, $R^4$, $R^9$ and m are defined as described before. $R^{ii}$ is $C_{1-6}$ alkyl, halo $C_{1-6}$ alkyl, $C_{3-7}$ cycloalkyl, optionally substituted heteroaryl, optionally substituted phenyl-$C_{1-6}$ alkyl or optionally substituted heteroaryl-$C_{1-6}$ alkyl or heteroalkyl, said heteroalkyl optionally carrying a protective function which can be removed subsequently. $R^b$ is phenyl-methyl).

Coupling of aryl chloro-pyridine acids 7 with a suitably protected piperidine e.g. using HATU as described for steps e, Scheme 1, gives chloro-pyridine-piperdine amides 21 (step a). Treatment of chloro-pyridine-piperdine amides 21 with a suitable alcoholate as described for steps g, Scheme 1, results in alkoxy-pyridine-piperdine amides 22 (step b). Alkoxy-pyridine-piperdine amides 22 with $R^b$ being an optionally substituted phenyl-methyl moiety suitable as protective group can then be converted into hydroxy-pyridine-piperdine amides 23 by standard protocols for removal such protective functions (step c). Alkylation of hydroxy-pyridine-piperdine amides 23 with a suitable alkyl or aryl halide in the presence of a base like cesium or potassium carbonate in a solvent like acetonitrile, N,N-dimethylformamide, 1-methyl-pyrrolidin-2-one or tetrahydrofuran at temperatures between room temperature and the reflux temperature of the solvents gives mixtures of O- and N-alkylated or arylated pyridine-piperdine amides 24 and 25 (step d). Removal of the acetal protective function in pyridine-piperdine amides 24 and 25 under acidic conditions as described in *Protective Groups in Organic Synthesis*, T. W. Greene and P. G. M. Wuts, 3$^{rd}$ Edition, 1999, Wiley-Interscience, gives ketones 26 and 27 (steps e). Reductive amination with suitable primary or secondary amines transforms ketones 26 and 27 into aryl-alkoxy-pyridine amides 28 and aryl-pyridone-amides 29 under conditions as described for step a in Scheme 6 (steps f).

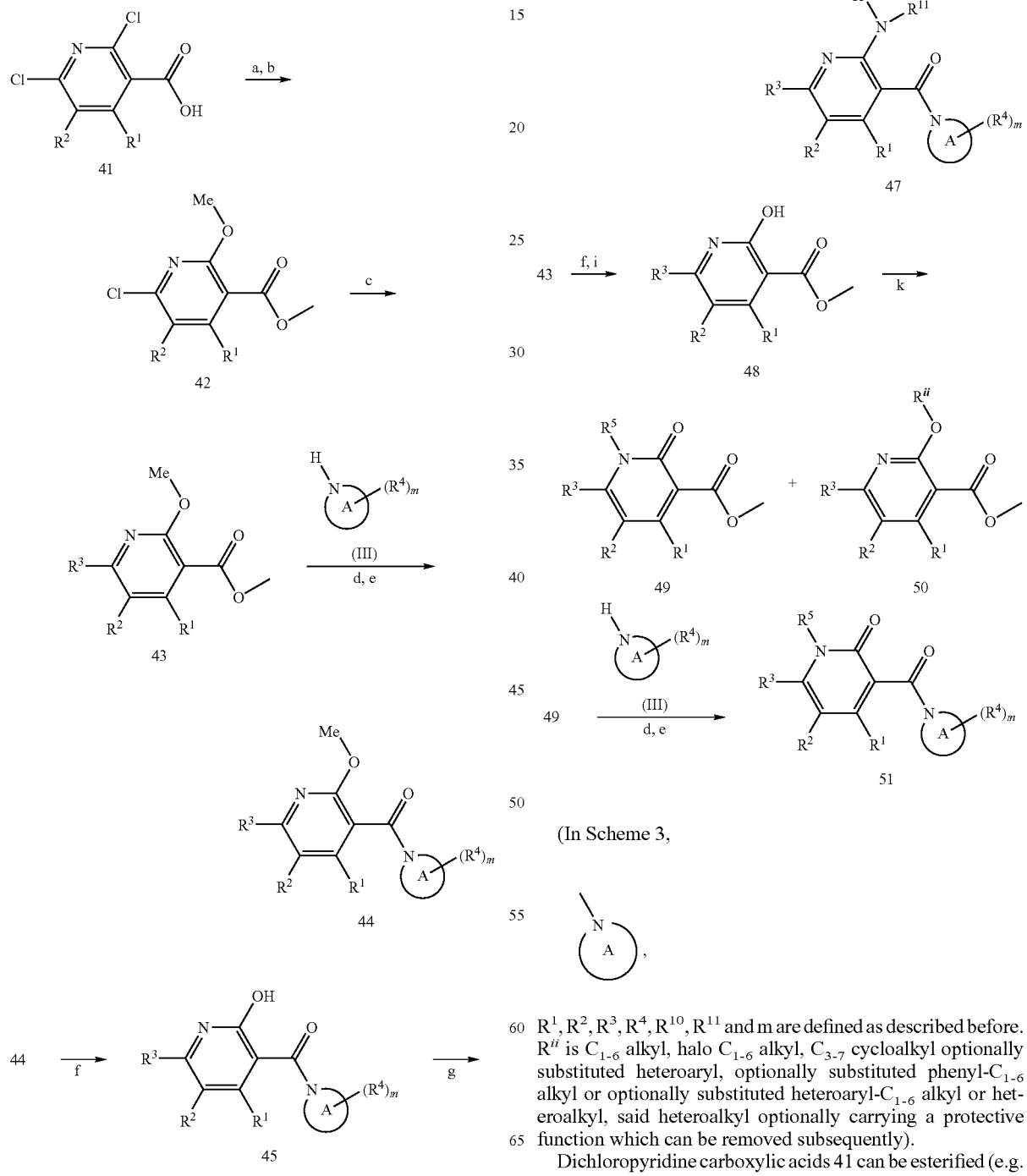

(In Scheme 3, $R^1, R^2, R^3, R^4, R^{10}, R^{11}$ and m are defined as described before. $R^{ii}$ is $C_{1-6}$ alkyl, halo $C_{1-6}$ alkyl, $C_{3-7}$ cycloalkyl optionally substituted heteroaryl, optionally substituted phenyl-$C_{1-6}$ alkyl or optionally substituted heteroaryl-$C_{1-6}$ alkyl or heteroalkyl, said heteroalkyl optionally carrying a protective function which can be removed subsequently).

Dichloropyridine carboxylic acids 41 can be esterified (e.g. using iodomethane, potassium carbonate in N,N-dimethylformamide preferably at room temperature) and then reacted with sodium methoxide in dichloromethane preferably between 0° C. and room temperature to give 6-chloro-2-methoxy-nicotinic acid methyl esters 42 (steps a, b). Suzuki reactions as described for step a) in Scheme 1 transform 6-chloro-2-methoxy-nicotinic acid methyl esters 42 into methoxy-bi-aryl esters 43 (step c). Subsequent saponification (treatment with lithium or potassium hydroxide in a solvent like ethanol, methanol, tetrahydrofuran or 2-ethoxy-ethanol and mixtures thereof in a temperature range between room temperature and about 150° C.) and coupling with amines (III) gives methoxy-pyridine amides 44 using procedures similar to those described for step e, Scheme 1 (steps d, e). Treatment of methoxy-pyridine amides 44 with boron tribromide in dichloromethane preferable between 0° C. and room temperature gives hydroxy-pyridine amides 45 (step f); similar treatment of methoxy-bi-aryl esters 43 followed by re-esterification (e.g. using methanol, sulfuric acid at reflux) gives esters 48 (steps f, i). Hydroxy-pyridine amides 45 can be converted into trifluoromethanesulfonates 46 (trifluoromethane sulfonic anhydride and N-ethyldiisopropylamine in a solvent like dichloromethane preferably in a temperature range between −50° C. and room temperature, step g). Treatment of trifluoromethanesulfonates 46 with primary or secondary amines under conditions as described for step f, Scheme 1, gives aryl amino-pyridine-amides 47 (step h). Alkylation of hydroxy-pyridine esters 48 with a suitable alkyl halide in the presence of a base like cesium or potassium carbonate in a solvent like acetonitrile, N,N-dimethylformamide or tetrahydrofuran gives pyridone esters 49 and alkoxy pyridine esters 50 (step k). Saponification of esters 49 (treatment with lithium or potassium hydroxide in a solvent like ethanol, methanol, tetrahydrofuran or 2-ethoxy-ethanol and mixtures thereof in a temperature range between room temperature and about 150° C.) and coupling with amines (III) using procedures similar to those described for step e, Scheme 1, gives aryl-pyridone amides 51 (steps d, e). Reaction of trifluoromethanesulfonates 46 with sodium azide in a solvent like N,N-dimethylformamide in a temperature range between RT and reflux gives tetrazolo-pyridines 52 (step l).

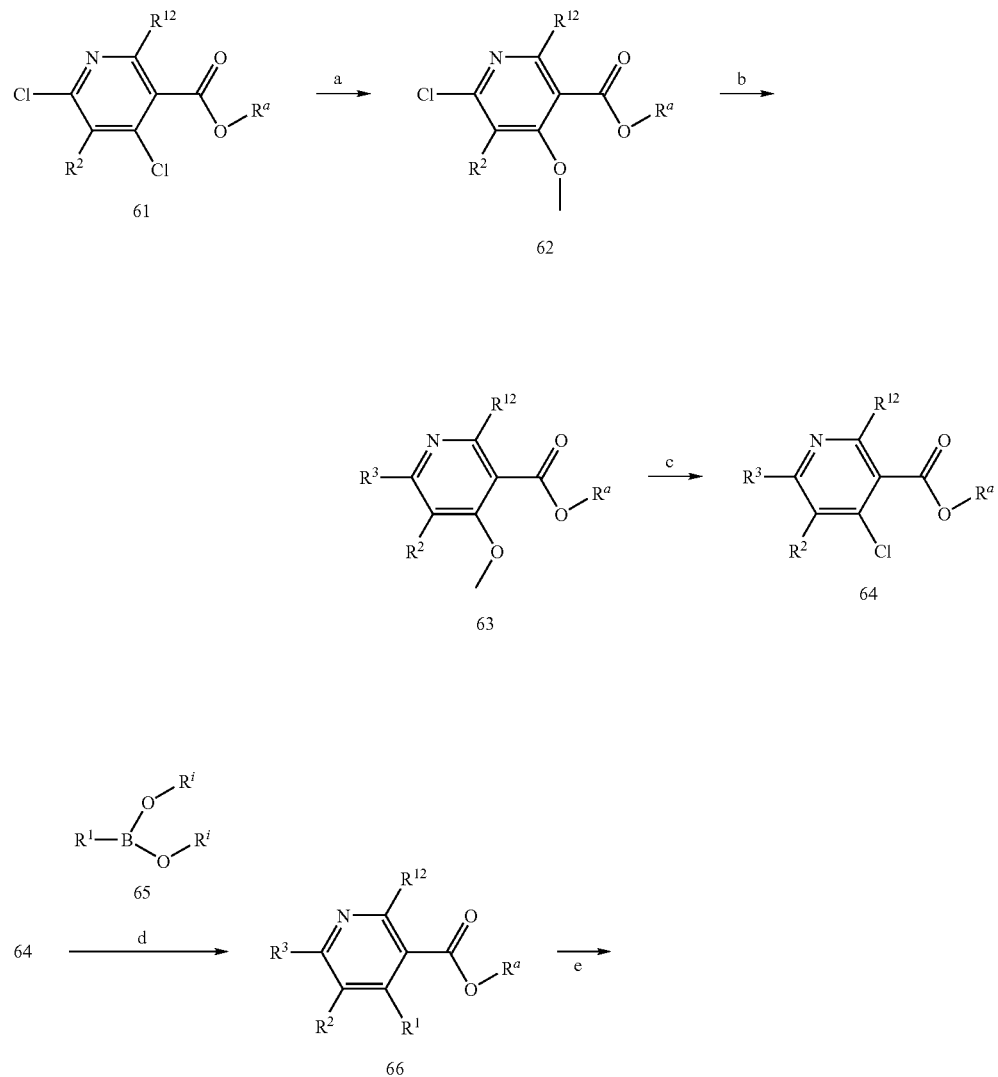

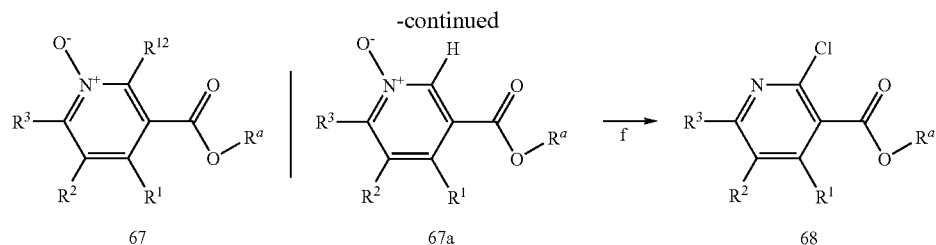

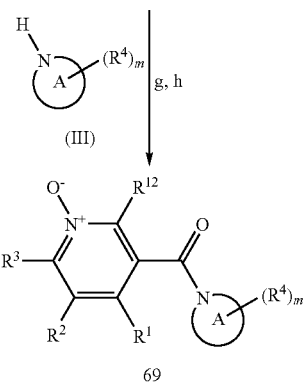

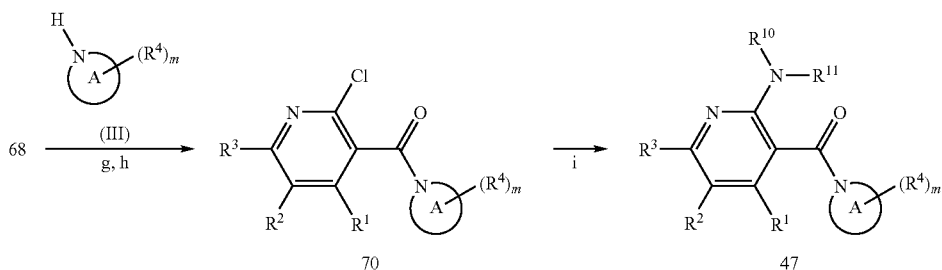

(In Scheme 4,

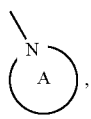

$R^1$, $R^2$, $R^3$, $R^{10}$, $R^{11}$, $R^{12}$ and m are defined as described before. $R^a$ is $C_{1-6}$ alkyl. $R^i$ is independently hydrogen or $C_{1-6}$ alkyl, or both $R^i$s together form a $C_{1-6}$ alkylene group.)

Alkyl dichloropyridine carboxylates 61 (Scheme 4) undergo selective substitution of the chloro atom ortho to the ester function when treated with sodium methylate in a solvent like tetrahydrofuran preferably around room temperature [Hutchison, A.; Y., Jun; L., K.; Maynard, G.; Chenard, B. L.; Liu, N.; Guo, Q.; Guo, Z.; Hrnciar, P. PCT Int. Appl. (2004), WO2004043925A2](step a). Suzuki reactions as described for step a) in Scheme 1 transform chloro-methoxy-pyridine carboxylates 62 into methoxy-bi-aryl esters 63 (step b). Treatment of methoxy-bi-aryl esters 63 with phosphorus oxychloride and N,N-dimethylformamide preferably at a temperature around 80° C. gives chloro-bi-aryl esters 64 [Hutchison, A.; Y., Jun; L., K.; Maynard, G.; Chenard, B. L.; Liu, N.; Guo, Q.; Guo, Z.; Hrnciar, P. PCT Int. Appl (2004), WO2004043925A2](step c). Chloro-bi-aryl esters 64 can undergo Suzuki reactions as described for step a) in Scheme 1 with boronic acids or esters 65 to give substituted bi-aryl esters 66 (step d). Oxidation of pyridine esters 66 with meta-chloro-perbenzoic acid preferably in dichloromethane at room temperature or with hydrogen peroxide urea adduct and trifluoroacetic anhydride in dichloromethane or acetonitrile between 0° C. and room temperature gives N-oxide esters 67 (step e). Treatment of N-oxide esters 67a with phosphorus oxychloride preferably between about 50° C. and about 100° C. gives chloro-pyridine esters 68 (step f). N-oxide esters 67 or chloro pyridine esters 68 can be saponified and coupled with amines (III) as described for steps d and e, Scheme 1, (steps g, h) to give N-oxide amides 69 or chloro pyridine amides 70. Treatment of chloro-pyridine amides 70 with primary or secondary amines under conditions as described for step f, Scheme 1, gives aryl amino-pyridine-amides 47 (step i).

Scheme 5

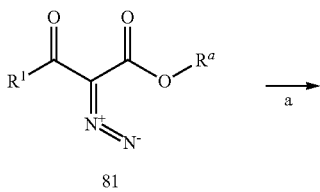

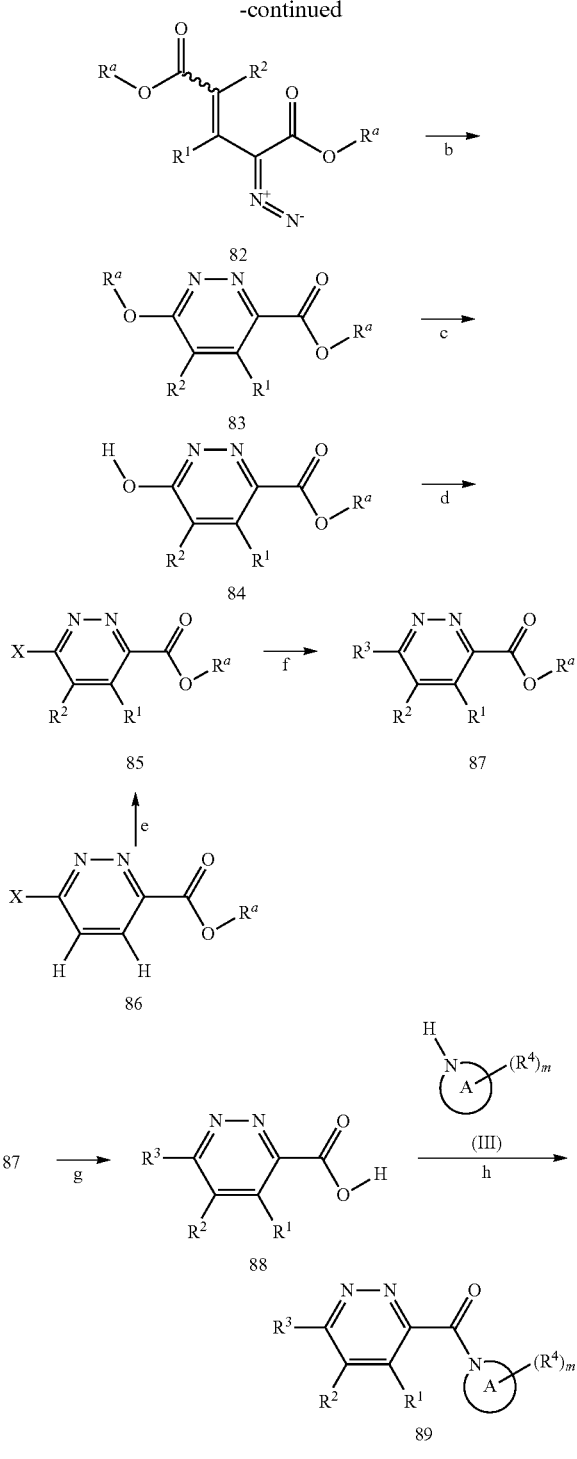

(In Scheme 5,

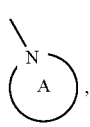, $R^1$, $R^2$, $R^3$, $R^4$, and m are defined as described before, $R^a$ is $C_{1-6}$ alkyl, X is halogen or trifluoromethylsulfonyloxy.)

Diazo-beta keto esters 81 are known or can be prepared by methods known in the art, compare Guillaume, M.; Janousek, Z.; Viehe, H. G.; Wynants, C.; Declercq, J.-P.; Tinant, B. *Journal of Fluorine Chemistry* (1994), 69(3), 253-6. Diazo-beta keto esters 81 react with suitable (triphenyl-phosphanylidene)-acetic acid esters in solvents like ether or with trialkyl phosphonoacetates, in the presence of a base like triethylamine and optionally lithium chloride in a solvent like acetonitrile preferably at room temperature to give diazo adducts 82 (step a). Subsequent treatment with triphenylphosphine in ether around room temperature converts diazo adducts 82 into pyridazine esters 83 [Guillaume, M.; Janousek, Z.; Viehe, H. G. New trifluoromethylated pyridazines by reductive cyclization of vinyldiazomethanes bearing a carbonyl group. *Synthesis* (1995), (8), 920-2](step b). Treatment of pyridazine esters 83 with boron tribromide in dichloromethane preferably between 0° C. and room temperature removes the ether and hydrolyzes the ester function; subsequent re-esterification using sulfuric or hydrochloric acid in the corresponding alcohol gives hydroxy-pyridazine esters 84 (step c). Hydroxy-pyridazine esters 84 can be converted into the corresponding chloro-pyridazine esters 85 by reaction with phosphorus oxychloride preferably between about 50° C. and reflux or into the corresponding trifluoromethanesulfonyloxy-pyridazine esters 85 by treatment with trifluoromethanesulfonic anhydride and N-ethyldiisopropylamine or triethylamine in a solvent like dichloromethane preferably in a temperature range between −50° C. and 0° C. (step d). Suzuki reactions as described for step a) in Scheme 1 transform chloro-pyridazine esters 85 or trifluoromethanesulfonyloxy-pyridazine esters 85 into aryl pyridazine esters 87 (step f). Alternatively, chloro-pyridazine esters 85 can be prepared from unsubstituted chloro-pyridazine esters 86 by an alkylation reaction using a free alkyl radical, e.g. generated by silver-catalyzed oxidative decarboxylation of an alkane carboxylic acid and subsequent separation of isomers as described in Volonterio, A.; Moisan, L.; Rebek, J., Jr. *Organic Letters* (2007), 9(19), 3733-3736 (step e). Aryl pyridazine esters 87 can be saponified and coupled with amines (III) as described for steps d and e, Scheme 1, (steps g, h) to give aryl pyridazine amides 89.

Scheme 6

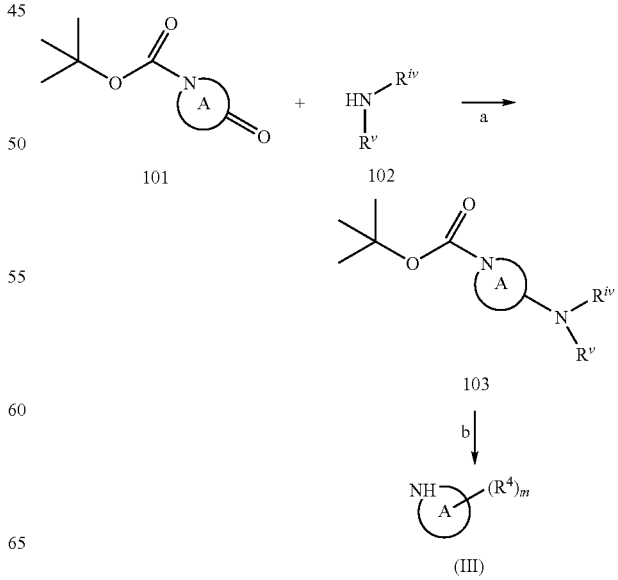

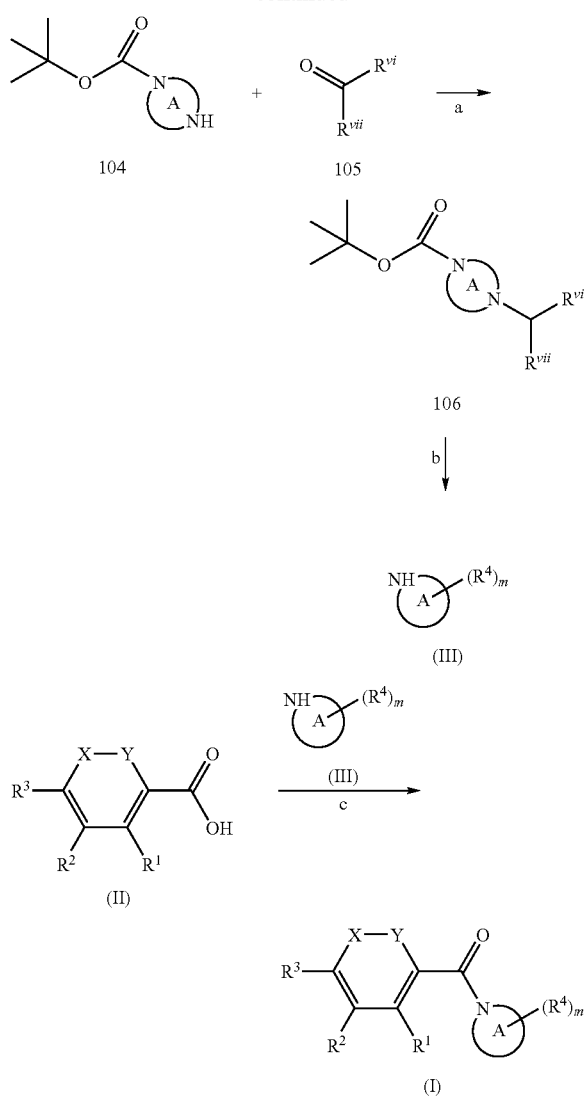

(In Scheme 6,

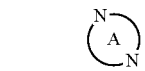

$R^1$, $R^2$, $R^3$ and $R^4$ and m are as defined as described before.

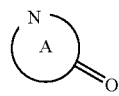

is heterocyclyl, which is a non-aromatic mono-cyclic radical of four to eight ring atoms, in which one ring atom is a nitrogen atom, the remaining ring atoms being carbon atoms; one of these carbon atoms is bearing a carbonyl group, said carbon atom is not directly bonded to the nitrogen atom.

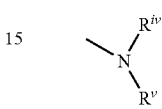

is heterocyclyl, which is a non-aromatic mono-cyclic radical of four to eight ring atoms, in which two ring atoms are nitrogen atoms, the remaining ring atoms being carbon atoms. $R^{iv}$ and $R^v$ are independently hydrogen, $C_{1-6}$ alkyl, heteroalkyl, optionally substituted $C_{3-7}$ cycloalkyl or optionally substituted heterocyclyl or $$\diagdown_N \diagdown \begin{matrix} R^{iv} \\ R^v \end{matrix}$$

is optionally substituted heterocyclyl.

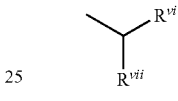

is $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, optionally substituted $C_{3-7}$ cycloalkyl, optionally substituted $C_{3-7}$ cycloalkyl $C_{1-6}$ alkyl, optionally substituted phenyl $C_{1-6}$ alkyl, optionally substituted heteroaryl $C_{1-6}$ alkyl, optionally substituted heterocyclyl or optionally substituted heterocyclyl $C_{1-6}$ alkyl.)

Secondary amines (III) (Scheme 6) are known, can be prepared by the methods known in the art or the methods described in the examples or can be prepared e.g. by reductive amination of ketones 101 with secondary amines 102 or by reductive amination of secondary amines 104 with ketones 105 e.g. by using sodium triacetoxy-borohydride, sodium cyano-borohydride or borane-pyridine complex as reagents in the presence of acetic acid and potentially a base, such as trietylamine, in a solvent, such as 1,2-dichloro-ethane, at temperatures around room temperature (step a). Such a reductive amination leads to Boc-protected adducts 103 or 106 which are subsequently deprotected by well established procedures as e.g. trifluoroacetic acid with or without an additional solvent or alcoholic hydrogen chloride to give secondary amines (III) (step b). Biaryl carboxylic acids (II) can then be coupled with secondary amines (III) i) by transformation of the biaryl carboxylic acids (II) into the corresponding acid chlorides, preferably by reaction with oxalyl chloride and a catalytic amount of N,N-dimethylformamide and optionally using dichloromethane as co-solvent followed by evaporation and reaction of the acid chlorides with secondary amines (III) in a solvent like dichloromethane or N,N-dimethylformamide in the presence of a base like triethylamine preferably between 0° C. and room temperature or ii) by suitable amide coupling reactions, such as using of O-(7-azabenzotriazol-1-yl)-1,1,3,3-tetramethyluronium hexafluorophosphate (HATU), triethylamine, in N,N-dimethylformamide preferably between 0° C. and room temperature (step c). During these coupling reactions, OH-functions potentially present in secondary amines (III) can potentially be protected by a suitable protective group which is removed after the coupling reaction or at a later stage of the synthesis.

Scheme 7

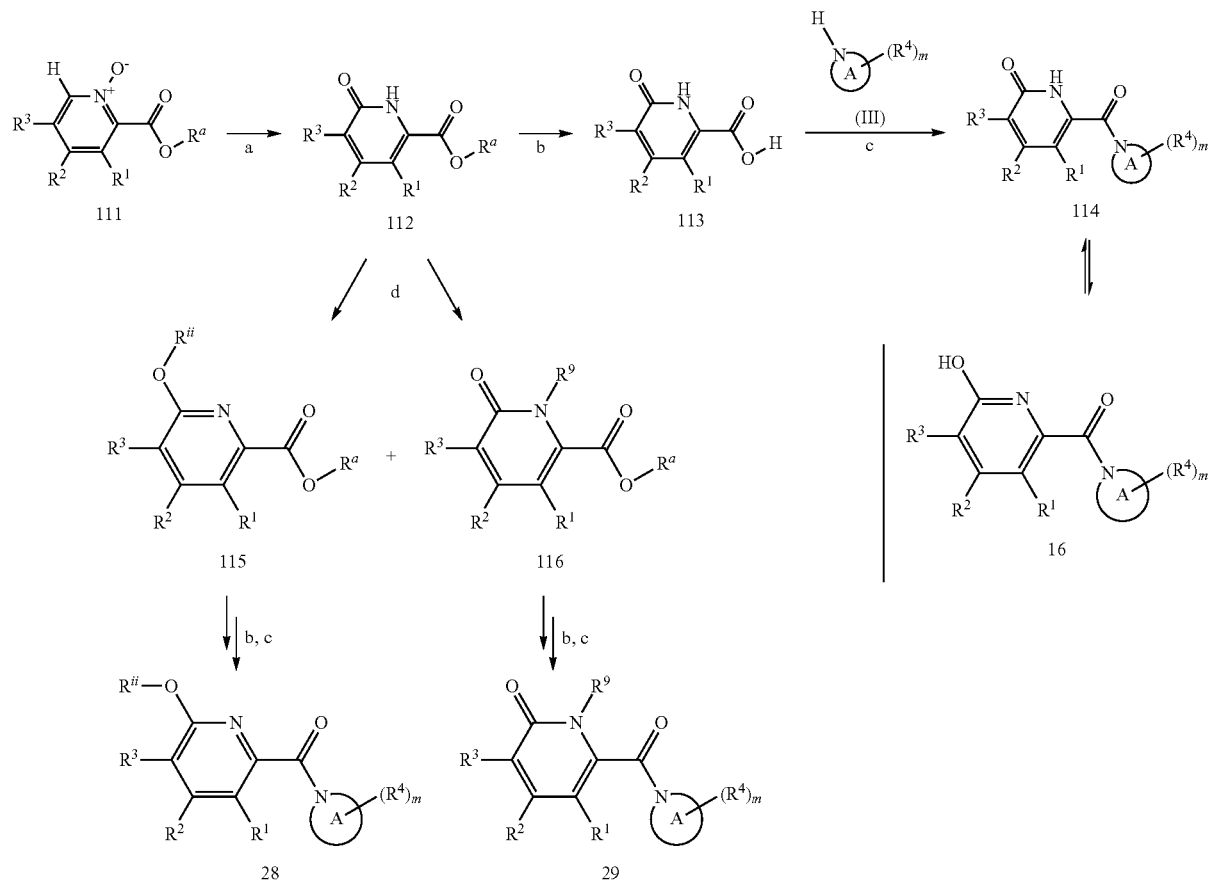

(In Scheme 7,

, $R^1$, $R^2$, $R^3$, $R^4$, and m are defined as described before. $R^a$ is $C_{1-6}$ alkyl. $R^{ii}$ is $C_{1-6}$ alkyl, halo $C_{1-6}$ alkyl, $C_{3-7}$ cycloalkyl, optionally substituted heteroaryl, optionally substituted phenyl-$C_{1-6}$ alkyl or optionally substituted heteroaryl-$C_{1-6}$ alkyl or heteroalkyl, said heteroalkyl optionally carrying a protective function which can be removed subsequently.)

Treatment of N-oxides 111 (compare N-oxides 4, Scheme 1) with trifluoro acetic acid anhydride in a solvent like ethyl acetate and in the presence of a base like collidine in a temperature range between about 50° C. and the reflux temperature of the solvent gives pyridones 112 (step a). Saponification, e.g. using sodium hydroxide in tetrahydrofuran, gives acids 113 (step b), which can be coupled with secondary amines (III) to amides 114 (tautomers of compounds 16) by a variety of amide coupling reactions, preferably using di-imidazol-1-yl-methanone as acid activating reagent in a solvent mixture of acetonitrile and tetrahydrofuran, preferably around room temperature (step c). Alkylation of pyridones 112 as described for hydroxy-pyridine-piperdine amides 23 (Scheme 2) gives mixtures of N- and O-alkylated or arylated pyridine ester compounds 115 and 116 (step d). Alkylated pyridine esters 115 and 116 can be saponified and coupled to give pyridine amides 28 and 29 (steps b, c).

Scheme 8

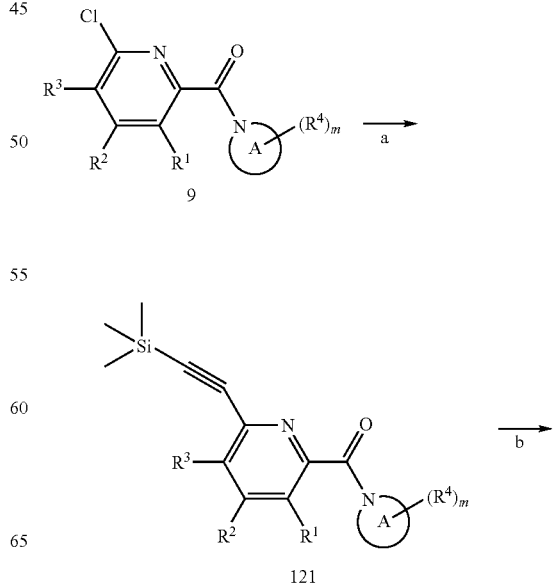

Scheme 9

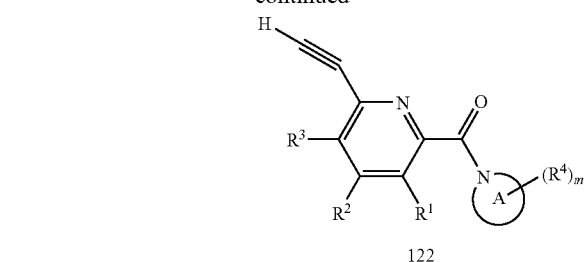

122

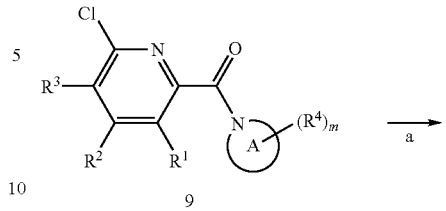

9

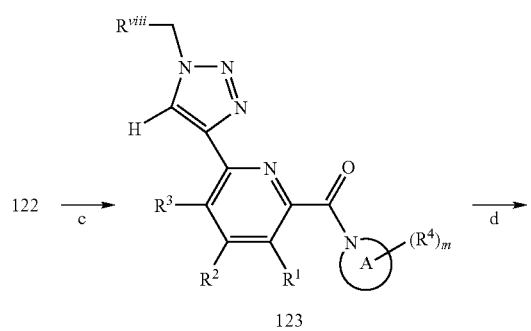

123

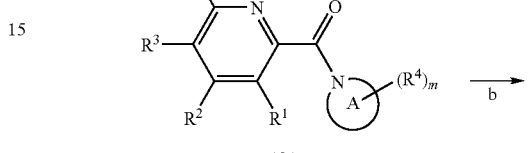

131

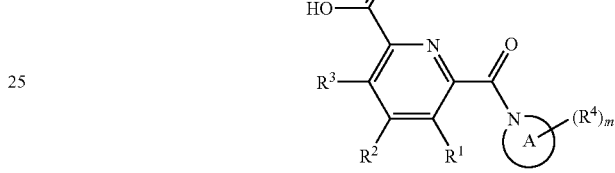

132

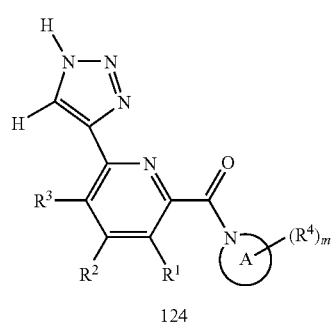

124

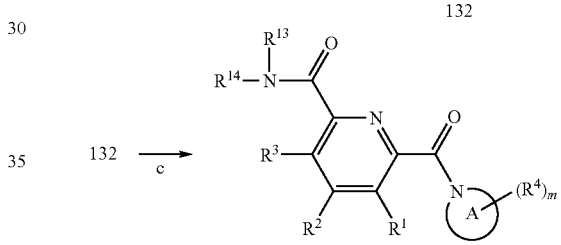

133

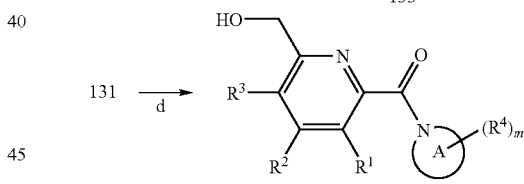

134

(In Scheme 8,

, $R^1$, $R^2$, $R^3$, $R^4$, and m are defined as described before. $R^{viii}$ is optionally substituted phenyl.)

Sonogashira reaction of chlorides 9 with a ethynyl-trimethyl-silane: e.g. by treatment with bis(triphenylphosphine) palladium(II) dichloride, copper(I) iodide in triethylamine at a temperature around 125° C. (in a closed vessel) gives acetylene pyridines 121 (step a). Mild hydrolysis (e.g. by using potassium carbonate in EtOH/THF 5:1 at RT) removes the silyl group and gives acetylene pyridines 122 (step b). Acetylene pyridines 122 react with optionally substituted benzyl azides in the presence copper(I) iodide and sodium-ascorbate in a solvent like DMF/H₂O around RT to give benzyl-triazolo pyridines 123 (step c). Removal of the optionally substituted benzyl groups, e.g. by treatment with trifluoroacetic acid preferably at reflux gives unprotected triazolo pyridines 124 (step d).

(In Scheme 9,

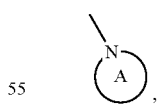, $R^1$, $R^2$, $R^3$, $R^4$, $R^{13}$, $R^{14}$, and m are defined as described before.

Carbonlyation of chlorides 9 e.g. by using (1,1'-bis-diphenylphosphino)-ferrocene)palladium-(II)dichloride (1:1 complex with $CH_2Cl_2$) as catalyst in a solvent like MeOH/EtOAc and in the presence of a base like triethylamine in a temperature range of about 100° C. to 150° C. and 50 to 100 bar CO pressure gives methoxy carbonyl pyridines 131 (step a). Methoxy carbonyl pyridines 131 can be saponified to carboxy pyridines 132, e.g. by using lithium hydroxide in a solvent like THF/MeOH (step b). Carboxy pyridines 132 can be converted into the corresponding amides 133 by standard amide forming reactions such as e.g. using O-(7-azabenzotriazol-1-yl)-1,1,3,3-tetramethyluronium hexafluorophosphate (HATU), triethylamine, in N,N-dimethylformamide preferably between 0° C. and room temperature (step c). Reduction of methyl ester pyridines 131 with lithium borohydride in a solvent like EtOH gives hydroxymethyl pyridines 134 (step d).

In addition to the reaction steps explicitly described in Schemes 1-9, optionally, additional well established synthetic structural modification can be applied to any substituent at any stage of the syntheses described, as e.g. introduction and removal of protective groups.

As described above, the compounds of formula (I) are CCR-2 receptor antagonists, with some antagonist activity also at CCR-3 and CCR-5. These compounds consequently prevent migration of various leukocyte populations through the blockade of CCR-2 stimulation. They therefore can be used for the treatment and/or prevention of inflammatory and/or allergic diseases, such as peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis and/or burns/ulcers in Diabetes/CLI, and asthma.

Prevention and/or treatment of inflammatory diseases, particularly peripheral arterial occlusive diseases or atherothrombosis is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of inflammatory and/or allergic diseases, particularly as therapeutically active substances for the treatment and/or prophylaxis of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis, burns/ulcers in Diabetes/CLI, and allergy, asthma.

The invention also relates to the use of compounds as described above for the preparation of medicaments for the therapeutic and/or prophylactic treatment of inflammatory and/or allergic diseases, particularly for the therapeutic and/or prophylactic treatment of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis, burns/ulcers in Diabetes/CLI, and asthma. Such medicaments comprise a compound as described above.

The invention also relates to the process and the intermediates for manufacturing the compounds of formula (I) as well as the process for manufacturing the intermediates.

CCR-2 receptor antagonistic activity by the compounds of the present invention can be demonstrated by the following assays.

Receptor Binding Assay

Binding assays were done with membranes from CHOK1-CCR2B-A5 cells (Euroscreen) stably overexpressing the human CCR2B.

Membranes were prepared by homogenizing the cells in 10 mM Tris pH 7.4, 1 mM EDTA, 0.05 mM benzamidine, leupeptin 6 mg/L and separating the debris at 1000 g. The membranes were then isolated at 100000 g in 50 mM Tris pH 7.4, $MgCl_2$ 10 mM, EGTA 1 mM, glycerol 10%, benzamidine 0.05 mM, leupeptine 6 mg/l.

For binding, CCR2 antagonist compounds were added in various concentrations in 50 mM HEPES pH 7.2, 1 mM $CaCl_2$, 5 mM $MgCl_2$, 0.5% BSA, 0.01% $NaN_3$, together with 100 pM $^{125}$I-MCP-1 (PerkinElmer, 2200 Ci/mmol) to about 5 fMol CCR2 membranes and incubated for 1 hour at room temperature. For unspecific control 57.7 nM MCP-1 (R&D Systems or prepared at Roche) was added. Membranes were harvested through GF/B (glass fiber filter; PerkinElmer) plates, equilibrated with 0.3% polyethylenimine, 0.2% BSA, air dried and binding was determined by counting in a top-counter (NXT Packard). Specific binding was defined as total binding minus nonspecific binding and typically represents about 90-95% of the total binding. Antagonist activity is indicated as inhibitor concentration required for 50% inhibition ($IC_{50}$) of specific binding.

Calcium Mobilization Assay

CHOK1-CCR2B-A5 cells (from Euroscreen) stably overexpressing the human chemokine receptor 2 isoform B were cultured in Nutrient Hams F12 medium supplemented with 5% FBS, 100 U/ml penicillin, 100 µg/ml streptomycin, 400 µg/ml G418 and 5 µg/ml puromycin.

For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 µM Fluo-4 in the same DMEM assay buffer for 2 hours at 30° C. Excess dye was removed and cells were washed with DMEM assay buffer. 384-well compound plates were prepared with DMEM assay buffer/0.5% DMSO with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 nM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

The compounds of general formula (I) exhibit IC50 values in the Ca mobilisation assay or in the receptor binding assay of 0.1 nM to 10 µM, preferably 1 nM to 1.5 µM for CCR2. The following table shows measured values in the calcium mobilization assay for some selected compounds of the present invention.

| Example | IC50(µM) | Example | IC50(µM) |
|---------|----------|---------|----------|
| 1 | 0.018 | 2 | 0.023 |
| 3 | 0.004 | 5 | 0.021 |
| 6 | 0.13 | 7 | 0.016 |
| 8 | 0.065 | 9 | 0.0064 |
| 10 | 0.078 | 11 | 0.071 |
| 13 | 0.058 | 14 | 0.012 |
| 15 | 0.25 | 16 | 0.0042 |

-continued

| Example | IC50(μM) | Example | IC50(μM) |
|---|---|---|---|
| 17 | 0.0087 | | |
| 19 | 0.064 | 20 | 0.004 |
| 21 | 0.0032 | 22 | 0.018 |
| 23 | 0.041 | 24 | 0.0048 |
| 25 | 0.0023 | 26 | 0.067 |
| 27 | 0.041 | 28 | 0.25 |
| 30 | 0.054 | 31 | 0.025 |
| 32 | 0.023 | 33 | 0.016 |
| 34 | 0.059 | 35 | 0.56 |
| 36 | 0.18 | 37 | 0.036 |
| 39 | 0.0058 | | |
| 40 | 0.0039 | 41 | 0.016 |
| 42 | 0.026 | 43 | 0.025 |
| 44 | 0.012 | 45 | 0.0075 |
| 46 | 0.012 | 47 | 0.31 |
| 48 | 0.012 | 49 | 0.01 |
| 50 | 0.018 | 51 | 0.0055 |
| | | 53 | 0.015 |
| 54 | 0.12 | 55 | 0.13 |
| 56 | 0.013 | 57 | 0.21 |
| 58 | 0.19 | 59 | 0.49 |
| 60 | 0.29 | 61 | 0.32 |
| 62 | 0.069 | 63 | 0.032 |
| 64 | 0.3 | 65 | 0.0076 |
| 66 | 0.2 | 67 | 0.059 |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

Abbreviations:
The following are a list of abbreviations and/or acronyms with their corresponding definitions used in the following examples: AcOH=Acetic acid, BOC=t-Butyloxycarbonyl, BuLi=Butyllithium, CDI=1,1-Carbonyldiimidazole, $CH_2Cl_2$=Dichloromethane, DCE=1,2-Dichloroethane, DIBALH=Di-i-butylaluminium hydride, DCC=N,N'-Dicyclohexylcarbodiimide, DMA=N,N-Dimethylacetamide, DMAP=4-Dimethylaminopyridine, DMF=N,N-Dimethylformamide, EDCI =N-(3-Dimethylaminopropyl)-N'-ethylcarbodiimide hydrochloride, EtOAc=Ethylacetate, EtOH=Ethanol, $Et_2O$=Diethylether, $Et_3N$=Triethylamine, eq=Equivalents, HATU=O-(7-azabenzotriazol-1-yl)-1,1,3,3-tetramethyluronium hexafluorophosphate, HPLC=High performance liquid chromatography, HOBT=1-Hydroxybenzotriazole, Huenig's base=$iPr_2NEt$=N-Ethyl diisopropylamine, IPC=In process control, LAH=Lithium aluminium hydride, LDA=Lithium diisopropylamide, $LiBH_4$=Lithium borohydride, MeOH=Methanol, NaI=Sodium iodide, Red-Al=Sodium bis(2-methoxyethoxy)aluminium hydride, RT=room temperature, TBDMSCl=t-Butyldimethylsilyl chloride, TFA=Trifluoroacetic acid, THF=Tetrahydrofuran, quant=quantitative.

General Remarks
All reactions were performed under argon.

Intermediate 1

3-Methyl-1-oxy-5-(3-trifluoromethyl-phenyl)-pyridine-2-carboxylic acid

A) 3-Methyl-5-(3-trifluoromethyl-phenyl)-pyridine-2-carboxylic acid methyl ester To a degassed solution of 8.35 g (36.3 mmol) of 5-bromo-3-methyl-pyridine-2-carboxylic acid methyl ester [Wu, G. G.; Wong, Y.-S.; Poirier, M. *Organic Letters* (1999), 1(5), 745-747] in 180 ml of dioxane were added 13.79 g (72.6 mmol) of 3-(trifluoromethyl)phenyl boronic acid and 11.54 g (108.9 mmol) of sodium carbonate (dissolved in 55 ml of $H_2O$). While stirring, 1.33 g (1.89 mmol) of (1,1'-bis-diphenylphosphino)-ferrocene)palladium-(II)dichloride (1:1 complex with $CH_2Cl_2$) was added and the reaction mixture was stirred at RT for 4 hours, then heated up to 50° C. After 90 min, it was cooled down to RT, poured into crashed ice and extracted twice with EtOAc; the organic phases were washed with water, dried over magnesium sulfate, filtered and evaporated. The residue was purified by flash column chromatography (heptane/EtOAc 9:1 to 1:1) to give 9.35 g (87%) of the title compound as light yellow solid. MS: 296.1 (MH$^+$).

B) 3-Methyl-5-(3-trifluoromethyl-phenyl)-pyridine-2-carboxylic acid

To a solution of 1.00 g (3.4 mmol) of 3-methyl-5-(3-trifluoromethyl-phenyl)-pyridine-2-carboxylic acid methyl ester in 40 ml of THF/MeOH (1:1) was added 8.47 ml (8.5 mmol) of lithium hydroxide solution (1 molar in water) and the reaction mixture was stirred at RT. After 20 hours, the solvents were evaporated and the residue poured into crashed ice, the pH was adjusted to 1-2 with HCl 1N and the reaction mixture was extracted twice with EtOAc; the organic phases were washed with water, dried over magnesium sulfate, filtered and evaporated. The residue was purified by re-crystallization from CH$_2$Cl$_2$/heptane to give 0.94 g (99%) of the title compound as colorless solid. MS: 280.0 (M–H$^-$).

C) 3-Methyl-1-oxy-5-(3-trifluoromethyl-phenyl)-pyridine-2-carboxylic acid

To a solution of 0.48 g (1.7 mmol) of 3-methyl-5-(3-trifluoromethyl-phenyl)-pyridine-2-carboxylic acid in 15 ml of CH$_2$Cl$_2$ was added 1.23 g (5.2 mmol) of 3-chloro-perbenzoic acid and the reaction mixture was stirred for 3 days at RT. Then, it was filtered, the filtrate was evaporated and the residue purified by flash column chromatography (heptane/EtOAc 4:1 to 0:1) to give 0.33 g (66%) of the title compound as light yellow solid. MS: 296.3 (M–H$^-$).

Intermediates 2 and 3

6-Chloro-3-methyl-5-(3-trifluoromethyl-phenyl)-pyridine-2-carboxylic acid methyl ester (Intermediate 2) and 4-chloro-3-methyl-5-(3-trifluoromethyl-phenyl)-pyridine-2-carboxylic acid methyl ester (Intermediate 3)

3.48 g (11.2 mmol) of 3-methyl-1-oxy-5-(3-trifluoromethyl-phenyl)-pyridine-2-carboxylic acid methyl ester [prepared from 3-methyl-5-(3-trifluoromethyl-phenyl)-pyridine-2-carboxylic acid methyl ester (intermediate 1A) by reaction with 3-chloro-perbenzoic acid in analogy to the procedure described for the preparation of intermediate 1C] was added at RT while stirring to 20.4 ml=34.25 g (223.3 mmol) of phosphorus oxychloride and the reaction mixture was warmed up to 50° C. After 2 hours, it was cooled down to RT and poured into crashed ice. This solution was carefully neutralized with solid sodium carbonate and extracted twice with EtOAc; the organic phases were washed with water, dried over magnesium sulfate, filtered and evaporated. The residue was purified by flash column chromatography (heptane/CH$_2$Cl$_2$ 1:1 to 0:1) to give 2.52 g (68%) 6-chloro-3-methyl-5-(3-trifluoromethyl-phenyl)-pyridine-2-carboxylic acid methyl ester as light yellow oil; [MS: 330.0 (MH$^+$, 1Cl)] and 1.10 g (30%) 4-chloro-3-methyl-5-(3-trifluoromethyl-phenyl)-pyridine-2-carboxylic acid methyl ester as colorless solid. MS: 330.0 (MH$^+$, 1Cl).

Intermediate 4

N-{5-Methyl-6-[(4-pyrrolidin-1-ylpiperidin-1-yl)carbonyl]-3-[3-(trifluoromethyl)phenyl]pyridin-2-yl}-N-(methylsulfonyl)methanesulfonamide A solution of 0.22 g (0.5 mmol) of [6-amino-3-methyl-5-(3-trifluoromethyl-phenyl)-pyridin-2-yl]-(4-pyrrolidin-1-yl-piperidin-1-yl)-methanone (example 7) in 5.0 ml of DMF was treated with 0.43 ml=0.309 g (3.1 mmol) of Et$_3$N and 0.006 g (0.05 mmol) of DMAP. To the stirred solution was added 0.08 ml=0.12 g (1.0 mmol) of methanesulfonyl chloride drop by drop and the reaction mixture was subsequently warmed up to 50° C. After 5 hours, it was poured into crashed ice and extracted twice with EtOAc; the organic phases were washed with water, dried over magnesium sulfate, filtered and evaporated. The residue was purified by flash column chromatography (CH$_2$Cl$_2$/MeOH 1:0 to 4:1) to give 0.13 g (44%) of the title compound as yellow solid. MS: 589.1 (MH$^+$).

Intermediate 5

1,4-Dimethyl-2-oxo-6-(3-trifluoromethyl-phenyl)-1,2-dihydro-pyridine-3-carboxylic acid A) 2,6-Dichloro-4-methyl-nicotinic acid methyl ester To a solution of 8.05 g (39.1 mmol) of 2,6-dichloro-4-methyl-nicotinic acid [Lamm, G. Ger. Offen. (1977), DE 2538950] in 100 ml of DMF was added 8.10 g (58.6 mmol) of potassium carbonate. While stirring, 12.16 ml=27.7 g (195.4 mmol) of iodomethane was added drop by drop and the reaction mixture was stirred for 6 hours at RT. It was then poured into crashed ice and extracted twice with EtOAc; the organic phases were washed with water, dried over magnesium sulfate, filtered and evaporated to give 8.47 g (99%) of the title compound as light yellow solid. MS: 219.0 (M$^+$, 2Cl).

B) 6-Chloro-2-methoxy-4-methyl-nicotinic acid methyl ester

To a solution of 6.50 g (29.5 mmol) of 2,6-dichloro-4-methyl-nicotinic acid methyl ester in 75 ml of CH$_2$Cl$_2$ was added at 0° C. 6.56 ml (35.4 mmol) of a sodium methoxide solution (5.4 molar in MeOH). After 16 hours, the reaction mixture was warmed up to RT and stirred again 16 hours at this temperature and subsequently poured into crashed ice; then, the pH was adjusted to 4-5 with 2N acetic acid and the reaction mixture was extracted twice with CH$_2$Cl$_2$; the organic phases were washed with water, dried over magnesium sulfate, filtered and evaporated. The residue was purified by flash column chromatography (heptane/EtOAc 1.0 to 98:2) to give 5.79 g (91%) of the title compound as colorless solid. MS: 216.1 (MH$^+$, 1Cl).

C) 2-Methoxy-4-methyl-6-(3-trifluoromethyl-phenyl)-nicotinic acid methyl ester

To a solution of 5.75 g (26.7 mmol) of 6-chloro-2-methoxy-4-methyl-nicotinic acid methyl ester in 250 ml of DMF was added 10.13 g (53.3 mmol) of 3-trifluoromethyl-phenylboronic acid followed by 50.0 ml of a solution of tribasic potassium phosphate (2 M in water). Finally, 1.54 g (1.3 mmol) of tetrakis-(triphenylphosphine)-palladium was added and the reaction mixture was subsequently warmed up to 80° C. After 5 hours, it was cooled down to RT, poured into crashed ice and extracted twice with CH$_2$Cl$_2$; the organic phases were washed with water, dried over magnesium sulfate, filtered and evaporated. The residue was purified by flash column chromatography (heptane/EtOAc 1:0 to 9:1) to give 8.54 g (98%) of the title compound as light yellow oil. MS: 326.1 (MH$^+$).

D) 2-Hydroxy-4-methyl-6-(3-trifluoromethyl-phenyl)-nicotinic acid and 4-Methyl-2-oxo-6-(3-trifluoromethyl-phenyl)-1,2-dihydro-pyridine-3-carboxylic acid (tautomers)

A solution of 0.325 g (1.0 mmol) of 2-methoxy-4-methyl-6-(3-trifluoromethyl-phenyl)-nicotinic acid methyl ester in 10 ml of $CH_2Cl_2$ was cooled down to 0° C., 2.0 ml (2.0 mmol) of a solution of boron tribromide (1 molar in $CH_2Cl_2$) was added drop by drop and the reaction mixture was subsequently warmed up to RT. After two hours, 1.0 ml of MeOH was added and 90 min later, the reaction mixture was evaporated. The crude intermediate formed was used without purification in the next step.

E) 2-Hydroxy-4-methyl-6-(3-trifluoromethyl-phenyl)-nicotinic acid methyl ester and 4-Methyl-2-oxo-6-(3-trifluoromethyl-phenyl)-1 2-dihydro-pyridine-3-carboxylic acid methyl ester tautomers A solution of 0.30 g (1.0 mmol) of 2-hydroxy-4-methyl-6-(3-trifluoromethyl-phenyl)-nicotinic acid/4-methyl-2-oxo-6-(3-trifluoromethyl-phenyl)-1,2-dihydro-pyridine-3-carboxylic acid in 15 ml of MeOH was treated with 0.06 ml=0.01 g (0.1 mmol) of $H_2SO_4$ (98%) and the reaction mixture was heated up to reflux. After 4 hours, it was cooled down to RT, poured into crashed ice and extracted twice with $CH_2Cl_2$; the organic phases were washed with water, dried over magnesium sulfate, filtered and evaporated. The residue was purified by flash column chromatography ($CH_2Cl_2$/MeOH 1:0 to 9:1) to give 0.24 g (77%) of the title compound as off-white solid. MS: 312.0 ($MH^+$).

F) 1,4-Dimethyl-2-oxo-6-(3-trifluoromethyl-phenyl)-1,2-dihydro-pyridine-3-carboxylic acid methyl ester A solution of 0.62 g (2.0 mmol) of 2-hydroxy-4-methyl-6-(3-trifluoromethyl-phenyl)-nicotinic acid methyl ester/4-methyl-2-oxo-6-(3-trifluoromethyl-phenyl)-1,2-dihydro-pyridine-3-carboxylic acid methyl ester in 20 ml of DMF was treated with 0.78 g (2.4 mmol) of cesium carbonate, followed by 0.62 ml=1.41 g (10.0 mmol) of iodomethane. This mixture was stirred for 70 hours at RT, then poured into crashed ice and extracted twice with $CH_2Cl_2$; the organic phases were washed with water, dried over magnesium sulfate, filtered and evaporated. The residue was purified by flash column chromatography (heptane/EtOAc 4:1 to 0:1) to give 0.21 g (33%) of the title compound as light yellow solid; [MS: 326.1 ($MH^+$)] and 0.42 g (65%) of 2-methoxy-4-methyl-6-(3-trifluoromethyl-phenyl)-nicotinic acid methyl ester as light yellow oil. MS: 326.1 ($MH^+$).

G) 1,4-Dimethyl-2-oxo-6-(3-trifluoromethyl-phenyl)-1,2-dihydro-pyridine-3-carboxylic acid To a solution of 0.60 g (1.8 mmol) of 1,4-dimethyl-2-oxo-6-(3-trifluoromethyl-phenyl)-1,2-dihydro-pyridine-3-carboxylic acid methyl ester 4.0 ml of THF/MeOH (1:1) was added 11.0 ml (11.0 mmol) of lithium hydroxide solution (1 molar in water) and the reaction mixture was then heated up to 60° C. After 7 hours, the solvents were evaporated and the residue poured into crashed ice, acidified with 2N HCl and extracted twice with $CH_2Cl_2$; the organic phases were washed with water, dried over magnesium sulfate and evaporated. The residue was purified by flash column chromatography ($CH_2Cl_2$/MeOH 1:0 to 95:5) to give 0.53 g (94%) of the title compound as light yellow solid. MS: 310.1 ($M-H^-$).

Intermediate 6

Benzoic acid (S)-1-piperidin-4-yl-pyrrolidin-2-ylmethyl ester

A) 4-((S)-2-Hydroxymethyl-pyrrolidin-1-yl)-piperidine-1-carboxylic acid tert-butyl ester A solution of 10.0 g (50.2 mmol) of 4-oxo-piperidine-1-carboxylic acid tert-butyl ester and 6.00 ml=6.15 g (60.2 mmol) of (S)-(−)-pyrrolidin-2-yl-methanol in 100.0 ml of EtOH was treated with 100.0 ml of 1,2-dichloroethane, followed by 7.53 ml (60.2 mmol) of borane-pyridine complex (8 molar). Then, 7.46 ml=7.84 g (130.5 mmol) of acetic acid was added to this solution. After stirring at RT for 16 hours, the reaction mixture was poured into crashed ice; then, the pH was adjusted to 9-10 with sodium carbonate solution and the mixture was extracted twice with EtOAc; the combined organic phases were washed with water, dried over $MgSO_4$, filtered and evaporated. The residue was purified by flash column chromatography ($CH_2Cl_2$/MeOH 1:0 to 9:1) to give 10.4 g (73%) of the title compound as light yellow oil. MS: 285.1 ($MH^+$).

B) 4-((S)-2-Benzoyloxymethyl-pyrrolidin-1-yl)-piperidine-1-carboxylic acid tert-butyl ester 3.35 g (11.8 mmol) of 4-((S)-2-hydroxymethyl-pyrrolidin-1-yl)-piperidine-1-carboxylic acid tert-butyl ester was dissolved in 55 ml of THF at RT and treated with 0.57 g (13.0 mmol) of sodium hydride (55% in mineral oil). 1.68 ml=2.03 g (14.1 mmol) of benzoyl chloride was added drop by drop and stirring continued for 2 hours. The reaction mixture was then poured into crashed ice and extracted three times with EtOAc; the organic phases were washed with water, dried over magnesium sulfate, filtered and evaporated. The residue was purified by flash column chromatography ($CH_2Cl_2$/MeOH 1:0 to 95:5) to give 2.80 g (61%) of the title compound as yellow oil. MS: 389.3 ($MH^+$).

C) Benzoic acid (S)-1-piperidin-4-yl-pyrrolidin-2-ylmethyl ester

To a solution of 2.78 g (7.2 mmol) of 4-((S)-2-benzoyloxymethyl-pyrrolidin-1-yl)-piperidine-1-carboxylic acid tert-butyl ester in 80 ml of $CH_2Cl_2$ was added 5.83 ml of TFA (90% in water) drop by drop. After 16 hours, the reaction mixture was poured into crashed ice; then, the pH was adjusted to 9-10 with sodium carbonate solution and the mixture was extracted three times with $CH_2Cl_2$; the organic phases were washed with water, dried over magnesium sulfate, filtered and evaporated. The residue was purified by flash column chromatography [$CH_2Cl_2$ (sat. with $NH_3$)/MeOH 1:0 to 9:1] to give 1.96 g (95%) of the title compound as yellow oil. MS: 289.1 ($MH^+$).

Intermediates 7, 8 and 9

3-Chloro-5-(3-trifluoromethyl-phenyl)-pyridine-2-carboxylic acid methyl ester (Intermediate 7), 3,5-bis-(3-trifluoromethyl-phenyl)-pyridine-2-carboxylic acid methyl ester (Intermediate 8) and 5-chloro-3-(3-trifluoromethyl-phenyl)-pyridine-2-carboxylic acid methyl ester (Intermediate 9)

To a degassed solution of 10.48 g (50.9 mmol) of 3,5-dichloro-pyridine-2-carboxylic acid methyl ester [prepared in analogy to the procedure described for the preparation of intermediate 5A from 3,5-dichloro-pyridine-2-carboxylic acid and iodomethane, potassium carbonate in DMF] in 400 ml of dimethoxyethane were added 14.49 g (76.3 mmol) of 3-(trifluoromethyl)phenyl boronic acid and 49.73 g (152.6 mmol) of caesium carbonate. While stirring, 0.77 g (1.50 mmol) of [(t-Bu)$_2$P(OH)]$_2$PdCl$_2$ (POPd) was added and the reaction mixture was stirred at reflux for 7 hours. It was then cooled down to RT, poured into crashed ice and extracted twice with EtOAc; the organic phases were washed with water, dried over magnesium sulfate, filtered and evaporated. The residue was purified by flash column chromatography (heptane/EtOAc 98:2 to 1:1) to give 3.22 g (20%) of 3-chloro-5-(3-trifluoromethyl-phenyl)-pyridine-2-carboxylic acid methyl ester as light yellow oil; [MS: 316.0 (MH$^+$, 1Cl)] and 2.80 g (12.9%) of 3,5-bis-(3-trifluoromethyl-phenyl)-pyridine-2-carboxylic acid methyl ester as light yellow solid; [MS: 426.1 (MH$^+$)] and 3.21 g (20.0%) of 5-chloro-3-(3-trifluoromethyl-phenyl)-pyridine-2-carboxylic acid methyl ester as light yellow oil. [MS: 316.0 (MH$^+$, 1Cl)].

Intermediate 10

Trifluoro-methanesulfonic acid 4-methyl-3-(4-pyrrolidin-1-yl-piperidine-1-carbonyl)-6-(3-trifluoromethyl-phenyl)-pyridin-2-yl ester A) 2-Methoxy-4-methyl-6-(3-trifluoromethyl-phenyl)-nicotinic acid To a solution of 0.325 g (1.00 mmol) of 2-methoxy-4-methyl-6-(3-trifluoromethyl-phenyl)-nicotinic acid methyl ester (intermediate 5C) in 20 ml of THF/MeOH (1:1) was added 2.50 ml (2.50 mmol) of lithium hydroxide solution (1 molar in water) drop by drop and the reaction mixture was then heated up to reflux. After 8 hours, it was poured into crashed ice and acidified with HCl/H$_2$O (1N) to pH 3.0 and then extracted twice with EtOAc; the organic phases were washed with water, dried over magnesium sulfate, filtered and evaporated. The residue was purified by flash column chromatography (CH$_2$Cl$_2$/MeOH 1:0 to 4:1) to give 0.24 g (77%) of the title compound as light yellow solid. MS: 310.0 (M–H$^-$).

B) [2-Methoxy-4-methyl-6-(3-trifluoromethyl-phenyl)-pyridin-3-yl]-(4-pyrrolidin-1-yl-piperidin-1-yl)-methanone A suspension of 0.200 g (0.64 mmol) 2-methoxy-4-methyl-6-(3-trifluoromethyl-phenyl)-nicotinic acid in 5 ml of CH$_2$Cl$_2$ was treated at RT with one drop of DMF; then, 0.06 ml=0.09 g (0.71 mmol) of oxalyl chloride was added to this solution drop by drop below 25° C. and the reaction mixture was stirred for 0.5 hour. After removal of the solvents by evaporation in a high vacuum, the residue was dissolved again in 10 ml of CH$_2$Cl$_2$ and 0.36 ml=0.26 g (2.57 mmol) of Et$_3$N was added while stirring, followed by 0.099 g (0.64 mmol) of 4-pyrrolidin-1-yl-piperidine. The reaction mixture was stirred at RT. After 16 hours, it was poured into crashed ice and extracted twice with CH$_2$Cl$_2$; the organic phases were washed with water, dried over magnesium sulfate, filtered and evaporated. The residue was purified by flash column chromatography (CH$_2$Cl$_2$/MeOH 98:2 to 4:1) to give 0.278 g (97%) of the title compound as yellow amorphous solid. MS: 448.1 (MH$^+$).

C) [2-Hydroxy-4-methyl-6-(3-trifluoromethyl-phenyl)-pyridin-3-yl]-(4-pyrrolidin-1-yl-piperidin-1-yl)-methanone; 4-Methyl-3-(4-pyrrolidin-1-yl-piperidine-1-carbonyl)-6-(3-trifluoromethyl-phenyl)-1H-pyridin-2-one (tautomers)

A solution of 5.25 g (11.7 mmol) of [2-methoxy-4-methyl-6-(3-trifluoromethyl-phenyl)-pyridin-3-yl]-(4-pyrrolidin-1-yl-piperidin-1-yl)-methanone in 180 ml of CH$_2$Cl$_2$ was cooled down to 0° C. and 23.5 ml (23.5 mmol) of a boron tribromide solution (1 molar in CH$_2$Cl$_2$) was added drop by drop. After stirring for 1 hour at RT, the reaction mixture was added drop by drop to a cold solution of NaHCO$_3$ (saturated in water) and it was then extracted twice with MeCl$_2$; the organic phases were washed with water, dried over magnesium sulfate, filtered and evaporated. The residue was purified by flash column chromatography (CH$_2$Cl$_2$/MeOH 98:2 to 4:1) to give 4.96 g (98%) of the title compound as light yellow solid. MS: 434.3 (MH$^+$).

D) Trifluoro-methanesulfonic acid 4-methyl-3-(4-pyrrolidin-1-yl-piperidine-1-carbonyl)-6-(3-trifluoromethyl-phenyl)-pyridin-2-yl ester 0.34 ml=0.256 g (2.0 mmol) of N-ethyldiisopropylamine was added to a solution of 0.43 g (1.0 mmol) of [2-hydroxy-4-methyl-6-(3-trifluoromethyl-phenyl)-pyridin-3-yl]-(4-pyrrolidin-1-yl-piperidin-1-yl)-methanone; 4-methyl-3-(4-pyrrolidin-1-yl-piperidine-1-carbonyl)-6-(3-trifluoromethyl-phenyl)-1H-pyridin-2-one (tautomers) in 10 ml of CH$_2$Cl$_2$ at RT. While stirring 0.24 ml=0.42 g (1.50 mmol) of trifluoromethanesulfonic anhydride were added to this suspension drop by drop which resulted in a clear solution. After 20 hours, the reaction mixture was poured into crashed ice and extracted twice with CH$_2$Cl$_2$; the organic phases were washed with water, dried over magnesium sulfate, filtered and evaporated. The residue was purified by flash column chromatography (CH$_2$Cl$_2$/MeOH 1:0 to 9:1) to give 0.21 g (37%) of the title compound as light brown amorphous solid. MS: 566.4 (MH$^+$).

Intermediate 11

3,6-Dichloro-5-(3-trifluoromethyl-phenyl)-pyridine-2-carboxylic acid methyl ester A) 3-Chloro-1-oxy-5-(3-trifluoromethyl-phenyl)-pyridine-2-carboxylic acid methyl ester A suspension of 1.997 g (6.3 mmol) of 3-chloro-5-(3-trifluoromethyl-phenyl)-pyridine-2-carboxylic acid methyl ester (intermediate 7) in 50 ml of MeCN was treated at RT with 1.25 g (13.3 mmol) of hydrogen peroxide urea adduct and the reaction mixture was stirred for 1 hour. It was then cooled down to 0° C. and 1.79 ml=2.71 g (12.6 mmol) of trifluoroacetic anhydride (98%) were added drop by drop below 3° C. The reaction mixture was then warmed up to RT, stirred for 3 hours and poured into crashed ice and extracted twice with CH$_2$Cl$_2$; the organic phases were washed with water, dried over magnesium sulfate, filtered and evaporated. The residue was purified by flash column chromatography (heptane/EtOAc 1:0 to 3:2) to give 1.83 g (87%) of the title compound as colorless solid. MS: 332.0 (MH$^+$, 1Cl).

B) 3,6-Dichloro-5-(3-trifluoromethyl-phenyl)-pyridine-2-carboxylic acid methyl ester In analogy to the procedure described for the preparation of intermediates 2 and 3,3-chloro-1-oxy-5-(3-trifluoromethylphenyl)-pyridine-2-carboxylic acid methyl ester was reacted with phosphorus oxychloride at 50° C. to give the title compound (major isomer) as light yellow solid. MS: 350.1 (MH$^+$, 2Cl); and 3,4-dichloro-5-(3-trifluoromethyl-phenyl)-pyridine-2-carboxylic acid methyl ester (minor isomer) as colorless oil. MS: 350.1 (MH$^+$, 2Cl).

Intermediate 12

[3-Methyl-5-(3-trifluoromethyl-phenyl)-6-trimethylsilanylethynyl-pyridin-2-yl]-(4-pyrrolidin-1-yl-piperidin-1-yl)-methanone 0.90 g (1.99 mmol) of [6-chloro-3-methyl-5-(3-trifluoromethyl-phenyl)-pyridin-2-yl]-(4-pyrrolidin-1-yl-piperidin-1-yl)-methanone (example 3), 0.042 g (0.06 mmol) of bis(triphenylphosphine)palladium(II) chloride and 0.021 g (0.11 mmol) of copper(I) iodide were suspended in 2.0 ml of triethylamine. After addition of 2.14 ml=1.50 g (15.0 mmol) of ethinyltrimethylsilane, the reaction vessel was sealed, heated up to 125° C. and stirring continued for four days. The reaction mixture was then poured into crashed ice and extracted three times with $CH_2Cl_2$; the organic phases were washed with water, dried over magnesium sulfate, filtered and evaporated. The residue was purified by flash column chromatography ($CH_2Cl_2$/MeOH 1:0 to 9:1) to give 0.693 g (68%) of the title compound as dark brown oil. MS: 514.4 (MH$^+$).

Intermediate 13

[6-[1-(4-Methoxy-benzyl)-1H-[1,2,3]triazol-4-yl]-3-methyl-5-(3-trifluoromethyl-phenyl)-pyridin-2-yl]-(4-pyrrolidin-1-yl-piperidin-1-yl)-methanone A solution of 0.30 g (0.68 mmol) of [6-ethynyl-3-methyl-5-(3-trifluoromethyl-phenyl)-pyridin-2-yl]-(4-pyrrolidin-1-yl-piperidin-1-yl)-methanone (example 24) and 0.116 g (0.71 mmol) of 1-azidomethyl-4-methoxy-benzene in 3.0 ml of DMF was treated with 0.013 g (0.066 mmol) of (+)-sodium-L-ascorbate and 0.129 g (0.68 mmol) of copper(I) iodide in 1.0 ml of $H_2O$ and the reaction was stirred at RT for 2 hours. Then, the solvents were removed by evaporation in high vacuum, the residue was diluted with $H_2O/NH_4OH$ (25%) and extracted twice with $CH_2Cl_2$; the organic phases were washed with water, dried over magnesium sulfate, filtered and evaporated. The residue was purified by flash column chromatography ($CH_2Cl_2$/MeOH 1:0 to 95:5) to give 0.363 g (88%) of the title compound as light brown oil. MS: 605.4 (MH).

Intermediate 14

[6-(2-Benzyloxy-ethylamino)-3-methyl-5-(3-trifluoromethyl-phenyl)-pyridin-2-yl]-(4-pyrrolidin-1-yl-piperidin-1-yl)-methanone In analogy to the procedure described for the preparation of example 6, [6-chloro-3-methyl-5-(3-trifluoromethyl-phenyl)-pyridin-2-yl]-(4-pyrrolidin-1-yl-piperidin-1-yl)-methanone (example 3) was reacted with 2-benzyloxy-ethylamine, [rac]-2,2'-bis(diphenylphosphino)-1,1'-binaphthyl, palladium(II) acetate and cesium carbonate in toluene at reflux to give the title compound as yellow oil. MS: 567.4 (MH$^+$).

Intermediate 15

6-Hydroxy-3-methyl-5-(3-trifluoromethyl-phenyl)-pyridine-2-carboxylic acid; 3-Methyl-6-oxo-5-(3-trifluoromethyl-phenyl)-1,6-dihydro-pyridine-2-carboxylic acid (tautomers)

A) 3-Methyl-1-oxy-5-(3-trifluoromethyl-phenyl)-pyridine-2-carboxylic acid methyl ester 260 g (881 mmol) 3-methyl-5-(3-trifluoromethyl-phenyl)-pyridine-2-carboxylic acid methyl ester (intermediate 1A) were dissolved in 5 l dichloromethane at 20° C. 325.6 g (1321 mmol) m-chloroperbenzoic acid (mCPBA) were added in portions over 40 min. The yellow turbid solution was stirred for 30 min at 20-22° C. and heated to 30° C. for 5 h (IPC by HPLC, additional mCPBA can be added if the conversion is not sufficient) then overnight at RT. The reaction mixture was washed twice with half saturated $Na_2CO_3$ (6 l and 4 l), then with 4 l 5% aqueous NaCl solution. The organic phase was treated with 150 ml morpholine (1722 mmol) and stirred at RT for 45 min (peroxide test negative). The orange turbid solution was washed twice with 6 l water, dried over $Na_2SO_4$ and filtered. The filter cake was washed with 1 l dichloromethane. The filtrate was concentrated to an oil. 1 l 2-methoxy-2-methyl-propane was added upon which crystallization started. The suspension was cooled overnight to −10° C. After 10 h at −10° C., the suspension was filtered and washed with cold 2-methoxy-2-methyl-propane. The filter cake was dried under reduced pressure (45° C./10 mbar) to give 222.7 g (81%) of the title compound as colorless crystals. MS: 312.0 (MH$^+$).

B) 6-Hydroxy-3-methyl-5-(3-trifluoromethyl-phenyl)-pyridine-2-carboxylic acid methyl ester; 3-Methyl-6-oxo-5-(3-trifluoromethyl-phenyl)-1,6-dihydro-pyridine-2-carboxylic acid methyl ester (tautomers)

20 g (64.25 mmol) of 3-methyl-1-oxy-5-(3-trifluoromethyl-phenyl)-pyridine-2-carboxylic acid methyl ester were dissolved in 400 ml ethyl acetate. 13.8 ml (103 mmol) 2,4,6-trimethylpyridine were added and the solution was heated to 60° C. 14.6 ml (103 mol) trifluoroacetic anhydride were added over 1 h. After an additional reaction time of 2 h (IPC by HPLC), the reaction mixture was cooled to RT. A solution of 13.1 ml (321 mmol) methanol in 16 ml ethyl acetate was added slowly during which a suspension was obtained. The suspension was stirred at RT for 1 h. About 200 ml solvent were removed at the rotavap and the suspension was stirred for 30 min at RT. The crystals were filtered, washed with ethyl acetate and dried under reduced pressure (50° C./10 mbar) to give 18.04 g (90%) of the title compound as a light yellow powder. MS: 312.0 (MH$^+$).

C) 6-Hydroxy-3-methyl-5-(3-trifluoromethyl-phenyl)-pyridine-2-carboxylic acid; 3-Methyl-6-oxo-5-(3-trifluoromethyl-phenyl)-1,6-dihydro-pyridine-2-carboxylic acid (tautomers)

18 g (57.8 mmol) of 6-hydroxy-3-methyl-5-(3-trifluoromethyl-phenyl)-pyridine-2-carboxylic acid methyl ester/3-methyl-6-oxo-5-(3-trifluoromethyl-phenyl)-1,6-dihydro-pyridine-2-carboxylic acid methyl ester (tautomers) were suspended in 144 ml of THF. 34.7 ml (69.4 mmol) of a 2 M aqueous NaOH solution were added. The resulting solution was heated to 40° C. and stirred at that temperature until complete conversion (ca 7 h, IPC by HPLC). The reaction mixture was cooled to RT. 34.7 ml of a 2 M aqueous HCl solution were added (pH 2) upon which a suspension was obtained. The suspension was stirred for 2 h at RT and filtered. The filter cake was washed with water and dried under reduced pressure (50° C./10 mbar) to give 16.29 g (95%) of the title compound as colorless crystals. MS: 296.0 (M−H⁻).

Example 1

[3-Methyl-5-(3-trifluoromethyl-phenyl)-pyridin-2-yl]-(4-pyrrolidin-1-yl-piperidin-1-yl)-methanone

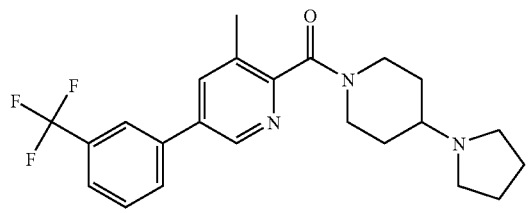

To a solution of 0.42 g (1.5 mmol) of 3-methyl-5-(3-trifluoromethyl-phenyl)-pyridine-2-carboxylic acid (intermediate 1B) in 15 ml of DMF was added 0.60 g (1.6 mmol) of O-(7-azabenzotriazol-1-yl)-N,N,N',N'-tetramethyluronium hexafluorophosphate (HATU) and 0.62 ml=0.45 g (4.5 mmol) of Et₃N; after 30 min, 0.24 g (1.6 mmol) of 4-pyrrolidin-1-yl-piperidine was added. 1 hour later, the reaction mixture was poured into crashed ice and extracted three times with EtOAc; the organic phases were washed with water, dried over magnesium sulfate, filtered and evaporated. The residue was purified by flash column chromatography (CH₂Cl₂/MeOH 95:5 to 4:1) to give 0.56 g (89%) of the title compound as light brown oil. MS: 418.1 (MH⁺).

Example 2

[3-Methyl-1-oxy-5-(3-trifluoromethyl-phenyl)-pyridin-2-yl]-(4-pyrrolidin-1-yl-piperidin-1-yl)-methanone

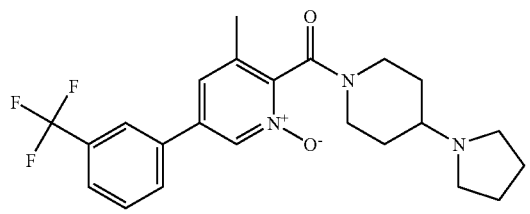

In analogy to the procedure described for example 1, 3-methyl-1-oxy-5-(3-trifluoromethyl-phenyl)-pyridine-2-carboxylic acid (intermediate 1) was reacted with 4-pyrrolidin-1-yl-piperidine to give the title compound as light brown solid. MS: 434.3 (MH⁺).

Example 3

[6-Chloro-3-methyl-5-(3-trifluoromethyl-phenyl)-pyridin-2-yl]-(4-pyrrolidin-1-yl-piperidin-1-yl)-methanone

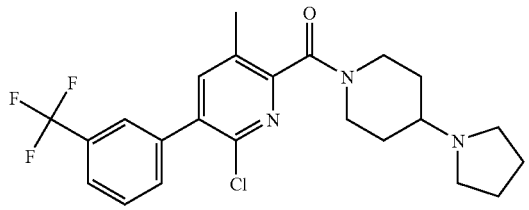

In analogy to the procedure described for example 1, 6-chloro-3-methyl-5-(3-trifluoromethyl-phenyl)-pyridine-2-carboxylic acid [prepared from 6-chloro-3-methyl-5-(3-trifluoromethyl-phenyl)-pyridine-2-carboxylic acid methyl ester (intermediate 2) by saponification in analogy to the procedure described for intermediate 1B] was reacted with 4-pyrrolidin-1-yl-piperidine to give the title compound as light brown solid. MS: 452.1 (MH⁺, 1Cl).

Example 4

[4-Chloro-3-methyl-5-(3-trifluoromethyl-phenyl)-pyridin-2-yl]-(4-pyrrolidin-1-yl-piperidin-1-yl)-methanone

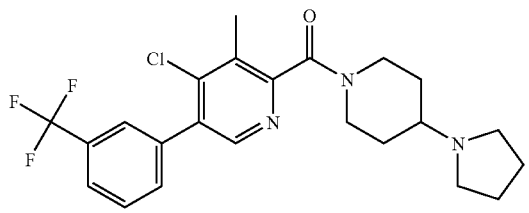

In analogy to the procedure described for example 1, 4-chloro-3-methyl-5-(3-trifluoromethyl-phenyl)-pyridine-2-carboxylic acid [prepared from 4-chloro-3-methyl-5-(3-trifluoromethyl-phenyl)-pyridine-2-carboxylic acid methyl ester (intermediate 3) by saponification in analogy to the procedure described for intermediate 1B] was reacted with 4-pyrrolidin-1-yl-piperidine to give the title compound as colorless solid. MS: 452.1 (MH⁺, 1Cl).

Example 5

[4-((S)-2-Hydroxymethyl-pyrrolidin-1-yl)-piperidin-1-yl]-[3-methyl-5-(3-trifluoromethyl-phenyl)-pyridin-2-yl]-methanone

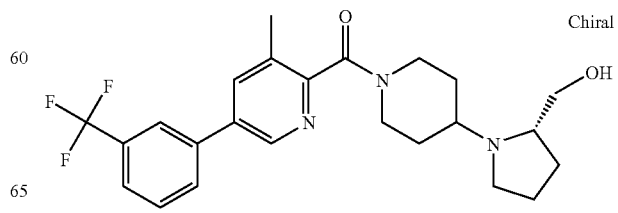

In analogy to the procedures described for example 1 and for intermediate 1B, 3-methyl-5-(3-trifluoromethyl-phenyl)-pyridine-2-carboxylic acid (intermediate 1B) was reacted with benzoic acid (S)-1-piperidin-4-yl-pyrrolidin-2-ylmethyl ester (intermediate 6) to give benzoic acid (S)-1-{1-[3-methyl-5-(3-trifluoromethyl-phenyl)-pyridine-2-carbonyl]-piperidin-4-yl}-pyrrolidin-2-ylmethyl ester, which was subsequently saponified to give the title compound as light brown solid. MS: 448.1 (MH$^+$).

Example 6

[6-(4-Methoxy-benzylamino)-3-methyl-5-(3-trifluoromethyl-phenyl)-pyridin-2-yl]-(4-pyrrolidin-1-yl-piperidin-1-yl)-methanone

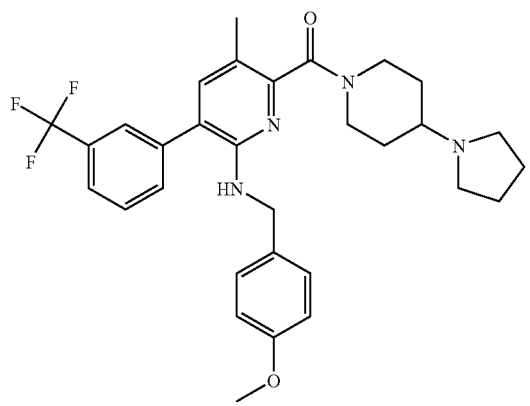

A suspension of 1.25 g (2.8 mmol) of [6-chloro-3-methyl-5-(3-trifluoromethyl-phenyl)-pyridin-2-yl]-(4-pyrrolidin-1-yl-piperidin-1-yl)-methanone (example 3), 0.069 g (0.1 mmol) of [rac]-2,2'-bis(diphenylphosphino)-1,1'-binaphthyl, 0.025 g (0.1 mmol) of palladium(II) acetate and 0.40 g (2.9 mmol) of 4-methoxy-benzylamine in 30 ml of toluene was stirred at RT; 1.08 g (3.3 mmol) of cesium carbonate was added and the reaction mixture subsequently heated up to reflux. After 18 hours, it was cooled down to RT, poured into crashed ice and extracted twice with EtOAc; the organic phases were washed with water, dried over magnesium sulfate, filtered and evaporated. The residue was purified by flash column chromatography (CH$_2$Cl$_2$/MeOH 1:0 to 9:1) to give 1.25 g (82%) of the title compound as light yellow solid. MS: 553.3 (MH$^+$).

Example 7

[6-Amino-3-methyl-5-(3-trifluoromethyl-phenyl)-pyridin-2-yl]-(4-pyrrolidin-1-yl-piperidin-1-yl)-methanone

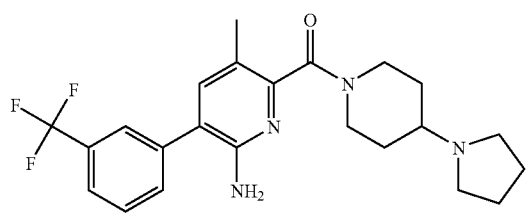

To a solution of 1.48 g (2.7 mmol) of [6-(4-methoxy-benzylamino)-3-methyl-5-(3-trifluoromethyl-phenyl)-pyridin-2-yl]-(4-pyrrolidin-1-yl-piperidin-1-yl)-methanone (example 6) in 75 ml of CH$_2$Cl$_2$ was added 12.2 ml=18.2 g (160 mmol) of trifluoroacetic acid and the reaction mixture was subsequently heated up to reflux. After two hours, it was poured into crashed ice, the pH was adjusted to 8-9 with sodium carbonate solution and it was extracted twice with CH$_2$Cl$_2$; the organic phases were washed with water, dried over magnesium sulfate, filtered and evaporated. The residue was purified by flash column chromatography (CH$_2$Cl$_2$/MeOH 98:2 to 3:1) to give 1.04 g (90%) of the title compound as light yellow foam. MS: 433.3 (MH$^+$).

Example 8

[6-Methoxy-3-methyl-5-(3-trifluoromethyl-phenyl)-pyridin-2-yl]-(4-pyrrolidin-1-yl-piperidin-1-yl)-methanone

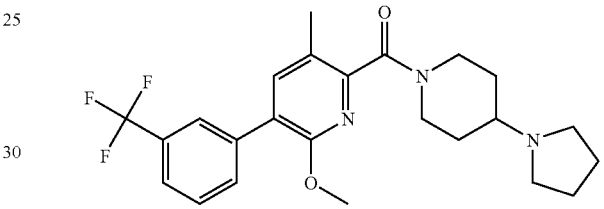

A solution of 0.55 g (1.2 mmol) of [6-chloro-3-methyl-5-(3-trifluoromethyl-phenyl)-pyridin-2-yl]-(4-pyrrolidin-1-yl-piperidin-1-yl)-methanone (example 3) in 10 ml of MeOH was treated with 2.25 ml (12.2 mmol) of a sodium methoxide solution (5.4 molar in MeOH) and the reaction mixture was heated up to reflux. After 18 hours, it was poured into crashed ice and extracted three times with CH$_2$Cl$_2$/2-propanol 4:1; the organic phases were dried over magnesium sulfate, filtered and evaporated. The residue was purified by flash column chromatography (CH$_2$Cl$_2$/MeOH 98:2 to 4:1) to give 0.41 g (76%) of the title compound as light yellow oil. MS: 448.3 (MH$^+$).

Example 9

[6-Hydroxy-3-methyl-5-(3-trifluoromethyl-phenyl)-pyridin-2-yl]-(4-pyrrolidin-1-yl-piperidin-1-yl)-methanone; 5-Methyl-6-(4-pyrrolidin-1-yl-piperidine-1-carbonyl)-3-(3-trifluoromethyl-phenyl)-1H-pyridin-2-one (tautomers)

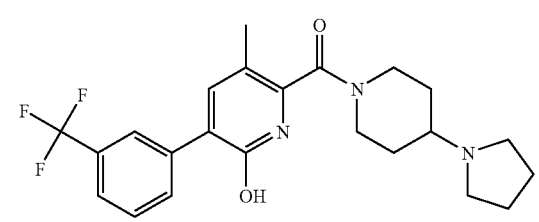

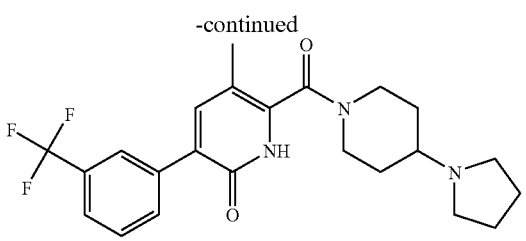

A solution of 0.20 g (0.4 mmol) of [6-methoxy-3-methyl-5-(3-trifluoromethyl-phenyl)-pyridin-2-yl]-(4-pyrrolidin-1-yl-piperidin-1-yl)-methanone (example 8) in 10 ml of $CH_2Cl_2$ was cooled down to 0° C. and 0.89 ml (0.9 mmol) of a solution of boron tribromide (1 molar in $CH_2Cl_2$) was added drop by drop and the reaction mixture was subsequently warmed up to RT. After three hours, 1.0 ml of MeOH was added and 30 min later, it was poured into crashed ice, neutralized with sodium hydrogen carbonate and extracted twice with $CH_2Cl_2$; the organic phases were washed with water, dried over magnesium sulfate, filtered and evaporated. The residue was purified by flash column chromatography ($CH_2Cl_2$/MeOH 98:2 to 3:1) to give 0.077 g (40%) of the title compound as off-white solid. MS: 434.2 (MH$^+$).

Example 10

N-Acetyl-N-[5-methyl-6-(4-pyrrolidin-1-yl-piperidine-1-carbonyl)-3-(3-trifluoromethyl-phenyl)-pyridin-2-yl]-acetamide

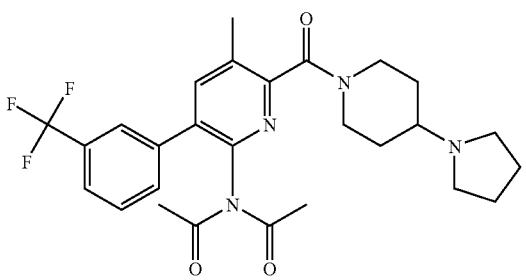

Example 11

N-[5-Methyl-6-(4-pyrrolidin-1-yl-piperidine-1-carbonyl)-3-(3-trifluoromethyl-phenyl)-pyridin-2-yl]-acetamide

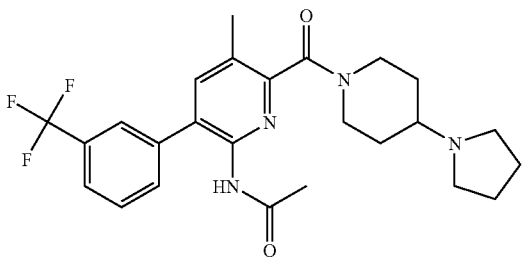

A solution of 0.22 g (0.5 mmol) of [6-amino-3-methyl-5-(3-trifluoromethyl-phenyl)-pyridin-2-yl]-(4-pyrrolidin-1-yl-piperidin-1-yl)-methanone (example 7) in 5 ml of acetone was treated with 0.35 ml=0.26 g (2.5 mmol) of $Et_3N$, followed by 0.19 ml=0.21 g (2.0 mmol) of acetic anhydride and the reaction mixture was subsequently heated up to reflux. After 22 hours, it was poured into crashed ice, the pH was adjusted to 8-9 with sodium carbonate solution and it was extracted twice with EtOAc; the organic phases were washed with water, dried over magnesium sulfate, filtered and evaporated. The residue was purified by flash column chromatography ($CH_2Cl_2$/MeOH 1:0 to 3:2) to give 0.12 g (51%) the N-[5-methyl-6-(4-pyrrolidin-1-yl-piperidine-1-carbonyl)-3-(3-trifluoromethyl-phenyl)-pyridin-2-yl]-acetamide as light yellow solid [MS: 475.2 (MH$^+$)] and 0.098 g (37%) of N-acetyl-N-[5-methyl-6-(4-pyrrolidin-1-yl-piperidine-1-carbonyl)-3-(3-trifluoromethyl-phenyl)-pyridin-2-yl]-acetamide as yellow solid. MS: 517.2 (MH$^+$).

Example 12

N-[5-Methyl-6-(4-pyrrolidin-1-yl-piperidine-1-carbonyl)-3-(3-trifluoromethyl-phenyl)-pyridin-2-yl]-methanesulfonamide

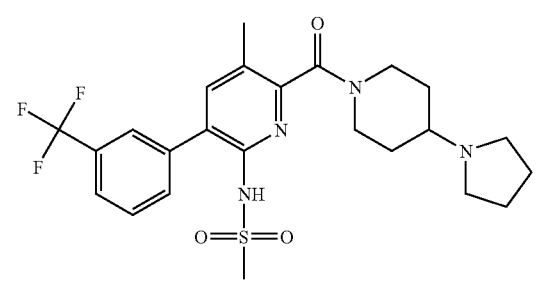

To a solution of 0.13 g (0.2 mmol) of N-{5-methyl-6-[(4-pyrrolidin-1-ylpiperidin-1-yl)carbonyl]-3-[3-(trifluoromethyl)phenyl]pyridin-2-yl}-N-(methylsulfonyl)methanesulfonamide (intermediate 4) in 2.0 ml of THF was added 0.2 ml (0.2 mmol) of a tetrabutylammonium fluoride solution (1M in THF) and the reaction mixture was subsequently heated up to reflux. After 4 days, the solvent was evaporated and the crude product purified by flash column chromatography ($CH_2Cl_2$/MeOH 98:2 to 4:1) to give 0.069 g (64%) of the title compound as yellow amorphous solid. MS: 511.3 (MH$^+$).

Example 13

1,4-Dimethyl-3-(4-pyrrolidin-1-yl-piperidine-1-carbonyl)-6-(3-trifluoromethyl-phenyl)-1H-pyridin-2-one

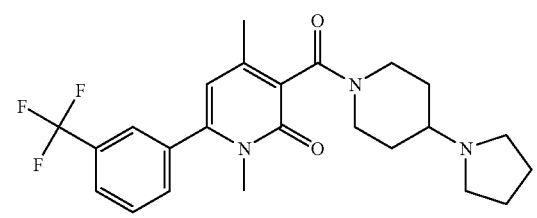

A solution of 0.16 g (0.5 mmol) of 1,4-dimethyl-2-oxo-6-(3-trifluoromethyl-phenyl)-1,2-dihydro-pyridine-3-carboxylic acid (intermediate 5) in 5 ml of CH$_2$Cl$_2$ was treated at RT with two drops of DMF; then, 0.05 ml=0.074 g (0.6 mmol) of oxalyl chloride was added and the reaction mixture was stirred for 30 min at RT. After removal of the solvents by evaporation in a high vacuum, the residue was dissolved again in 10 ml of CH$_2$Cl$_2$ and the solution was cooled down to 0° C.; then, 0.29 ml=0.21 g (2.1 mmol) of Et$_3$N was added while stirring, followed by 0.081 g (0.5 mmol) of 4-pyrrolidin-1-yl-piperidine. The reaction mixture was subsequently warmed up to RT. After 3 hours, it was poured into crashed ice and extracted twice with CH$_2$Cl$_2$; the organic phases were washed with water, dried over magnesium sulfate, filtered and evaporated. The residue was purified by flash column chromatography (CH$_2$Cl$_2$/MeOH 98:2 to 95:5) to give 0.20 g (85%) of the title compound as light yellow solid. MS: 448.2 (MH$^+$).

Example 14

[3-Chloro-5-(3-trifluoromethyl-phenyl)-pyridin-2-yl]-(4-pyrrolidin-1-yl-piperidin-1-yl)-methanone

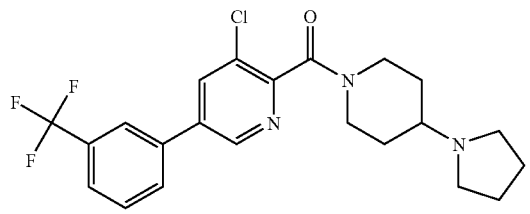

In analogy to the procedure described for example 1, 3-chloro-5-(3-trifluoromethyl-phenyl)-pyridine-2-carboxylic acid [prepared from 3-chloro-5-(3-trifluoromethyl-phenyl)-pyridine-2-carboxylic acid methyl ester (intermediate 7) by saponification in analogy to the procedure described for intermediate 1B] was reacted with 4-pyrrolidin-1-yl-piperidine to give the title compound as light yellow oil. MS: 438.2 (MH$^+$, 1Cl).

Example 15

[3,5-Bis-(3-trifluoromethyl-phenyl)-pyridin-2-yl]-(4-pyrrolidin-1-yl-piperidin-1-yl)-methanone

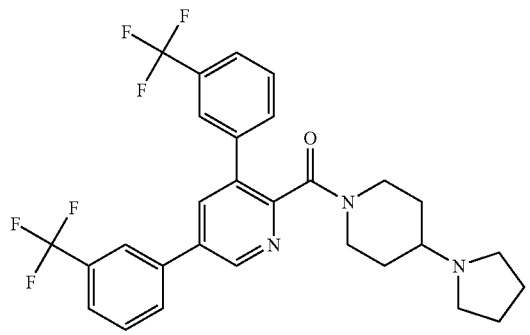

In analogy to the procedure described for example 1, 3,5-bis-(3-trifluoromethyl-phenyl)-pyridine-2-carboxylic acid [prepared from 3,5-bis-(3-trifluoromethyl-phenyl)-pyridine-2-carboxylic acid methyl ester (intermediate 8) by saponification in analogy to the procedure described for intermediate 1B] was reacted with 4-pyrrolidin-1-yl-piperidine to give the title compound as light yellow oil. MS: 548.3 (MH$^+$).

Example 16

[5-Methyl-3-(3-trifluoromethyl-phenyl)-[2,3']bipyridinyl-6-yl]-(4-pyrrolidin-1-yl-piperidin-1-yl)-methanone

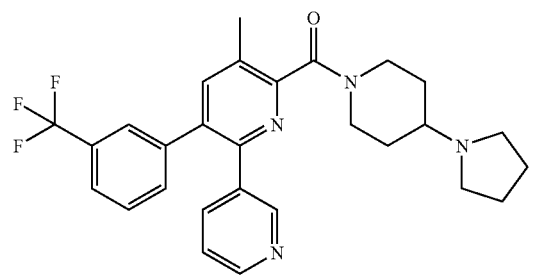

In analogy to the procedure described for the preparation of intermediate 5C, [6-chloro-3-methyl-5-(3-trifluoromethyl-phenyl)-pyridin-2-yl]-(4-pyrrolidin-1-yl-piperidin-1-yl)-methanone (example 3) was reacted with pyridine-3-yl-boronic acid to give the title compound as colorless oil. MS: 495.3 (MH$^+$).

Example 17

[3-Methyl-6-pyrimidin-5-yl-5-(3-trifluoromethyl-phenyl)-pyridin-2-yl]-(4-pyrrolidin-1-yl-piperidin-1-yl)-methanone

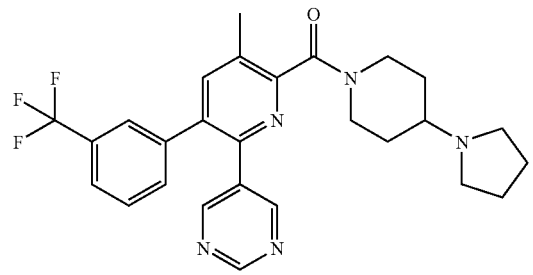

In analogy to the procedure described for the preparation of intermediate 5C, [6-chloro-3-methyl-5-(3-trifluoromethyl-phenyl)-pyridin-2-yl]-(4-pyrrolidin-1-yl-piperidin-1-yl)-methanone (example 3) was reacted with pyrimidine-5-yl-boronic acid to give the title compound as off-white amorphous solid. MS: 496.2 (MH$^+$).

Example 18

[2-(4-Methoxy-benzylamino)-4-methyl-6-(3-trifluoromethyl-phenyl)-pyridin-3-yl]-(4-pyrrolidin-1-yl-piperidin-1-yl)-methanone

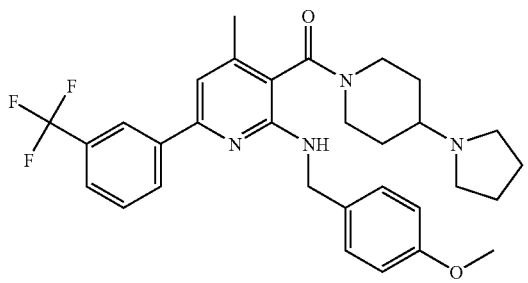

In analogy to the procedure described for the preparation of example 6, trifluoro-methanesulfonic acid 4-methyl-3-(4-pyrrolidin-1-yl-piperidine-1-carbonyl)-6-(3-trifluoromethyl-phenyl)-pyridin-2-yl ester (intermediate 10) was reacted with [rac]-2,2'-bis(diphenylphosphino)-1,1'-binaphthyl, palladium(II) acetate and 4-methoxy-benzylamine to give the title compound as yellow oil. MS: 553.4 (MH$^+$).

Example 19

[2-Amino-4-methyl-6-(3-trifluoromethyl-phenyl)-pyridin-3-yl]-(4-pyrrolidin-1-yl-piperidin-1-yl)-methanone

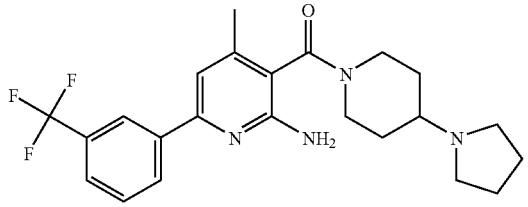

In analogy to the procedure described for the preparation of example 7, [2-(4-methoxy-benzylamino)-4-methyl-6-(3-trifluoromethyl-phenyl)-pyridin-3-yl]-(4-pyrrolidin-1-yl-piperidin-1-yl)-methanone (example 18) was reacted with trifluoroacetic acid to give the title compound as light yellow solid. MS: 433.5 (MH$^+$).

Example 20

[6-(3-Chloro-[1,2,4]triazol-1-yl)-3-methyl-5-(3-trifluoromethyl-phenyl)-pyridin-2-yl]-(4-pyrrolidin-1-yl-piperidin-1-yl)-methanone

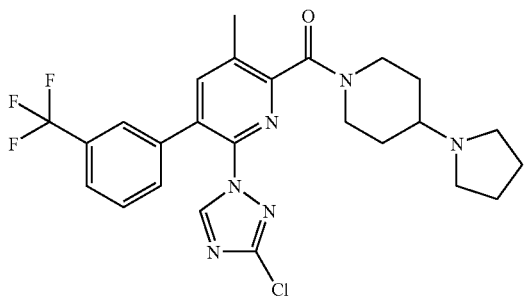

A well stirred solution of 0.17 g (1.59 mmol) of 3-chloro-1H-[1,2,4]triazole in 1.0 ml of 1-methyl-pyrrolidin-2-one was treated at RT with 0.058 g (1.32 mmol) of a sodium hydride (55% in mineral oil). After 30 min, 0.20 g (0.44 mmol) of [6-chloro-3-methyl-5-(3-trifluoromethyl-phenyl)-pyridin-2-yl]-(4-pyrrolidin-1-yl-piperidin-1-yl)-methanone (example 3) was added and the reaction mixture was heated up to 150° C. After 24 hours, it was poured into crashed ice and extracted twice with EtOAc; the organic phases were washed with water, dried over magnesium sulfate, filtered and evaporated. The residue was purified by flash column chromatography (CH$_2$Cl$_2$/MeOH 1:0 to 95:5) to give 0.11 g (48%) of the title compound as yellow oil. MS: 519.3 (MH$^+$, 1Cl).

Example 21

[3,6-Dichloro-5-(3-trifluoromethyl-phenyl)-pyridin-2-yl]-(4-pyrrolidin-1-yl-piperidin-1-yl)-methanone

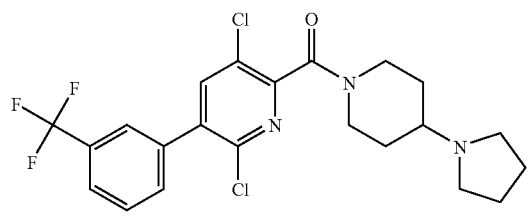

In analogy to the procedure described for the preparation of example 1, 3,6-dichloro-5-(3-trifluoromethyl-phenyl)-pyridine-2-carboxylic acid [prepared from 3,6-dichloro-5-(3-trifluoromethyl-phenyl)-pyridine-2-carboxylic acid methyl ester (intermediate 11) by saponification in analogy to the procedure described for intermediate 1B] was reacted with 4-pyrrolidin-1-yl-piperidine to give the title compound as light yellow amorphous solid. MS: 472.1 (MH$^+$, 2Cl).

Example 22

[3-Chloro-6-methoxy-5-(3-trifluoromethyl-phenyl)-pyridin-2-yl]-(4-pyrrolidin-1-yl-piperidin-1-yl)-methanone

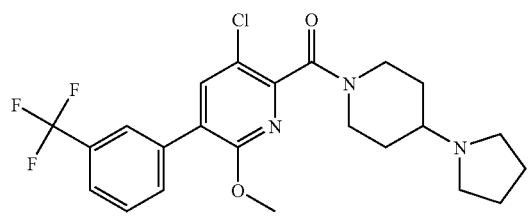

In analogy to the procedure described for the preparation of example 8, [3,6-dichloro-5-(3-trifluoromethyl-phenyl)-pyridin-2-yl]-(4-pyrrolidin-1-yl-piperidin-1-yl)-methanone (example 21) was reacted with sodium methoxide in methanol at 50° C. to give the title compound as light yellow oil. MS: 468.3 (MH$^+$, 1Cl).

Example 23

[3-Chloro-6-hydroxy-5-(3-trifluoromethyl-phenyl)-pyridin-2-yl]-(4-pyrrolidin-1-yl-piperidin-1-yl)-methanone; 5-Chloro-6-(4-pyrrolidin-1-yl-piperidine-1-carbonyl)-3-(3-trifluoromethyl-phenyl)-1H-pyridin-2-one (tautomers)

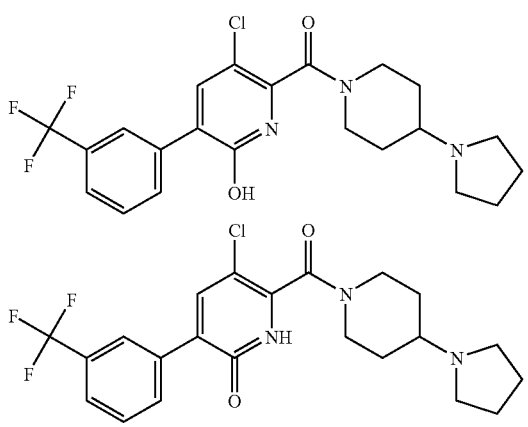

In analogy to the procedure described for the preparation of intermediate 10C, [3-chloro-6-methoxy-5-(3-trifluoromethyl-phenyl)-pyridin-2-yl]-(4-pyrrolidin-1-yl-piperidin-1-yl)-methanone (example 22) was reacted with boron tribromide in $CH_2Cl_2$ at RT to give the title compound as off-white solid. MS: 454.3 ($MH^+$, 1Cl).

Example 24

[6-Ethynyl-3-methyl-5-(3-trifluoromethyl-phenyl)-pyridin-2-yl]-(4-pyrrolidin-1-yl-piperidin-1-yl)-methanone

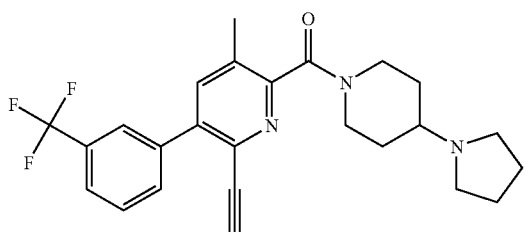

A solution of 0.65 g (1.27 mmol) of [3-methyl-5-(3-trifluoromethyl-phenyl)-6-trimethylsilanylethynyl-pyridin-2-yl]-(4-pyrrolidin-1-yl-piperidin-1-yl)-methanone (intermediate 12) in 12 ml of EtOH/THF (5:1) was treated at RT with 0.35 g (2.53 mmol) of potassium carbonate. After 4 hours, the reaction mixture was poured into crashed ice, the pH was adjusted to 3-4 with hydrochloric acid (2 molar) and the mixture was extracted three times with $CH_2Cl_2$; the organic phases were washed with water, dried over magnesium sulfate, filtered and evaporated. The residue was purified by flash column chromatography ($CH_2Cl_2$/MeOH 1:0 to 9:1) to give 0.439 g (79%) of the title compound as brown solid. MS: 442.3 ($MH^+$).

Example 25

[3-Methyl-6-[1,2,4]triazol-1-yl-5-(3-trifluoromethyl-phenyl)-pyridin-2-yl]-(4-pyrrolidin-1-yl-piperidin-1-yl)-methanone

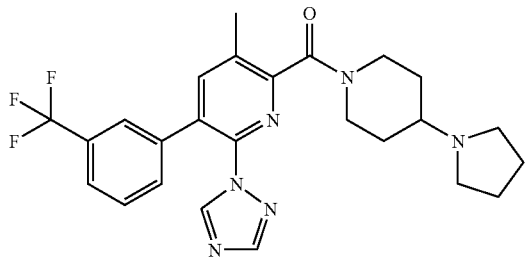

In analogy to the procedure described for the preparation of example 20, [6-chloro-3-methyl-5-(3-trifluoromethyl-phenyl)-pyridin-2-yl]-(4-pyrrolidin-1-yl-piperidin-1-yl)-methanone (example 3) was reacted with 1H-[1,2,4]triazole and sodium hydride in 1-methyl-pyrrolidin-2-one at reflux to give the title compound as colorless solid. MS: 485.3 ($MH^+$).

Example 26

[6-(2-Amino-ethylamino)-3-methyl-5-(3-trifluoromethyl-phenyl)-pyridin-2-yl]-(4-pyrrolidin-1-yl-piperidin-1-yl)-methanone

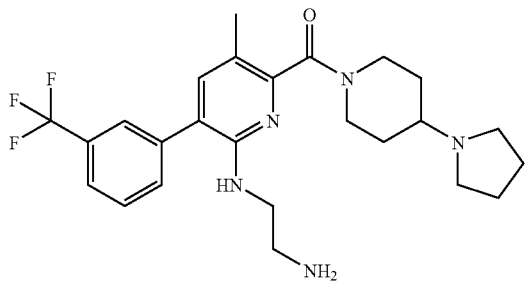

In analogy to the procedure described for the preparation of example 6, [6-chloro-3-methyl-5-(3-trifluoromethyl-phenyl)-pyridin-2-yl]-(4-pyrrolidin-1-yl-piperidin-1-yl)-methanone (example 3) was reacted with ethane-1,2-diamine, [rac]-2,2'-bis(diphenylphosphino)-1,1'-binaphthyl, palladium(II) acetate and cesium carbonate in toluene at reflux to give the title compound as light yellow solid. MS: 476.3 ($MH^+$).

Example 27

[6-(2-Hydroxy-ethylamino)-3-methyl-5-(3-trifluoromethyl-phenyl)-pyridin-2-yl]-(4-pyrrolidin-1-yl-piperidin-1-yl)-methanone

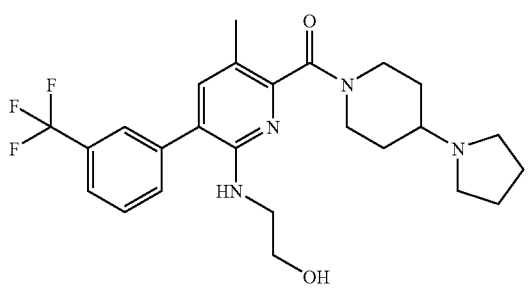

A solution of 0.14 g (0.25 mmol) of [6-(2-benzyloxy-ethylamino)-3-methyl-5-(3-trifluoromethyl-phenyl)-pyridin-2-yl]-(4-pyrrolidin-1-yl-piperidin-1-yl)-methanone (intermediate 14) in 6.0 ml of MeOH was treated at RT with 0.49 ml (0.49 mmol) of hydrochloric acid (1.0 molar in MeOH), followed by 0.026 g (0.025 mmol) of Pd—C (10%). The reaction mixture was vigorously stirred in an atmosphere of hydrogen for 3 hours. After filtration through dicalite, the solvent was removed by evaporation, then the residue was dissolved in $H_2O/Na_2CO_3$ and extracted twice with $CH_2Cl_2$; the organic phases were washed with water, dried over magnesium sulfate, filtered and evaporated. The residue was purified by flash column chromatography ($CH_2Cl_2$/MeOH 1:0 to 95:5) to give 0.091 g (77%) of the title compound as yellow amorphous solid. MS: 477.3 (MH$^+$).

Example 28

[5-(3,4-Dichloro-phenyl)-3-methyl-pyridin-2-yl]-(4-pyrrolidin-1-yl-piperidin-1-yl)-methanone

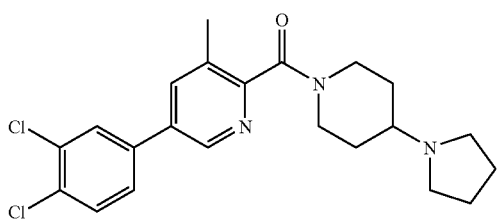

In analogy to the procedure described for the preparation of intermediate 1A, (5-bromo-3-methyl-pyridin-2-yl)-(4-pyrrolidin-1-yl-piperidin-1-yl)-methanone (prepared from 5-bromo-3-methyl-pyridine-2-carboxylic acid methyl ester [Wu, G. G.; Wong, Y.-S.; Poirier, M. *Organic Letters* (1999), 1(5), 745-747], 4-pyrrolidin-1-yl-piperidine, Et$_3$N and HATU in DMF in analogy to the procedure described for the preparation of example 1) was reacted with 3,4-dichlorophenyl-boronic acid, (1,1'-bis-diphenylphosphino)-ferrocene)palladium-(II)dichloride (1:1 complex with $CH_2Cl_2$) and sodium carbonate in dioxane/water to give the title compound as off-white amorphous solid. MS: 418.1 (MH$^-$, 2Cl).

Example 29

[3-Methyl-5-(2-trifluoromethyl-phenyl)-pyridin-2-yl]-(4-pyrrolidin-1-yl-piperidin-1-yl)-methanone

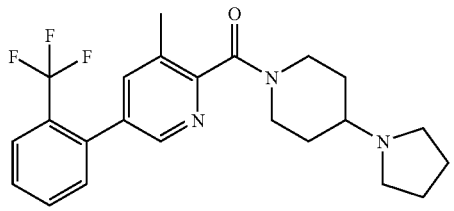

In analogy to the procedure described for the preparation of intermediate 1A, (5-bromo-3-methyl-pyridin-2-yl)-(4-pyrrolidin-1-yl-piperidin-1-yl)-methanone (see example 28) was reacted with 2-trifluoromethyl-phenyl-boronic acid, (1,1'-bis-diphenylphosphino)-ferrocene)palladium-(II)dichloride (1:1 complex with $CH_2Cl_2$) and sodium carbonate in dioxane/water to give the title compound as off-white amorphous solid. MS: 418.2 (MH$^+$).

Example 30

[5-(2-Chloro-5-trifluoromethyl-phenyl)-3-methyl-pyridin-2-yl]-(4-pyrrolidin-1-yl-piperidin-1-yl)-methanone

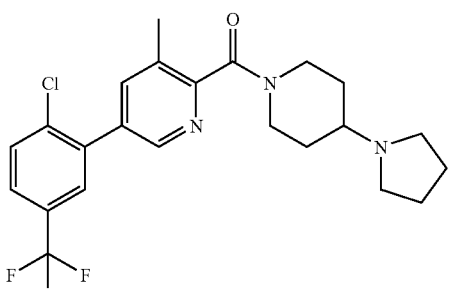

In analogy to the procedure described for the preparation of intermediate 1A, (5-bromo-3-methyl-pyridin-2-yl)-(4-pyrrolidin-1-yl-piperidin-1-yl)-methanone (see example 28) was reacted with 2-chloro-5-trifluoromethyl-phenyl-boronic acid, (1,1'-bis-diphenylphosphino)-ferrocene)palladium-(II) dichloride (1:1 complex with $CH_2Cl_2$) and sodium carbonate in dioxane/water to give the title compound as light brown amorphous solid. MS: 452.2 (MH$^+$, 1Cl).

Example 31

[5-(2-Fluoro-5-trifluoromethyl-phenyl)-3-methyl-pyridin-2-yl]-(4-pyrrolidin-1-yl-piperidin-1-yl)-methanone

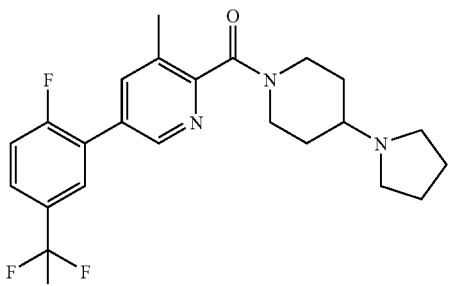

In analogy to the procedure described for the preparation of intermediate 1A, (5-bromo-3-methyl-pyridin-2-yl)-(4-pyrrolidin-1-yl-piperidin-1-yl)-methanone (see example 28) was reacted with 2-fluoro-5-trifluoromethyl-phenyl-boronic acid, (1,1'-bis-diphenylphosphino)-ferrocene)palladium-(II) dichloride (1:1 complex with $CH_2Cl_2$) and sodium carbonate in dioxane/water to give the title compound as brown amorphous solid. MS: 436.3 (MH$^+$).

Example 32

[3-Methyl-6-(1H-[1,2,3]triazol-4-yl)-5-(3-trifluoromethyl-phenyl)-pyridin-2-yl]-(4-pyrrolidin-1-yl-piperidin-1-yl)-methanone

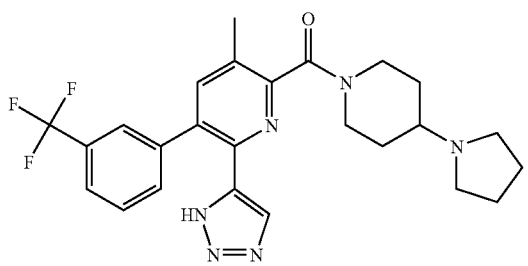

0.30 g (0.50 mmol) of [6-[1-(4-methoxy-benzyl)-1H-[1,2,3]triazol-4-yl]-3-methyl-5-(3-trifluoromethyl-phenyl)-pyridin-2-yl]-(4-pyrrolidin-1-yl-piperidin-1-yl)-methanone (intermediate 13) in 3.2 ml of trifluoroacetic acid were stirred at reflux for 23 hours. The reaction mixture was then poured into crashed ice, the pH was adjusted to 8-9 with aqueous $Na_2CO_3$ and the mixture was extracted twice with $CH_2Cl_2$; the organic phases were washed with water, dried over magnesium sulfate, filtered and evaporated. The residue was purified by flash column chromatography ($CH_2Cl_2$/MeOH 98:2 to 4:1) to give 0.19 g (77%) of the title compound as an off-white solid. MS: 485.4 ($MH^+$).

Example 33

[5-(2-Methoxy-5-trifluoromethyl-phenyl)-3-methyl-pyridin-2-yl]-(4-pyrrolidin-1-yl-piperidin-1-yl)-methanone

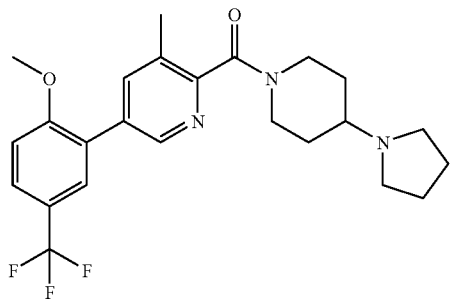

In analogy to the procedure described for the preparation of intermediate 1A, (5-bromo-3-methyl-pyridin-2-yl)-(4-pyrrolidin-1-yl-piperidin-1-yl)-methanone (see example 28) was reacted with 2-methoxy-5-trifluoromethyl-phenyl-boronic acid, (1,1'-bis-diphenylphosphino)-ferrocene)palladium-(II) dichloride (1:1 complex with $CH_2Cl_2$) and sodium carbonate in dioxane/water to give the title compound as brown amorphous solid. MS: 448.1 ($MH^+$).

Example 34

[5-(4-Fluoro-3-trifluoromethyl-phenyl)-3-methyl-pyridin-2-yl]-(4-pyrrolidin-1-yl-piperidin-1-yl)-methanone

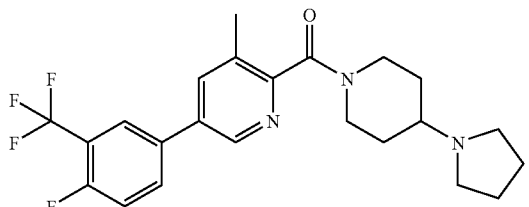

In analogy to the procedure described for the preparation of intermediate 1A, (5-bromo-3-methyl-pyridin-2-yl)-(4-pyrrolidin-1-yl-piperidin-1-yl)-methanone (see example 28) was reacted with 4-fluoro-3-trifluoromethyl-phenyl-boronic acid, (1,1'-bis-diphenylphosphino)-ferrocene)palladium-(II) dichloride (1:1 complex with $CH_2Cl_2$) and sodium carbonate in dioxane/water to give the title compound as brown amorphous solid. MS: 436.4 ($MH^+$).

Example 35

[5-(4-Methoxy-3-trifluoromethyl-phenyl)-3-methyl-pyridin-2-yl]-(4-pyrrolidin-1-yl-piperidin-1-yl)-methanone

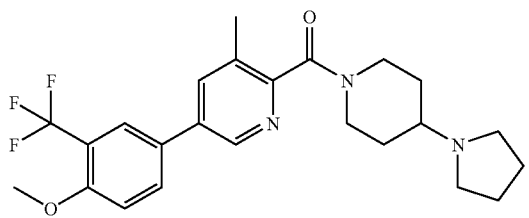

In analogy to the procedure described for the preparation of intermediate 1A, (5-bromo-3-methyl-pyridin-2-yl)-(4-pyrrolidin-1-yl-piperidin-1-yl)-methanone (see example 28) was reacted with 4-methoxy-3-trifluoromethyl-phenyl-boronic acid, (1,1'-bis-diphenylphosphino)-ferrocene)palladium-(II) dichloride (1:1 complex with $CH_2Cl_2$) and sodium carbonate in dioxane/water to give the title compound as brown amorphous solid. MS: 448.2 ($MH^+$).

Example 36

[5-(2-Fluoro-3-trifluoromethyl-phenyl)-3-methyl-pyridin-2-yl]-(4-pyrrolidin-1-yl-piperidin-1-yl)-methanone

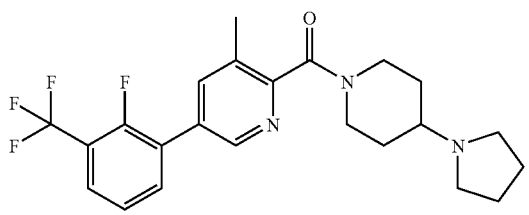

In analogy to the procedure described for the preparation of intermediate 1A, (5-bromo-3-methyl-pyridin-2-yl)-(4-pyrrolidin-1-yl-piperidin-1-yl)-methanone (see example 28) was reacted with 2-fluoro-3-trifluoromethyl-phenyl-boronic acid, (1,1'-bis-diphenylphosphino)-ferrocene)palladium-(II) dichloride (1:1 complex with CH$_2$Cl$_2$) and sodium carbonate in dioxane/water to give the title compound as brown amorphous solid. MS: 436.4 (MH$^+$).

Example 37

[5-(3-Fluoro-5-trifluoromethyl-phenyl)-3-methyl-pyridin-2-yl]-(4-pyrrolidin-1-yl-piperidin-1-yl)-methanone

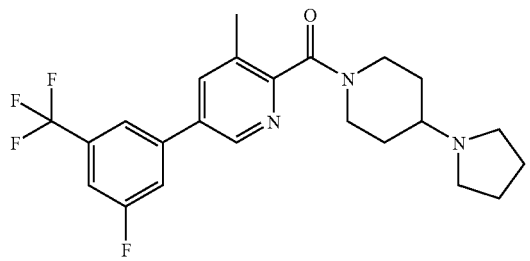

In analogy to the procedure described for the preparation of intermediate 1A, (5-bromo-3-methyl-pyridin-2-yl)-(4-pyrrolidin-1-yl-piperidin-1-yl)-methanone (see example 28) was reacted with 3-fluoro-5-trifluoromethyl-phenyl-boronic acid, (1,1'-bis-diphenylphosphino)-ferrocene)palladium-(II) dichloride (1:1 complex with CH$_2$Cl$_2$) and sodium carbonate in dioxane/water to give the title compound as brown amorphous solid. MS: 436.4 (MH$^+$).

Example 38

[6-Hydroxy-3-methyl-5-(3-trifluoromethyl-phenyl)-pyridin-2-yl]-(4-pyrrolidin-1-yl-piperidin-1-yl)-methanone; 5-Methyl-6-(4-pyrrolidin-1-yl-piperidine-1-carbonyl)-3-(3-trifluoromethyl-phenyl)-1H-pyridin-2-one (tautomers)

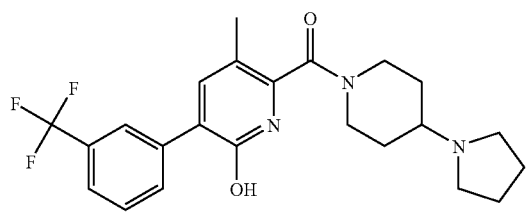

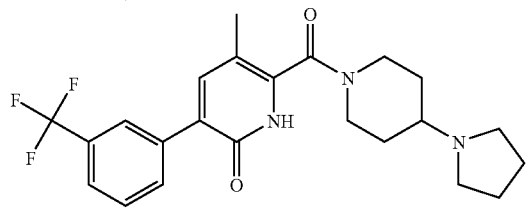

Coupling: 2.5 g (8.4 mmol) of 6-hydroxy-3-methyl-5-(3-trifluoromethyl-phenyl)-pyridine-2-carboxylic acid/3-methyl-6-oxo-5-(3-trifluoromethyl-phenyl)-1,6-dihydro-pyridine-2-carboxylic acid (tautomers) (intermediate 15C) were suspended in a mixture of 37.5 ml acetonitrile and 6.25 ml DMF. 1.48 g (8.8 mmol) carbonyl diimidazole (CDI) was added. The suspension was stirred at RT overnight. 1.43 g (9.25 mmol) 4-(1-pyrrolidinyl)-piperidine was added upon which a yellow suspension was obtained which quickly changed into a colorless suspension. After 3 h at RT (IPC by HPLC), 0.586 ml triethylamine (4.2 mmol) was added. After 2 h at RT, 25 ml water was added. Acetonitrile was removed at the rotavap during which a yellow solution was obtained which changed to a colorless suspension. The suspension was stirred 1 h at RT and 1 h at 0° C. The suspension was filtered. The filter cake was washed with cold water and dried under reduced pressure (50° C./10 mbar) to give 3.02 g of crude title compound as a colorless powder.

Digestion: 15.78 g of the crude title compound were suspended in 158 ml water. The suspension was heated to 100° C. for 20 min and slowly cooled overnight to RT. The suspension was further cooled to 0-5° C. for 1h and was filtered. The filter cake was washed with cold water and dried under reduced pressure (50° C./10 mbar) to give 13.76 g (72%) of the title compound as a colorless powder. MS: 434.4 (MH).

Example 39

[6-(2-Amino-pyrimidin-5-yl)-3-methyl-5-(3-trifluoromethyl-phenyl)-pyridin-2-yl]-(4-pyrrolidin-1-yl-piperidin-1-yl)-methanone

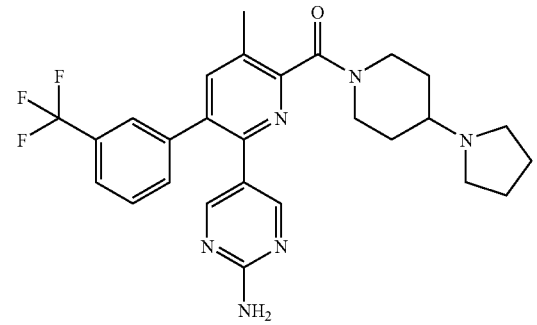

In analogy to the procedure described for the preparation of intermediate 1A, [6-chloro-3-methyl-5-(3-trifluoromethyl-phenyl)-pyridin-2-yl]-(4-pyrrolidin-1-yl-piperidin-1-yl)-methanone (example 3) was reacted with 2-aminopyrimidin-5-yl-boronic acid, (1,1'-bis-diphenylphosphino)-ferrocene) palladium-(II)dichloride (1:1 complex with CH$_2$Cl$_2$) and sodium carbonate in dioxane/water at 80° C. to give the title compound as dark brown oil. MS: 511.4 (MH$^+$).

Example 40

[6'-Amino-5-methyl-3-(3-trifluoromethyl-phenyl)-[2,3']bipyridinyl-6-yl]-(4-pyrrolidin-1-yl-piperidin-1-yl)-methanone

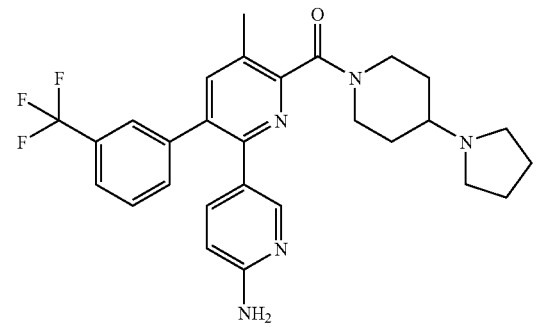

In analogy to the procedure described for the preparation of intermediate 5C, [6-chloro-3-methyl-5-(3-trifluoromethyl-phenyl)-pyridin-2-yl]-(4-pyrrolidin-1-yl-piperidin-1-yl)-methanone (example 3) was reacted with 5-(4,4,5,5-tetramethyl-[1,3,2]dioxaborolan-2-yl)-pyridin-2-ylamine to give the title compound as off-white solid. MS: 510.4 (MH$^+$).

Example 41

[6'-Hydroxy-5-methyl-3-(3-trifluoromethyl-phenyl)-[2,3']bipyridinyl-6-yl]-(4-pyrrolidin-1-yl-piperidin-1-yl)-methanone

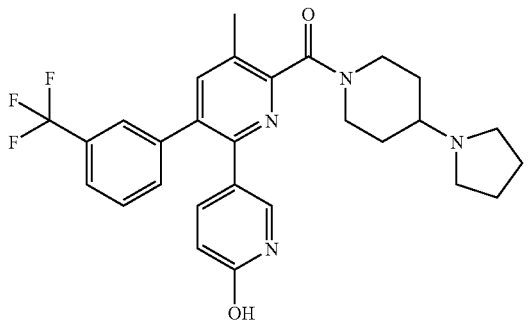

In analogy to the procedure described for the preparation of intermediate 5C, [6-chloro-3-methyl-5-(3-trifluoromethyl-phenyl)-pyridin-2-yl]-(4-pyrrolidin-1-yl-piperidin-1-yl)-methanone (example 3) was reacted with 5-(4,4,5,5-tetramethyl-[1,3,2]dioxaborolan-2-yl)-pyridin-2-ol to give the title compound as yellow amorphous solid. MS: 511.2 (MH$^+$).

Example 42

5-Methyl-6-(4-pyrrolidin-1-yl-piperidine-1-carbonyl)-3-(3-trifluoromethyl-phenyl)-pyridine-2-carbonitrile

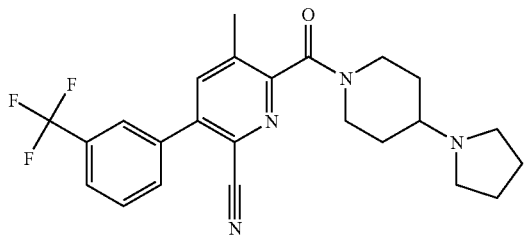

Example 43

5-Methyl-6-(4-pyrrolidin-1-yl-piperidine-1-carbonyl)-3-(3-trifluoromethyl-phenyl)-pyridine-2-carboxylic acid amide

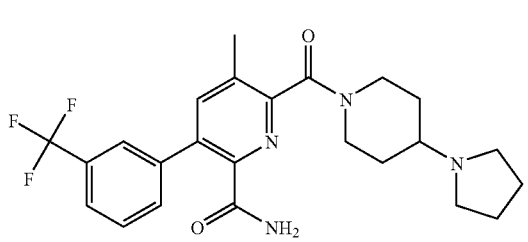

A well stirred suspension of 0.30 g (0.66 mmol) of [6-chloro-3-methyl-5-(3-trifluoromethyl-phenyl)-pyridin-2-yl]-(4-pyrrolidin-1-yl-piperidin-1-yl)-methanone (example 3) and 0.098 g (2.0 mmol) of sodium cyanide in 5.0 ml of 1-methyl-pyrrolidin-2-one was heated for 16 hours at 150° C. After cooling down to RT, the reaction mixture was poured into crashed ice/NaCl-solution (sat. in H$_2$O) and extracted three times with CH$_2$Cl$_2$; the organic phases were washed with water, dried over magnesium sulfate, filtered and evaporated. The residue was purified by flash column chromatography (CH$_2$Cl$_2$/MeOH 1:0 to 4:1) to give 0.086 g (29%) of 5-methyl-6-(4-pyrrolidin-1-yl-piperidine-1-carbonyl)-3-(3-trifluoromethyl-phenyl)-pyridine-2-carbonitrile as light yellow solid. MS: 443.4 (MH$^+$); and 0.045 g (15%) of 5-methyl-6-(4-pyrrolidin-1-yl-piperidine-1-carbonyl)-3-(3-trifluoromethyl-phenyl)-pyridine-2-carboxylic acid amide as light yellow solid. MS: 461.4 (MH$^+$).

Example 44

[6-(2-Methoxy-pyrimidin-5-yl)-3-methyl-5-(3-trifluoromethyl-phenyl)-pyridin-2-yl]-(4-pyrrolidin-1-yl-piperidin-1-yl)-methanone

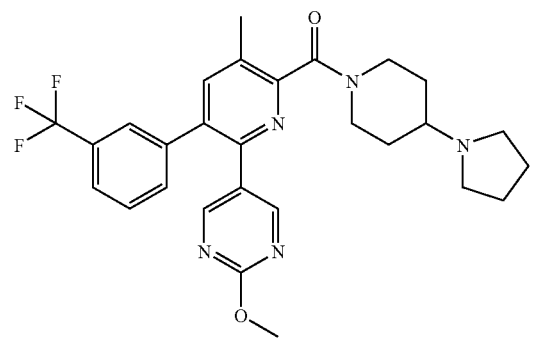

In analogy to the procedure described for the preparation of intermediate 5C, [6-chloro-3-methyl-5-(3-trifluoromethyl-phenyl)-pyridin-2-yl]-(4-pyrrolidin-1-yl-piperidin-1-yl)-methanone (example 3) was reacted with 2-methoxypyrimidin-5-yl-boronic acid to give the title compound as light brown amorphous solid. MS: 526.2 (MH$^+$).

Example 45

5-Methyl-6-(4-pyrrolidin-1-yl-piperidine-1-carbonyl)-3-(3-trifluoromethyl-phenyl)-pyridine-2-carboxylic acid methyl ester

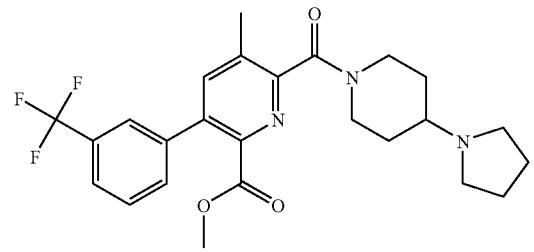

To a degassed solution of 7.00 g (15.5 mmol) of [6-chloro-3-methyl-5-(3-trifluoromethyl-phenyl)-pyridin-2-yl]-(4-pyrrolidin-1-yl-piperidin-1-yl)-methanone (example 3) in 180 ml of MeOH/EtOAc 1:1 were added 0.70 g (0.86 mmol) of (1,1'-bis-diphenylphosphino)-ferrocene)palladium-(II) dichloride (1:1 complex with $CH_2Cl_2$) and 5.4 ml=3.92 g (38.7 mmol) of $Et_3N$. This reaction mixture was stirred in an autoclave and in a carbon monoxide atmosphere at 130° C./70 bar for 30 hours. Then, it was evaporated, the residue dissolved in $H_2O$/EtOAc and extracted twice with EtOAc; the organic phases were washed with water, dried over magnesium sulfate, filtered and evaporated. The residue was purified by flash column chromatography ($CH_2Cl_2$/MeOH 1:0 to 4:1) to give 4.61 g (63%) of the title compound as light brown foam. MS: 476.2 ($MH^+$).

Example 46

[6-Hydroxymethyl-3-methyl-5-(3-trifluoromethyl-phenyl)-pyridin-2-yl]-(4-pyrrolidin-1-yl-piperidin-1-yl)-methanone

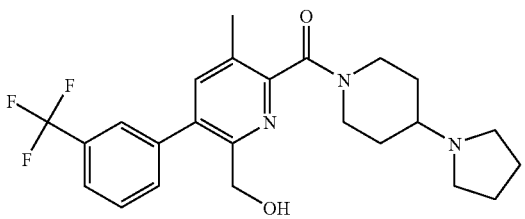

To a solution of 0.24 g (0.51 mmol) of 5-methyl-6-(4-pyrrolidin-1-yl-piperidine-1-carbonyl)-3-(3-trifluoromethyl-phenyl)-pyridine-2-carboxylic acid methyl ester (example 45) in 5.0 ml of EtOH were added 0.093 g (4.27 mmol) of lithium borohydride in three portions. The reaction mixture was stirred at RT for 48 hours, then poured into crashed ice, the pH was reduced to 2-3 with hydrochloric acid (25%), and the mixture subsequently neutralized with solid $NaHCO_3$. Then, it was extracted twice with $CH_2Cl_2$; the organic phases were washed with water, dried over magnesium sulfate, filtered and evaporated. The residue was purified by flash column chromatography ($CH_2Cl_2$/MeOH 1:0 to 9:1) to give 0.097 g (43%) of the title compound as light yellow solid. MS: 448.1 ($MH^+$).

Example 47

5-Methyl-6-(4-pyrrolidin-1-yl-piperidine-1-carbonyl)-3-(3-trifluoromethyl-phenyl)-pyridine-2-carboxylic acid

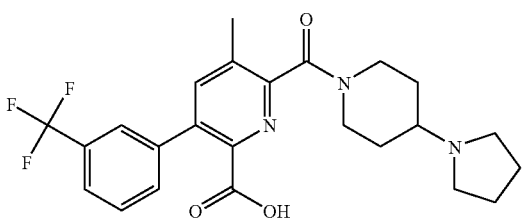

To a solution of 0.315 g (0.66 mmol) of 5-methyl-6-(4-pyrrolidin-1-yl-piperidine-1-carbonyl)-3-(3-trifluoromethyl-phenyl)-pyridine-2-carboxylic acid methyl ester (example 45) in 10 ml of THF/MeOH 1:1 were added 1.32 ml of lithium hydroxide (1 molar in $H_2O$) and the reaction mixture was stirred at RT for 28 hours. Then, the solvents were evaporated and the residue was dissolved in $H_2O$/$CH_2Cl_2$, neutralized with the help of hydrochloric acid and solid $NaHCO_3$ and then extracted four times with $CH_2Cl_2$/2-propanol 3:1; the organic phases were dried over magnesium sulfate, filtered and evaporated, to give 0.188 g (62%) of the title compound as off-white solid. MS: 462.3 ($MH^+$).

Example 48

[3-Methyl-6-(1H-pyrazol-4-yl)-5-(3-trifluoromethyl-phenyl)-pyridin-2-yl]-(4-pyrrolidin-1-yl-piperidin-1-yl)-methanone

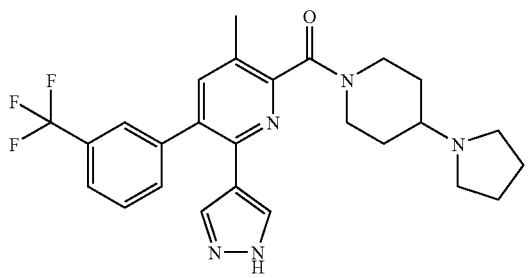

In analogy to the procedure described for the preparation of intermediate 5C, [6-chloro-3-methyl-5-(3-trifluoromethyl-phenyl)-pyridin-2-yl]-(4-pyrrolidin-1-yl-piperidin-1-yl)-methanone (example 3) was reacted with 4-(4,4,5,5-tetramethyl-[1,3,2]dioxaborolan-2-yl)-1H-pyrazole to give the title compound as colorless amorphous solid. MS: 484.2 ($MH^+$).

Example 49

[3-Methyl-6-(1H-pyrazol-3-yl)-5-(3-trifluoromethyl-phenyl)-pyridin-2-yl]-(4-pyrrolidin-1-yl-piperidin-1-yl)-methanone

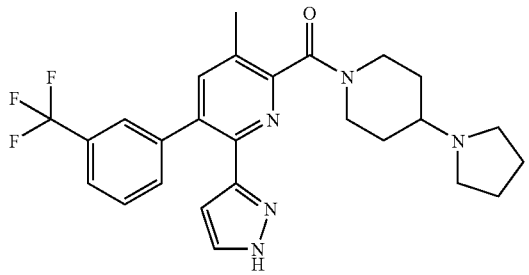

In analogy to the procedure described for the preparation of intermediate 1A, [6-chloro-3-methyl-5-(3-trifluoromethyl-phenyl)-pyridin-2-yl]-(4-pyrrolidin-1-yl-piperidin-1-yl)-methanone (example 3) was reacted with 3-(4,4,5,5-tetramethyl-[1,3,2]dioxaborolan-2-yl)-1H-pyrazole, (1,1'-bis-diphenylphosphino)-ferrocene)palladium-(II)dichloride (1:1 complex with CH$_2$Cl$_2$) and sodium carbonate in dioxane/water at 120° C. to give the title compound as colorless solid. MS: 484.2 (MH$^+$)

Example 50

[3-Methyl-6-(1-methyl-1H-pyrazol-4-yl)-5-(3-trifluoromethyl-phenyl)-pyridin-2-yl]-(4-pyrrolidin-1-yl-piperidin-1-yl)-methanone

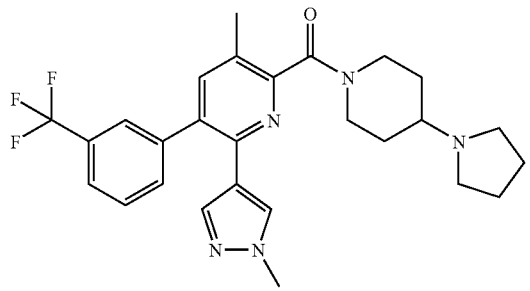

In analogy to the procedure described for the preparation of intermediate 5C, [6-chloro-3-methyl-5-(3-trifluoromethyl-phenyl)-pyridin-2-yl]-(4-pyrrolidin-1-yl-piperidin-1-yl)-methanone (example 3) was reacted with 1-methyl-4-(4,4,5,5-tetramethyl-[1,3,2]dioxaborolan-2-yl)-1H-pyrazole to give the title compound as colorless solid. MS: 498.2 (MH$^+$).

Example 51

[3-Methyl-6-pyrazin-2-yl-5-(3-trifluoromethyl-phenyl)-pyridin-2-yl]-(4-pyrrolidin-1-yl-piperidin-1-yl)-methanone

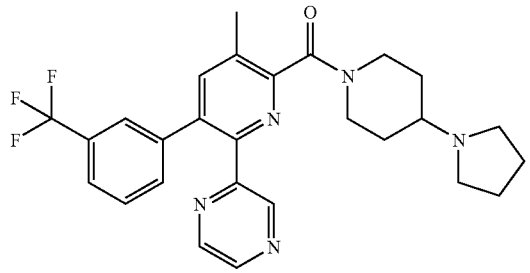

To a degassed solution of 0.20 g (0.44 mmol) of [6-chloro-3-methyl-5-(3-trifluoromethyl-phenyl)-pyridin-2-yl]-(4-pyrrolidin-1-yl-piperidin-1-yl)-methanone (example 3) in 8.0 ml of DMF was added 0.051 g (0.044 mmol) of tetrakis-(triphenylphosphine)-palladium and the reaction mixture was stirred for 20 min at RT. Then, 0.49 g (1.32 mmol) of 2-tributylstannanyl-pyrazine were added and the reaction was heated up to 100° C. After 6 hours, it was cooled down to RT, poured into crashed ice and extracted three times with EtOAc; the organic phases were washed with water, dried over magnesium sulfate, filtered and evaporated. The residue was purified by flash column chromatography (CH$_2$Cl$_2$/MeOH 1:0 to 9:1) to give 0.11 g (50%) of the title compound as yellow oil. MS: 496.2 (MH$^-$).

Example 52

[6-(2-Hydroxy-pyrimidin-5-yl)-3-methyl-5-(3-trifluoromethyl-phenyl)-pyridin-2-yl]-(4-pyrrolidin-1-yl-piperidin-1-yl)-methanone

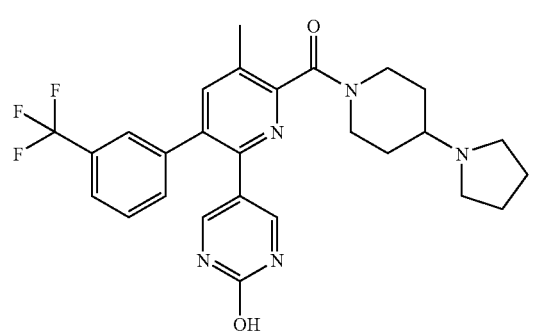

In analogy to the procedure described for the preparation of intermediate 10C, [6-(2-methoxy-pyrimidin-5-yl)-3-methyl-5-(3-trifluoromethyl-phenyl)-pyridin-2-yl]-(4-pyrrolidin-1-yl-piperidin-1-yl)-methanone (example 44) was reacted with boron tribromide in dichloromethane to give the title compound as light yellow solid. MS: 512.2 (MH$^+$).

Example 53

[3-Methyl-6-(2-methyl-2H-pyrazol-3-yl)-5-(3-trifluoromethyl-phenyl)-pyridin-2-yl]-(4-pyrrolidin-1-yl-piperidin-1-yl)-methanone

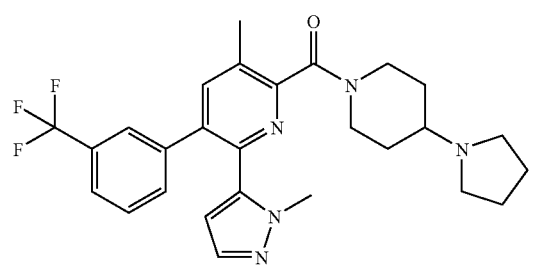

In analogy to the procedure described for the preparation of intermediate 1A, [6-chloro-3-methyl-5-(3-trifluoromethyl-phenyl)-pyridin-2-yl]-(4-pyrrolidin-1-yl-piperidin-1-yl)-methanone (example 3) was reacted with 5-(5,5-dimethyl-[1,

Example 54

[6-(2,4-Dihydroxy-pyrimidin-5-yl)-3-methyl-5-(3-trifluoromethyl-phenyl)-pyridin-2-yl]-(4-pyrrolidin-1-yl-piperidin-1-yl)-methanone

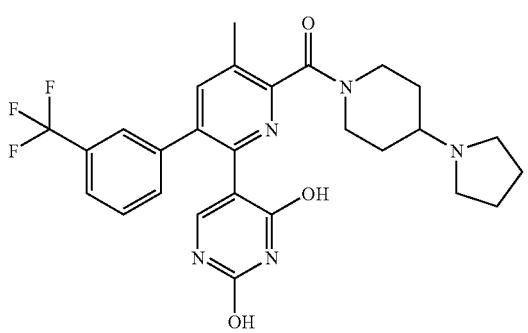

To a degassed solution of 0.20 g (0.44 mmol) of [6-chloro-3-methyl-5-(3-trifluoromethyl-phenyl)-pyridin-2-yl]-(4-pyrrolidin-1-yl-piperidin-1-yl)-methanone (example 3) in 10 ml of 1,2-dimethoxyethane was added 0.138 g (0.88 mmol) of 2,4-dihydroxy-pyrimidine-5-boronic acid, 0.051 g (0.044 mmol) of tetrakis-(triphenylphosphine)-palladium and 0.031 g (0.088 mmol) of 2-(dicyclohexylphosphino)biphenyl, followed by 0.071 g (0.67 mmol) of sodium carbonate and 3.4 ml of H$_2$O. Finally, the reaction mixture was warmed up to 80° C. After 48 hours, it was cooled down to RT, poured into crashed ice and extracted twice with EtOAc; the organic phases were washed with water, dried over magnesium sulfate, filtered and evaporated. The residue was purified by flash column chromatography (CH$_2$Cl$_2$/MeOH 1:0 to 4:1) to give 0.035 g (15%) of the title compound as off-white solid. MS: 528.2 (MH$^+$).

Example 55

5-Methyl-6-(4-pyrrolidin-1-yl-piperidine-1-carbonyl)-3-(3-trifluoromethyl-phenyl)-pyridine-2-carboxylic acid (2-hydroxy-ethyl)-amide

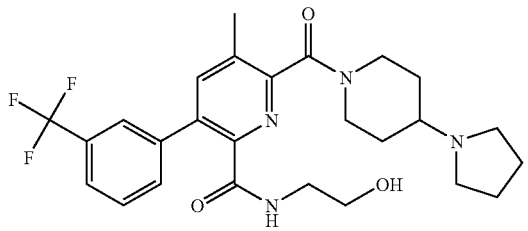

In analogy to the procedure described for the preparation of example 1, 5-methyl-6-(4-pyrrolidin-1-yl-piperidine-1-carbonyl)-3-(3-trifluoromethyl-phenyl)-pyridine-2-carboxylic acid (example 47) was reacted with ethanolamine, Et$_3$N and HATU in DMF to give the title compound as light yellow solid. MS: 505.2 (MH$^+$).

Example 56

5-Methyl-6-(4-pyrrolidin-1-yl-piperidine-1-carbonyl)-3-(3-trifluoromethyl-phenyl)-pyridine-2-carboxylic acid pyridin-3-ylamide

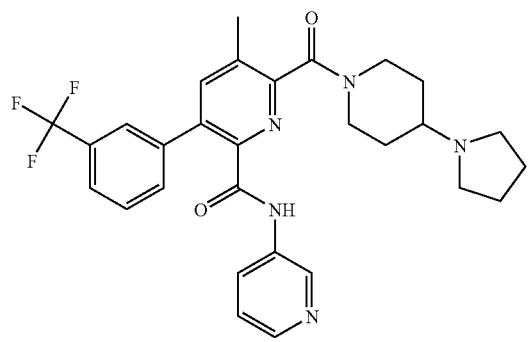

In analogy to the procedure described for the preparation of example 1, 5-methyl-6-(4-pyrrolidin-1-yl-piperidine-1-carbonyl)-3-(3-trifluoromethyl-phenyl)-pyridine-2-carboxylic acid (example 47) was reacted with 3-aminopyridine, Et$_3$N and HATU in DMF to give the title compound as light yellow solid. MS: 538.2 (MH$^+$).

Example 57

4-{[5-Methyl-6-(4-pyrrolidin-1-yl-piperidine-1-carbonyl)-3-(3-trifluoromethyl-phenyl)-pyridine-2-carbonyl]-amino}-piperidine-1-carboxylic acid tert-butyl ester

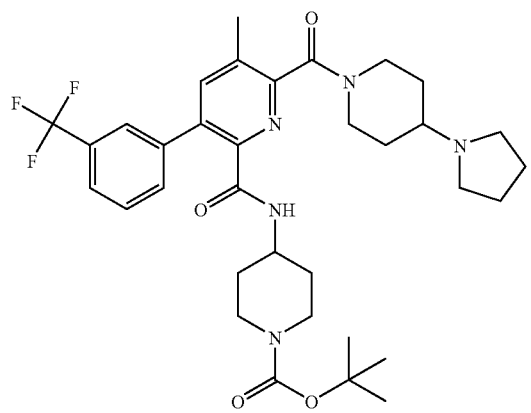

In analogy to the procedure described for the preparation of example 1, 5-methyl-6-(4-pyrrolidin-1-yl-piperidine-1-carbonyl)-3-(3-trifluoromethyl-phenyl)-pyridine-2-carboxylic acid (example 47) was reacted with 4-amino-piperidine-1-carboxylic acid tert-butyl ester, Et$_3$N and HATU in DMF to give the title compound as light yellow solid. MS: 644.3 (MH$^+$).

Example 58

5-Methyl-6-(4-pyrrolidin-1-yl-piperidine-1-carbonyl)-3-(3-trifluoromethyl-phenyl)-pyridine-2-carboxylic acid methylamide

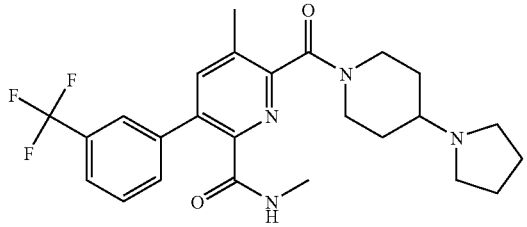

In analogy to the procedure described for the preparation of example 1, 5-methyl-6-(4-pyrrolidin-1-yl-piperidine-1-carbonyl)-3-(3-trifluoromethyl-phenyl)-pyridine-2-carboxylic acid (example 47) was reacted with methylamine (solution in EtOH), Et$_3$N and HATU in DMF to give the title compound as light yellow solid. MS: 475.2 (MH$^+$).

Example 59

4-[5-Methyl-6-(4-pyrrolidin-1-yl-piperidine-1-carbonyl)-3-(3-trifluoromethyl-phenyl)-pyridine-2-carbonyl]-piperazine-1-carboxylic acid tert-butyl ester

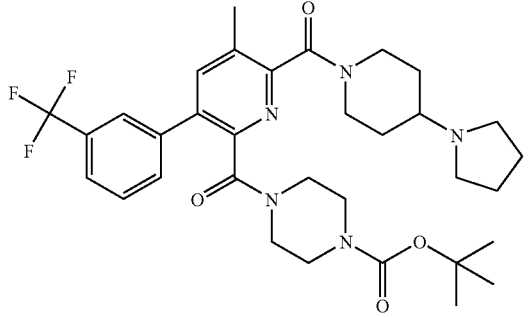

In analogy to the procedure described for the preparation of example 1, 5-methyl-6-(4-pyrrolidin-1-yl-piperidine-1-carbonyl)-3-(3-trifluoromethyl-phenyl)-pyridine-2-carboxylic acid (example 47) was reacted with piperazine-1-carboxylic acid tert-butyl ester, Et$_3$N and HATU in DMF to give the title compound as light yellow solid. MS: 630.3 (MH$^+$).

Example 60

5-Methyl-6-(4-pyrrolidin-1-yl-piperidine-1-carbonyl)-3-(3-trifluoromethyl-phenyl)-pyridine-2-carboxylic acid piperidin-4-ylamide

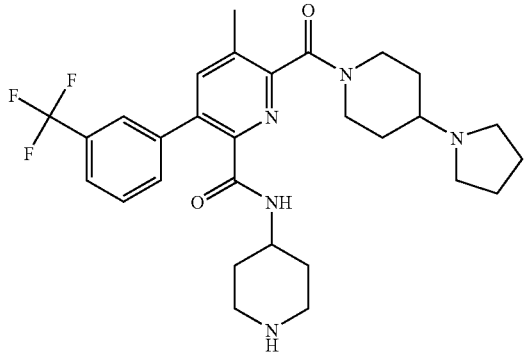

A solution of 0.20 g (0.31 mmol) of 4-[5-methyl-6-(4-pyrrolidin-1-yl-piperidine-1-carbonyl)-3-(3-trifluoromethyl-phenyl)-pyridine-2-carbonyl]-piperazine-1-carboxylic acid tert-butyl ester (example 59) in 10 ml of MeOH was treated with 0.39 ml (1.56 mmol) of HCl in dioxane (4 molar) and the reaction mixture was then stirred at RT. After 18 hours, it was evaporated, poured into crashed ice, the pH was adjusted to 8-9 with sodium carbonate solution and the mixture was then extracted twice with CH$_2$Cl$_2$; the organic phases were washed with water, dried over magnesium sulfate, filtered and evaporated. The residue was purified by flash column chromatography (CH$_2$Cl$_2$/MeOH 95:5 to 4:1) to give 0.127 g (75%) of the title compound as light yellow solid. MS: 544.3 (MH$^+$).

Example 61

[5-Methyl-6-(4-pyrrolidin-1-yl-piperidine-1-carbonyl)-3-(3-trifluoromethyl-phenyl)-pyridin-2-yl]-piperazin-1-yl-methanone

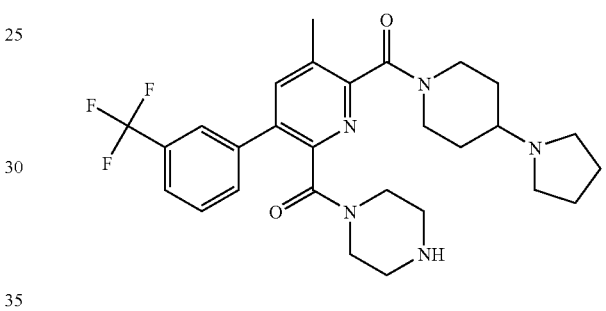

In analogy to the procedure described for the preparation of example 60, 4-[5-methyl-6-(4-pyrrolidin-1-yl-piperidine-1-carbonyl)-3-(3-trifluoromethyl-phenyl)-pyridine-2-carbonyl]-piperazine-1-carboxylic acid tert-butyl ester (example 59) was reacted with HCl/dioxane in methanol to give the title compound as light yellow solid. MS: 530.2 (MH$^+$).

Example 62

[3-Methyl-6-(pyridin-3-yloxy)-5-(3-trifluoromethyl-phenyl)-pyridin-2-yl]-(4-pyrrolidin-1-yl-piperidin-1-yl)-methanone

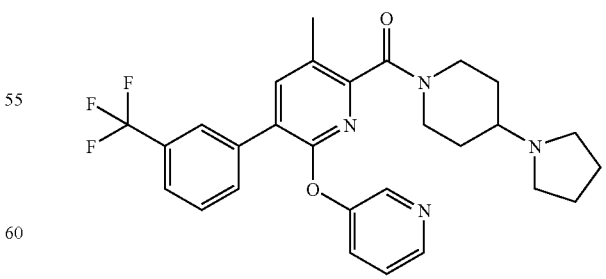

In analogy to the procedure described for the preparation of example 20, [6-chloro-3-methyl-5-(3-trifluoromethyl-phenyl)-pyridin-2-yl]-(4-pyrrolidin-1-yl-piperidin-1-yl)-methanone (example 3) was reacted with pyridin-3-ol and sodium

Example 63

1,5-Dimethyl-6-(4-pyrrolidin-1-yl-piperidine-1-carbonyl)-3-(3-trifluoromethyl-phenyl)-1H-pyridin-2-one

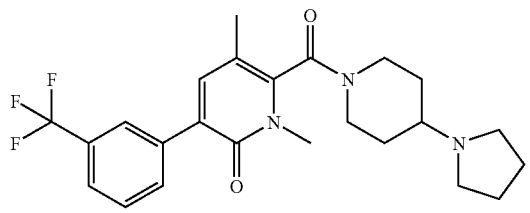

In analogy to the procedure described for the preparation of example 13, 1,3-dimethyl-6-oxo-5-(3-trifluoromethyl-phenyl)-1,6-dihydro-pyridine-2-carboxylic acid [prepared by i) reaction of 6-hydroxy-3-methyl-5-(3-trifluoromethyl-phenyl)-pyridine-2-carboxylic acid methyl ester; 3-methyl-6-oxo-5-(3-trifluoromethyl-phenyl)-1,6-dihydro-pyridine-2-carboxylic acid methyl ester (tautomers, intermediate 15B) with methyl iodide, cesium carbonate in DMF in analogy to the procedure described for the preparation of intermediate 5F; ii) saponification of the thus formed 1,3-dimethyl-6-oxo-5-(3-trifluoromethyl-phenyl)-1,6-dihydro-pyridine-2-carboxylic acid methyl ester with lithium hydroxide in THF/MeOH in analogy to the procedure described for the preparation of intermediate 5G] was reacted with oxalyl chloride/DMF in $CH_2Cl_2$ followed by treatment with 4-pyrrolidin-1-yl-piperidine to give the title compound as colorless solid. MS: 448.2 ($MH^+$).

Example 64

[6-Mercapto-3-methyl-5-(3-trifluoromethyl-phenyl)-pyridin-2-yl]-(4-pyrrolidin-1-yl-piperidin-1-yl)-methanone; [3-Methyl-6-thioxo-5-(3-trifluoromethyl-phenyl)-1,6-dihydro-pyridin-2-yl]-(4-pyrrolidin-1-yl-piperidin-1-yl)-methanone (tautomers)

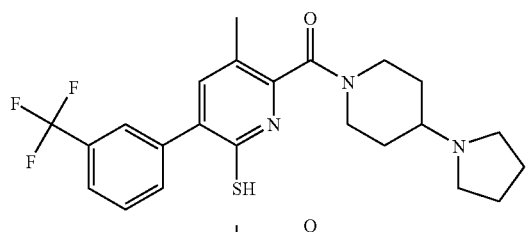

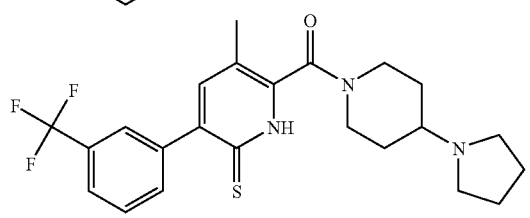

0.45 g (1.0 mmol) of [6-chloro-3-methyl-5-(3-trifluoromethyl-phenyl)-pyridin-2-yl]-(4-pyrrolidin-1-yl-piperidin-1-yl)-methanone (example 3) was dissolved in 10.0 ml of DMF, then 0.18 g (2.50 mmol) of potassium hydrogen sulfide were added and the mixture was heated up to 110° C. After 2 hours, it was cooled down to RT, poured into crashed ice, the pH was adjusted to 7-8 with AcOH (2 molar in $H_2O$) and the mixture was extracted twice with $CH_2Cl_2$; the organic phases were washed with water, dried over magnesium sulfate, filtered and evaporated. The residue was purified by flash column chromatography ($CH_2Cl_2$/MeOH 98:2 to 95:5) to give 0.198 g (44%) of the title compound as off-white solid. MS: 450.2 ($MH^+$).

Example 65

[6-Methyl-8-(3-trifluoromethyl-phenyl)-tetrazolo[1,5-a]pyridin-5-yl]-(4-pyrrolidin-1-yl-piperidin-1-yl)-methanone

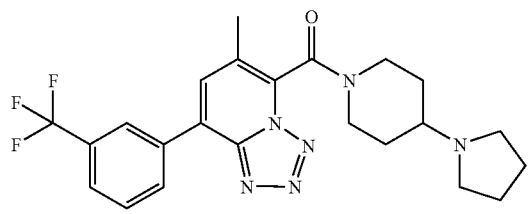

A solution of 0.20 g (0.44 mmol) of [6-chloro-3-methyl-5-(3-trifluoromethyl-phenyl)-pyridin-2-yl]-(4-pyrrolidin-1-yl-piperidin-1-yl)-methanone (example 3) in 2.0 ml of DMF was treated with 0.099 g (1.52 mmol) of a sodium azide and the reaction mixture was heated up to 150° C. After 48 hours, it was poured into crashed ice and extracted twice with EtOAc; the organic phases were washed with water, dried over magnesium sulfate, filtered and evaporated. The residue was purified by flash column chromatography ($CH_2Cl_2$/MeOH 98:2 to 4:1) to give 0.095 g (47%) of the title compound as colorless oil. MS: 459.4 ($MH^-$).

Example 66

[6-(2-Hydroxy-ethoxy)-3-methyl-5-(3-trifluoromethyl-phenyl)-pyridin-2-yl]-(4-pyrrolidin-1-yl-piperidin-1-yl)-methanone

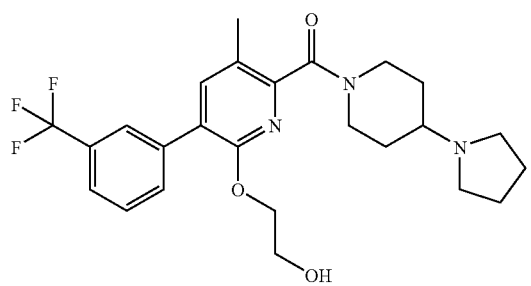

In analogy to the procedure described for the preparation of example 27, [6-(2-benzyloxy-ethoxy)-3-methyl-5-(3-trifluoromethyl-phenyl)-pyridin-2-yl]-(4-pyrrolidin-1-yl-piperidin-1-yl)-methanone [prepared by i) reaction of 6-hydroxy-3-methyl-5-(3-trifluoromethyl-phenyl)-pyridine-2-carboxylic acid methyl ester; 3-methyl-6-oxo-5-(3-trifluoromethyl-phenyl)-1,6-dihydro-pyridine-2-carboxylic acid methyl ester (tautomers, intermediate 15B) with benzyl-2-bromoethyl ether, cesium carbonate, potassium iodide in DMSO in analogy to the procedure described for the preparation of intermediate 5F; ii) saponification of the thus formed 6-(2-benzyloxy-ethoxy)-3-methyl-5-(3-trifluoromethyl-phenyl)-pyridine-2-carboxylic acid methyl ester with lithium hydroxide in THF/MeOH in analogy to the procedure described for the preparation of intermediate 5G; iii) reaction of the thus formed 6-(2-benzyloxy-ethoxy)-3-methyl-5-(3-trifluoromethyl-phenyl)-pyridine-2-carboxylic acid with oxalyl chloride/DMF in CH$_2$Cl$_2$ followed by treatment with 4-pyrrolidin-1-yl-piperidine in analogy to the procedure described for the preparation of example 13] was treated with hydrogen, Pd—C, in MeOH/HCl to give the title compound as colorless oil. MS: 478.2 (MH$^+$).

Example 67

[5-(2-Fluoro-5-trifluoromethyl-phenyl)-3-methyl-1-oxy-pyridin-2-yl]-(4-pyrrolidin-1-yl-piperidin-1-yl)-methanone

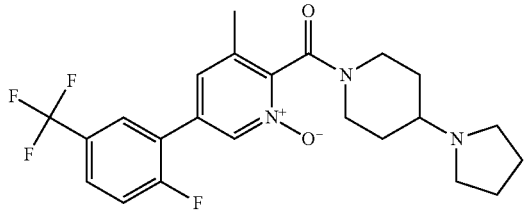

In analogy to the procedure described for the preparation of example 1, 5-(2-fluoro-5-trifluoromethyl-phenyl)-3-methyl-1-oxy-pyridine-2-carboxylic acid [prepared by i) reaction of 5-bromo-3-methyl-pyridine-2-carboxylic acid methyl ester with 2-fluoro-5-trifluoromethyl-phenyl-boronic acid, (1,1'-bis-diphenylphosphino)-ferrocene)palladium-(II)dichloride (1:1 complex with CH$_2$Cl$_2$) and sodium carbonate in dioxane/water in analogy to the procedure described for the preparation of intermediate 1A; ii) oxidation of the thus formed 5-(2-fluoro-5-trifluoromethyl-phenyl)-3-methyl-pyridine-2-carboxylic acid methyl ester with 3-chloro-perbenzoic acid in dichloromethane in analogy to the procedure described for the preparation of intermediate 1C; iii) saponification of the thus formed 5-(2-fluoro-5-trifluoromethyl-phenyl)-3-methyl-1-oxy-pyridine-2-carboxylic acid methyl ester with lithium hydroxide in THF/MeOH in analogy to the procedure described for the preparation of intermediate 5G] was reacted with 4-pyrrolidin-1-yl-piperidine, Et$_3$N and HATU in DMF to give the title compound as light yellow amorphous solid. MS: 452.2 (MH$^+$).

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene Glycol 400 | 150.0 mg |
| Acetic Acid | q.s. ad pH 5.0 |
| Water for injection solutions | Ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula (I) | 50.0 mg |
|---|---|
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula (I):

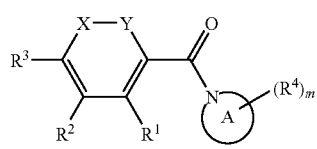

(I)

or a tautomer or pharmaceutically acceptable salt thereof, wherein:

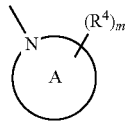

is piperidin-1-yl substituted by m $R^4$ groups wherein m is 0,1,2,3, or 4;

X—Y is selected from the group consisting of:
$C(NR^6R^7)$=N,
$CR^8$=N,
C(O)—$NR^9$, and
$CR^8$=N(O), $R^1$ is selected from the group consisting of: (1) $C_{1-6}$ alkyl, (2) $C_{3-7}$ cycloalkyl, (3) $C_{2-6}$ alkenyl, (4) $C_{2-6}$ alkynyl, (5) optionally substituted $C_{3-7}$ cycloalkyl, (6) optionally substituted $C_{3-7}$ cycloalkyl $C_{1-6}$ alkyl, (7) $C_{1-6}$ alkoxy, (8) halo $C_{1-6}$ alkoxy, (9) halo $C_{1-6}$ alkyl, (10) $C_{3-7}$ cycloalkoxy, (11) heteroalkyl, (12) heteroalkoxy, (13) halogen, (14) optionally substituted phenyl which does not have nitro as a substituent, (15) optionally substituted heteroaryl, and (16) optionally substituted heterocyclyl;

$R^2$ is hydrogen, $C_{1-6}$ alkyl, $C_{2-6}$ alkynyl, $C_{1-6}$ alkoxy, halo $C_{1-6}$ alkyl, cyano or halogen;

$R^3$ is phenyl substituted by one, two or three substituents independently selected from the group consisting of $C_{1-8}$ alkyl, halo $C_{1-6}$ alkyl, $C_{1-6}$ alkoxy, halo $C_{1-6}$ alkoxy, halogen and cyano;

each $R^4$ is independently selected from the group consisting of: (1) hydrogen, (2) $C_{1-6}$ alkyl, (3) hydroxy $C_{1-6}$ alkyl or halo $C_{1-6}$ alkyl, (4) heteroalkyl, (5) $C_{2-6}$ alkenyl, (6) $C_{2-6}$ alkynyl, (7) hydroxy $C_{3-6}$ alkenyl, (8) hydroxy $C_{3-6}$ alkynyl, (9) $C_{1-6}$ alkoxy $C_{3-6}$ alkenyl, (10) $C_{1-6}$ alkoxy $C_{3-6}$ alkynyl, (11) hydroxy, (12) $C_{1-6}$ alkoxy, (13) halo $C_{1-6}$ alkoxy, (14) heteroalkoxy, (15) halogen, (16) cyano, (17) optionally substituted phenyl, (18) optionally substituted $C_{3-7}$ cycloalkyl, (19) optionally substituted $C_{3-7}$ cycloalkyl $C_{1-6}$ alkyl, (20) optionally substituted heteroaryl, (21) optionally substituted heterocyclyl, (22) optionally substituted phenyl-$C_{1-6}$ alkyl, (23) optionally substituted heteroaryl-$C_{1-6}$ alkyl, (24) optionally substituted heterocyclyl-$C_{1-6}$ alkyl, (25) nitro, (26) carboxy, (27) formyl, (28) acyl, (29) $C_{1-6}$ alkoxycarbonyl, (30) carbamoyl, (31) mono- or di-$C_{1-6}$ alkyl substituted aminocarbonyl, (32) $C_{1-6}$ alkylthio, (33) $C_{1-6}$ alkylsulfinyl, (34) $C_{1-6}$ alkylsulfonyl, and (35) amino optionally substituted by one or two substituents independently selected from the group consisting of $C_{1-6}$ alkyl, heteroalkyl, optionally substituted $C_{3-7}$ cycloalkyl and optionally substituted heterocyclyl;

$R^6$ is selected from the group consisting of:
hydrogen, $C_{1-6}$ alkyl, $C_{1-6}$ alkanoyl, $C_{1-6}$ alkylsulfonyl, $C_{3-7}$ cycloalkyl, optionally substituted phenyl-$C_{1-6}$ alkyl, optionally substituted heteroaryl-$C_{1-6}$ alkyl, and optionally substituted heterocyclyl-$C_{1-6}$ alkyl;

$R^7$ is selected from the group consisting of:
hydrogen, $C_{1-6}$ alkyl, $C_{3-7}$ cycloalkyl, halo $C_{1-6}$ alkyl, $C_{1-6}$ alkanoyl, and heteroalkyl;

$R^8$ is selected from the group consisting of: (1) hydrogen, (2) hydroxy, (3) mercapto, (4) $C_{1-6}$ alkyl, (5) $C_{3-7}$ cycloalkyl, (6) $C_{2-6}$ alkenyl, (7) $C_{2-6}$ alkynyl, (8) optionally substituted $C_{3-7}$ cycloalkyl, (9) optionally substituted $C_{3-7}$ cycloalkyl $C_{1-6}$ alkyl, (10) $C_{1-6}$ alkoxy, (11) $C_{1-6}$ alkylthio, (12) halo $C_{1-6}$ alkoxy, (13) halo $C_{1-6}$ alkyl, (14) $C_{3-7}$ cycloalkoxy, (15) heteroalkyl, (16) heteroalkoxy, (17) halogen, (18) cyano, (19) optionally substituted phenyl, (20) optionally substituted heteroaryl, (21) optionally substituted heterocyclyl, (22) optionally substituted phenyloxy, (23) optionally substituted heteroaryloxy; (24) optionally substituted phenylthio, (25) optionally substituted heteroarylthio; (26) optionally substituted phenyl-$C_{1-6}$ alkoxy, (27) optionally substituted heteroaryl-$C_{1-6}$ alkoxy, (28) $C_{1-6}$ alkoxy-carbonyl, (29) carboxy, and (30) —$CONR^{13}R^{14}$;

$R^9$ is hydrogen, $C_{1-6}$ alkyl, $C_{3-7}$ cycloalkyl, halo $C_{1-6}$ alkyl, heteroalkyl, optionally substituted heteroaryl, optionally substituted phenyl-$C_{1-6}$ alkyl, or optionally substituted heteroaryl-$C_{1-6}$ alkyl;

$R^{13}$ is hydrogen, $C_{1-6}$ alkyl, heteroalkyl, optionally substituted $C_{3-7}$ cycloalkyl, optionally substituted heterocyclyl, optionally substituted aryl, or optionally substituted heteroaryl; and $R^{14}$ is hydrogen, $C_{1-6}$ alkyl or heteroalkyl; or alternatively, $R^{13}$ and $R^{14}$ taken together with the nitrogen atom to which they are attached, form an optionally substituted heterocyclyl ring.

2. A compound of claim 1, wherein X—Y is $C(NR^6R^7)$=N, $CR^8$=N or C(O)—$NR^9$.

3. A compound of claim 1, wherein X—Y is $C(NH_2)$=N, CH=N, C(CI)=N, C(O)—NH, C(pyridinyl)=N, C(triazolyl)=N, $C(NH((CH_2)_2OH))$=N, $C(NH_2$-pyrimidinyl)=N, $C(CH_2OH)$=N, C(pyrazinyl)=N, C(C(O)NH (pyridinyl))=N, or C(O) —$N(CH_3)$.

4. A compound of claim 1, wherein X—Y is $C(NH_2)$=N, $C(NH_2$-pyrimidinyl)=N, C(pyrazinyl)=N, C(triazolyl)=N or C)—NH 5. A compound of claim 1, wherein m is 1.

6. A compound of claim 1, wherein $R^4$ is optionally substituted heterocyclyl or heteroalkyl.

7. A compound of claim 1, wherein $R^4$ is hydroxy $C_{1-6}$ alkyl, optionally substituted pyrrolidin-1-yl, or optionally substituted piperidin-1-yl.

8. A compound of claim 1, wherein $R^4$ is piperidin-1-yl or pyrrolidin-1-yl, wherein said piperidin-1-yl or pyrrolidin-1-yl is optionally substituted by hydroxyl $C_{1-6}$ alkyl or hydroxy.

9. A compound of claim 1, wherein $R^4$ is pyrrolidin-1-yl, 2-hydroxymethyl-pyrrolidin-1-yl or 4-hydroxy-piperidin-1-yl.

10. A compound of claim 1, wherein:

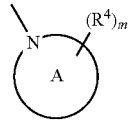

is 4-pyrrolidin-1-yl-piperidin-1-yl, 4-(2-hydroxymethyl-pyrrolidin-1-yl)- piperidin-1-yl, or 4-hydroxy-[1,4']bipiperidinyl-1'-yl.

11. A compound of claim 1, wherein $R^1$ is $C_{1-6}$ alkyl, halogen, or optionally substituted phenyl, and $R^2$ is hydrogen or halogen.

12. A compound of claim 1, wherein $R^1$ is $C_{1-6}$ alkyl and $R^2$ is hydrogen.

13. A compound of claim 1, wherein $R^1$ is methyl and $R^2$ is hydrogen.

14. A compound of claim 1, wherein $R^3$ is optionally substituted by one or two substituents independently selected from the group consisting of trifluoromethyl and trifluoromethoxy.

15. A compound of claim 1, wherein $R^3$ is 3-trifluoromethyl phenyl.

16. A compound of claim 1, wherein $R^{13}$ is hydrogen, $C_{1-6}$ alkyl, heteroalkyl, pyridinyl, optionally substituted piperidinyl, optionally substituted piperazinyl and $R^{14}$ is hydrogen.

17. A compound of claim 1, wherein $R^{13}$ is hydrogen, methyl, hydroxyethyl, 1-carboxylic acid-t-butyl ester-piperidin-4-yl, pyridin-3yl, 1-carboxylic acid-t-butyl ester-piperazin-4-yl, piperidin-4-yl or piperazin-4-yl and $R^{14}$ is hydrogen.

18. A compound of claim 1, selected from the group consisting of:

[3-Methyl-5-(3-trifluoromethyl-phenyl) -pyridin-2-yl]-(4-pyrrolidin-1-yl-piperidin-1-yl)-methanone,

[6-Chloro-3-methyl-5-(3-trifluoromethyl-phenyl) -pyridin-2-yl]-(4-pyrrolidin-1-yl-piperidin-1-l) -methanone,

[4((S)-2-Hydroxymethyl-pyrrolidin-1-yl) -piperidin-1-yl]-[3-methyl-5-(3-trifluoromethyl-phenyl)-pyridin-2-yl ]-A-methanone,

[6-Hydroxy-3-methyl-5-(3-trifluoromethyl-phenyl) -pyridin-2-yl]-(4-pyrrolidin-1-yl-piperidin-1-yl)-methanone, 5-Methyl-6-(4-yrrolidin-1-yl-piperidine-1-carbonyl) -3-(3-trifluoromethyl-phenyl) -1 H-pyridin-2-one,

[6-Amino-3-methyl-5-(3-trifluoromethyl-phenyl) -pyridin-2-yl]-(4-pyrrolidin-1-yl-piperidin-1-y1)-methanone,

[5-Methyl-3-(3-trifluoromethyl-phenyl) -[2,3']bipyridinyl-6-yl) -(4-pyrrolidin-1-yl-piperidin-1-y1)-methanone,

[3-Chloro-6-hydroxy-5-(3-trifluoromethyl-phenyl) -pyridin-2-yl]-(4-pyrrolidin-1 -yl-piperidin-1-yl)-methanone, 5-Chloro-6-(4-pyrrolidin-1-yl-piperidine-1-carbonyl) -3-(3-trifluoromethyl-phenyl) -1 H-pyridin-2-one, and

[3-Methyl-6-[1,2,4]triazol-1-yl-5-(3-trifluoromethyl-phenyl) -pyridin-2-yl]-(4-pyrrolidin-1-yl-piperidin-1-yl)-methanone.

19. A process for manufacturing a compound of formula (I):

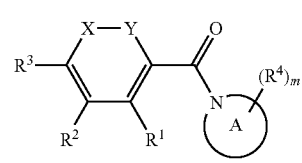

comprising a step of reacting a compound of formula (II):

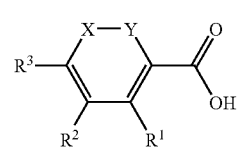

with a compound of formula (III):

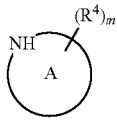

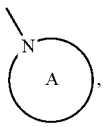

wherein
m, $R^1$, $R^2$, $R^3$, $R^4$, X—Y are as defined in claim 1.

20. A pharmaceutical composition comprising a compound of claim 1 and a pharmaceutically acceptable excipient.

21. A compound of claim 1, selected from the group consisting of:
- [6-(2-Hydroxy-ethylamino) -3-methyl-5-(3-trifluoromethyl-phenyl)-pyridin-2-yl]-(4-pyrrolidin-1-yl-piperidin-1-yl)-methanone,
- [5-(2-Fluoro-5-trifluoromethyl-phenyl)-3-methyl-pyridin-2-yl]-(4-pyrrolidin-1-yl-piperidin-1-yl)-methanone,
- [3-Methyl-6-(1H-[1,2,3]triazol-4-yl)-5-(3-trifluoromethyl-phenyl)-pyridin-2-yl]-(4-pyrrolidin-1-yl-piperidin-1-yl)-methanone,
- [5-(2-Methoxy-5-trifluoromethyl-phenyl)-3-methyl-pyridin-2-yl]-(4-pyrrolidin-1-yl-piperidin-1-yl)-methanone,
- [6-(2-Amino-pyrimidin-5-yl)-3-methyl-5-(3-trifluoromethyl-phenyl)-pyridin-2-yl]-(4-pyrrolidin-1-yl-piperidin-1-yl)-methanone,
- [6-Hydroxymethyl-3-methyl-5-(3-trifluoromethyl-phenyl)-pyridin-2-yl]-(4-pyrrolidin-1-yl-piperidin-1-yl)-methanone,
- [3-Methyl-6-pyrazin-2-yl-5-(3-trifluoromethyl-phenyl)-pyridin-2-yl]-(4-pyrrolidin-1-yl-piperidin-1-yl)-methanone,
- 5-Methyl-6-(4-pyrrolidin-1-yl-piperidine-1-carbonyl)-3-(3-trifluoromethyl-phenyl)-pyridine-2-carboxylic acid pyridin-3-ylamide, and
- 1,5-Dimethyl-6-(4-pyrrolidin-1-yl-piperidine-1-carbonyl)-3-(3-trifluoromethyl-phenyl)-1H-pyridin-2-one.

* * * * *

UNITED STATES PATENT AND TRADEMARK OFFICE
CERTIFICATE OF CORRECTION

PATENT NO.         : 8,227,613 B2                    Page 1 of 1
APPLICATION NO.    : 12/484552
DATED              : July 24, 2012
INVENTOR(S)        : Adam et al.

It is certified that error appears in the above-identified patent and that said Letters Patent is hereby corrected as shown below:

Claim 4, column 83, line 35, delete "or C)-NH" and insert -- or C(O)-NH --

Claim 18, column 84, end of line 21, delele "-1-1)-methanone," and insert -- 1-yl)-methanone, --

Claim 18, column 84, line 24, delete "yl]-A-methanone," and insert -- yl]-methanone --

Claim 18, column 84, line 39, delete entire line and insert -- none, --

Claim 18, column 84, line 40, insert -- 5-Chloro-6-(4-pyrrolidin-1-yl-piperidine-1-car --
at the beginning of line 40

Signed and Sealed this
Sixth Day of November, 2012

David J. Kappos
*Director of the United States Patent and Trademark Office*